US011933785B2

(12) United States Patent
Sussman et al.

(10) Patent No.: US 11,933,785 B2
(45) Date of Patent: Mar. 19, 2024

(54) METHODS FOR DETECTION, STAGING, AND SURVEILLANCE OF COLORECTAL ADENOMAS AND CARCINOMAS

(71) Applicant: Wisconsin Alumni Research Foundation, Madison, WI (US)

(72) Inventors: Michael Richard Sussman, Cross Plains, WI (US); Melanie Mae Ivancic, Madison, WI (US); Gregory D Kennedy, Madison, WI (US); William Franklin Dove, Madison, WI (US); Perry Joseph Pickhardt, Madison, WI (US); Mark Reichelderfer, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 1183 days.

(21) Appl. No.: 16/307,779

(22) PCT Filed: Jun. 12, 2017

(86) PCT No.: PCT/US2017/037045
§ 371 (c)(1),
(2) Date: Dec. 6, 2018

(87) PCT Pub. No.: WO2017/214625
PCT Pub. Date: Dec. 14, 2017

(65) Prior Publication Data
US 2019/0302120 A1 Oct. 3, 2019

Related U.S. Application Data

(60) Provisional application No. 62/348,290, filed on Jun. 10, 2016.

(51) Int. Cl.
*G01N 31/00* (2006.01)
*G01N 33/53* (2006.01)
*G01N 33/574* (2006.01)

(52) U.S. Cl.
CPC ......... *G01N 33/57419* (2013.01); *G01N 2333/4704* (2013.01); *G01N 2333/4716* (2013.01); *G01N 2333/4728* (2013.01); *G01N 2333/4737* (2013.01); *G01N 2333/70585* (2013.01); *G01N 2333/71* (2013.01); *G01N 2333/7456* (2013.01); *G01N 2333/81* (2013.01); *G01N 2333/90212* (2013.01); *G01N 2333/90283* (2013.01); *G01N 2800/60* (2013.01)

(58) Field of Classification Search
None
See application file for complete search history.

(56) References Cited

FOREIGN PATENT DOCUMENTS

| WO | WO-2014085826 A2 * | 6/2014 | ............. G16B 20/20 |
| WO | WO-2014183777 A1 * | 11/2014 | ......... G01N 33/6893 |
| WO | WO2016094692 A1 | 6/2016 | |

OTHER PUBLICATIONS

Surinova et al. (EMBO Mol Med, 2015 vol. 7, pp. 1153-1165) (Year: 2015).*
Ivancic et al. J. Proteomic Research, Sep. 6, 2013; 12(9), 4152-4166. doi: 10.1021/pr.400467a (Year: 2013).*
Surinova et al. EMBO Mol. Med. Sep. 2015. 7(9), 1153-65 (Year: 2015).*
Siegel, et al., "Cancer statistics, 2016", CA: A Cancer Journal for Clinicians, 66:7-30 (2016).
Winawer, et al., "Evidence-Based, Reality-Driven Colorectal Cancer Screening Guidelines: The Critical Relationship of Adherence to Effectiveness", JAMA: the journal of the American Medical Association, 315:2065-2066 (2016).
Kruse, et al., "Overuse of colonoscopy for colorectal cancer screening and surveillance", J. Gen Intern Med., 30:37-83 (2015).
Austin, et al., "Can colonoscopy remain cost-effective for colorectal cancer screening? The impact of practice patterns and the Will Rogers phenomenon on costs", The American Journal of Gastroenterology, 108:296-301 (2013).
Ranasinghe, et al., "Differences in Colonoscopy Quality Among Facilities Development of a Post-Colonoscopy Risk-Standardized Rate of Unplanned Hospital Visits", Gastroenterology, 150:103-13 (2016).
Suehiro, et al., "Genetic and epigenetic changes in aberrant crypt foci and serrated polyps", Cancer Science, 99:1071-1076 (2008).
Fearon, et al., "Clonal analysis of human colorectal tumors", Science, 238:193-197 (1987).
Maak, et al., "Independent Validation of a Prognostic Genomic Signature (ColoPrint) for Patients With Stage II Colon Cancer", Annals of Surgery, 257:1053-1058(2013).
Artinyan, et al., "Infectious postoperative complications decrease long-term survival in patients undergoing curative surgery for colorectal cancer: a study of 12,075 patients", Annals of Surgery, 261:497-505 (2015).
Gundersen, et al., "Revised TN categorization for colon cancer based on national survival outcomes data", Journal of clinical oncology: Official Journal of the American Society of Clinical Oncology, 28:264-271 (2010).
Greene, FL, "The American Joint Committee on Cancer: updating the strategies in cancer staging", Bulletin of the American College of Surgeons, 87:13-15 (2002).
Dukes, C.E., "The classification of cancer of the rectum", Journal of Pathological Bacteriology, 35:323-332 (1932).

(Continued)

Primary Examiner — Lisa V Cook
(74) Attorney, Agent, or Firm — McDonnell Boehnen Hulbert & Berghoff LLP

(57) ABSTRACT

This invention provides minimally invasive methods, reagents, diagnostic and prognostic markers useful for staging, prognosis and surveillance of colorectal cancers, and therapeutic intervention in individuals with colorectal cancers, or individuals who may be susceptible to developing colorectal cancers.

13 Claims, 51 Drawing Sheets

Specification includes a Sequence Listing.

(56) References Cited

OTHER PUBLICATIONS

Astler, et al., "The Prognostic Significance of Direct Extension of Carcinoma of the Colon and Rectum", Annals of Surgery, 139:846-851 (1954).
Chen, et al., "Proteins of the inter-alpha-trypsin inhibitor family stabilize the cumulus extracellular matrix through their direct binding with hyaluronic acid", The Journal of Biological Chemistry, 269:28282-28287 (1994).
Misra, et al., "CD44, and cyclooxygenase-2 in colon cancer", Connective Tissue Research, 49:219-224 (2008).
Chong, et al., "ITIH3 is a potential biomarker for early detection of gastric cancer", Journal of Proteome Research, 9:3671-3679 (2010).
Lieto, et al., "Expression of vascular endothelial growth factor (VEGF) and epidermal growth factor receptor (EGFR) is an independent prognostic indicator of worse outcome in gastric cancer patients", Annals of Surgical Oncology, 15:69-79 (2008).
Hsu, et al., "Identification of Fetuin-B as a member of a cystatin-like gene family on mouse chromosome 16 with tumor suppressor activity", Genome/National Research Council Canada, 47:931-946 (2004).
Hirano, et al., "Up-regulation of the Expression of leucine-rich alpha(2)-glycoprotein in hepatogcytes by the mediators of acute-phae response", Biochemical and biophysical research communications, 382:776-779 (2009).
Ladd, et al., "Increased plasma levels of the APC-interacting protein MAPREI1, LRg1, and IGFBP2 preceding a diagnosis of colorectal cancer in women", Cancer Pre Res (Phila), 5:655-664 (2012).
Hung, et al., "Comprehensive proteome analysis of an Apc mouse model uncovers proteins associated with intestinal tumorigenesis", Cancer Prev Res (Phila), 2:224-233 (2009).
Ivancic, et al., "Candidate serum biomarkers for early intestinal cancer using 15N metabolic labeling and quantitative proteomics in the ApcMin/+ mouse", Journal of proteome research, 12:4152-41669 (2013).
Serada, et al., Serum leucine-rich alpha-2 glycoprotein is a disease activity biomarker in ulcerative colitis, Inflammatory bowel diseases, 18:2169-2179 (2012).
Wang, et al., LRG1 promotes angiogenesis by modulating endothelial TGF-beta signalling, Nature 499:306-311 (2013).
Hanahan, et al., Hallmarks of cancer: the next generation, Cell, 144:646-74 (2011).
Surinova, et al., "Non-invasive prognostic protein biomarker signatures associated with colorectal cancer", EMBO Mol Med., 7:1153-1165 (2015).
Surinova, et al., "Prediction of colorectal cancer diagnosis based on circulating plasma proteins", EMBO Mol Med., 7:1166-1178 (2015).
Davie, et al., "The coagulation cascade: initiation, maintenance, and regulation", Biochemistry, 30:10363-70 (1991).
Falanga, et al., Coagulation and cancer: biological and clinical aspects, Journal of thrombosis and haemostasis, 11:223-233 (2013).
Alcalay, et al., "Venous thromboembolism in patients with colorectal cancer: incidence and effect on survival", Journal of Clinical Oncology, 24:1112-1118 (2006).
Paspatis, et al., "Resistance to activated protein C, factor V leiden and the prothrombin G20210A variant in patients with colorectal cancer", Pathophysiology of haemostasis and thrombosis, 32:2-7 (2002).
Vossen, et al., "Clotting factor gene polymorphisms and colorectal cancer risk", Journal of clinical oncology: official journal of the American Society of Clinical Oncology, 29:1722-1727 (2011).
Yocum, et al., "Current affairs in quantitative targeted preteomics: multiple reaction monitoring-mass spectrometry", Briefing in functional genomics & proteomics, 8:145-157 (2009).
Gerber, et al., "Absolute quantification of proteins and phosphoproteins from cell lysates by tandem MS", Proceedings of the national Academy of Sciences in the United States of America, 100:6940-6945 (2003).
Kasier, et al., "Protein standard absolute quantification (PSAQ) method for the measurement of cellular ubiquitin pools", Nature Methods, 8:691-696 (2011).
Pratt, et al., "Multiplexed absolute quantification for proteomics using concatenated signature peptides encoded by QconCAT genes", Nature protocols 1:1024-1043 (2006).
Lange, et al., "Selected reaction monitoring for quantitative proteomics: a tutorial", Molecular Systems Biology, 4:222 (2008).
Elias, et al., "Comparative evaluation of mass spectrometry platforms used in large-scale proteomics investigations", Nature methods, 2:667-675 (2005).
Kirkpatrick, et al., "The absolute quantification strategy: a general procedure for the quantification of proteins and post-translational modifications", Methods, 35:265-73 (2005).
Picotti, et al., "A complete mass-spectrometric map of the yeast proteome applied to quantitative trait analysis", Nature 494:266-70 (2013).
Banack, et al., Distinguishing the cyanobacterial neurotoxin beta-N-methylamino-L-alanine (BMAA) from its structural somer 2,4-diaminobuityric acid (2,4-DAB), Toxicon: official journal of the International Society on Toxinology, 56:868-79 (2010).
Mantovani, et al., "Cancer-related inflammation", Nature 454:436-444 (2008).
Grivennikova, et al., "Immunity, Inflammation, and Cancer", Cell, 140:883-899 (2010).
Ivancic, et al., "The concentrations of EGFR, LRG1, ITIH4, and F5 in serum correlate with the number of colonic adenomas in ApcPirc/+ rats", Cancer Prev. Res, 7:1160-1169 (2014).
Burges, CJC., "A Tutorial on Support Vector Machines for Pattern Recognition", Data Mining and Knowledge Discovery, 2:121-167 (1998).
Zou, et al., "Receiver-operating characteristic analysis for evaluating diagnostic tests and predictive models", Circulation, 115:654-657 (2007).

\* cited by examiner

|  |  | Non-Cancer | Cancer |
|---|---|---|---|
| Total Cases |  | 214 | 49 |
| Gender | Males | 105 | 23 |
|  | Females | 107 | 26 |
|  | Not Reported | 2 | 0 |
| Age | Median | 60 | 62 |
|  | Range | 30-80 | 37-88 |
| Number of Polyps | 0 | 56 | N/A |
|  | 1-2 | 107 |  |
|  | 3+ | 51 |  |
| Advanced Adenoma Cases |  | 71 | N/A |
| Cancer Cases By Stage | Stage 1 | N/A | 22 |
|  | Stage 2 |  | 13 |
|  | Stage 3 |  | 12 |
|  | Other |  | 2 |
| Pre-Operative CEA Level (ng/mL) | Median | N/A | 1.95 |
|  | Range |  | 0.7-119 |

FIG. 5

Pre- Post- Polypectomy data

If the Pre-polypectomy ratio-to-reference standard is upregulated, then the post-polypectomy ratio-to-reference standard should be reduced. The ratio of Pre-/Post-polypectomy is greater than 1

Example: Pre = 2, Post = 0.5 (Pre/Post = 4)

If the Pre-polypectomy ratio-to-reference standard is downregulated, then the post-polypectomy ratio-to-reference standard should be increased. The ratio of Pre/Post-polypectomy is less than 1

Example: Pre = 0.5, Post = 2 (Pre/Post = 0.25)

FIG. 7

```
                       SEQUENCE LISTING

<160> NUMBER OF SEQ ID NOS: 30

<210> SEQ ID NO 1
<211> LENGTH: 12
<212> TYPE: PRT
<213> ORGANISM: Artificial Sequence
<220> FEATURE:
<223> OTHER INFORMATION: Synthetic CD44 antigen biomarker peptide

<400> SEQUENCE: 1

Tyr Gly Phe Ile Glu Gly His Val Val Ile Pro Arg
1               5                   10

<210> SEQ ID NO 2
<211> LENGTH: 10
<212> TYPE: PRT
<213> ORGANISM: Artificial Sequence
<220> FEATURE:
<223> OTHER INFORMATION: Synthetic Complement Factor I biomarker peptide

<400> SEQUENCE: 2

Val Phe Ser Leu Gln Trp Gly Glu Val Lys
1               5                   10

<210> SEQ ID NO 3
<211> LENGTH: 10
<212> TYPE: PRT
<213> ORGANISM: Artificial Sequence
<220> FEATURE:
<223> OTHER INFORMATION: Synthetic Leucine-Rich alpha-2-glycoprotein
      biomarker peptide

<400> SEQUENCE: 3

Val Ala Ala Gly Ala Phe Gln Gly Leu Arg
1               5                   10

<210> SEQ ID NO 4
<211> LENGTH: 10
<212> TYPE: PRT
<213> ORGANISM: Artificial Sequence
<220> FEATURE:
<223> OTHER INFORMATION: Synthetic Collagen alpha-1(I) chain biomarker
      peptide

<400> SEQUENCE: 4

Ser Leu Ser Gln Gln Ile Glu Asn Ile Arg
1               5                   10

<210> SEQ ID NO 5
<211> LENGTH: 10
<212> TYPE: PRT
<213> ORGANISM: Artificial Sequence
<220> FEATURE:
<223> OTHER INFORMATION: Synthetic Epidermal Growth Factor Receptor
      biomarker peptide

<400> SEQUENCE: 5

Ile Pro Leu Glu Asn Leu Gln Ile Ile Arg
```

```
<210> SEQ ID NO 6
<211> LENGTH: 12
<212> TYPE: PRT
<213> ORGANISM: Artificial Sequence
<220> FEATURE:
<223> OTHER INFORMATION: Synthetic Epidermal Growth Factor Receptor
      biomarker peptide

<400> SEQUENCE: 6

Asn Tyr Val Val Thr Asp His Gly Ser Cys Val Arg
1               5                   10

<210> SEQ ID NO 7
<211> LENGTH: 10
<212> TYPE: PRT
<213> ORGANISM: Artificial Sequence
<220> FEATURE:
<223> OTHER INFORMATION: Synthetic Inter-alpha-trypsin inhibitor heavy
      chain H3 biomarker peptide

<400> SEQUENCE: 7

Glu Val Ser Phe Asp Val Glu Leu Pro Lys
1               5                   10

<210> SEQ ID NO 8
<211> LENGTH: 10
<212> TYPE: PRT
<213> ORGANISM: Artificial Sequence
<220> FEATURE:
<223> OTHER INFORMATION: Synthetic Maltase Glucoamylase biomarker
      peptide

<400> SEQUENCE: 8

Ala Tyr Val Ala Phe Pro Asp Phe Phe Arg
1               5                   10

<210> SEQ ID NO 9
<211> LENGTH: 17
<212> TYPE: PRT
<213> ORGANISM: Artificial Sequence
<220> FEATURE:
<223> OTHER INFORMATION: Synthetic Maltase Glucoamylase biomarker
      peptide

<400> SEQUENCE: 9

Ser Ser Val Tyr Ala Asn Ala Phe Pro Ser Thr Pro Val Asn Pro Leu
1               5                   10                  15

Arg

<210> SEQ ID NO 10
<211> LENGTH: 10
<212> TYPE: PRT
<213> ORGANISM: Artificial Sequence
<220> FEATURE:
<223> OTHER INFORMATION: Synthetic Coagulation factor V biomarker
      peptide

<400> SEQUENCE: 10

Asn Phe Phe Asn Pro Pro Ile Ile Ser Arg
1               5                   10

<210> SEQ ID NO 11
<211> LENGTH: 7
<212> TYPE: PRT
<213> ORGANISM: Artificial Sequence
```

```
<220> FEATURE:
<223> OTHER INFORMATION: Synthetic Hemopexin biomarker peptide

<400> SEQUENCE: 11

Leu Trp Trp Leu Asp Leu Lys
1               5

<210> SEQ ID NO 12
<211> LENGTH: 13
<212> TYPE: PRT
<213> ORGANISM: Artificial Sequence
<220> FEATURE:
<223> OTHER INFORMATION: Synthetic Isocitrate dehydrogenase [NADP],
      mitochondrial biomarker peptide

<400> SEQUENCE: 12

Thr Ile Glu Ala Glu Ala Ala His Gly Thr Val Thr Arg
1               5                   10

<210> SEQ ID NO 13
<211> LENGTH: 16
<212> TYPE: PRT
<213> ORGANISM: Artificial Sequence
<220> FEATURE:
<223> OTHER INFORMATION: Synthetic Pyruvate Kinase, M2 biomarker peptide

<400> SEQUENCE: 13

Glu Ala Glu Ala Ala Ile Tyr His Leu Gln Leu Phe Glu Glu Leu Arg
1               5                   10                  15

<210> SEQ ID NO 14
<211> LENGTH: 7
<212> TYPE: PRT
<213> ORGANISM: Artificial Sequence
<220> FEATURE:
<223> OTHER INFORMATION: Synthetic Vitamin D-binding protein biomarker
      peptide

<400> SEQUENCE: 14

Val Leu Glu Pro Thr Leu Lys
1               5

<210> SEQ ID NO 15
<211> LENGTH: 12
<212> TYPE: PRT
<213> ORGANISM: Artificial Sequence
<220> FEATURE:
<223> OTHER INFORMATION: Synthetic Vitronectin biomarker peptide

<400> SEQUENCE: 15

Phe Glu Asp Gly Val Leu Asp Pro Asp Tyr Pro Arg
1               5                   10

<210> SEQ ID NO 16
<211> LENGTH: 9
<212> TYPE: PRT
<213> ORGANISM: Artificial Sequence
<220> FEATURE:
<223> OTHER INFORMATION: Synthetic Inter-alpha-trypsin inhibitor, Heavy
      chain 4 biomarker peptide

<400> SEQUENCE: 16

Phe Ala His Thr Val Val Thr Ser Arg
1               5

<210> SEQ ID NO 17
<211> LENGTH: 9
```

```
<212> TYPE: PRT
<213> ORGANISM: Artificial Sequence
<220> FEATURE:
<223> OTHER INFORMATION: Synthetic CEACAM5 biomarker peptide

<400> SEQUENCE: 17

Thr Leu Thr Leu Leu Ser Val Thr Arg
1               5

<210> SEQ ID NO 18
<211> LENGTH: 14
<212> TYPE: PRT
<213> ORGANISM: Artificial Sequence
<220> FEATURE:
<223> OTHER INFORMATION: Synthetic Cathepsin B biomarker peptide

<400> SEQUENCE: 18

Leu Cys Gly Thr Phe Leu Gly Gly Pro Lys Pro Pro Gln Arg
1               5                   10

<210> SEQ ID NO 19
<211> LENGTH: 11
<212> TYPE: PRT
<213> ORGANISM: Artificial Sequence
<220> FEATURE:
<223> OTHER INFORMATION: Synthetic Serum Amyloid P biomarker peptide

<400> SEQUENCE: 19

Gly Tyr Val Ile Ile Lys Pro Leu Val Trp Val
1               5                   10

<210> SEQ ID NO 20
<211> LENGTH: 11
<212> TYPE: PRT
<213> ORGANISM: Artificial Sequence
<220> FEATURE:
<223> OTHER INFORMATION: Synthetic Fetuin B biomarker peptide

<400> SEQUENCE: 20

Ile Phe Phe Glu Ser Val Tyr Gly Gln Cys Lys
1               5                   10

<210> SEQ ID NO 21
<211> LENGTH: 10
<212> TYPE: PRT
<213> ORGANISM: Artificial Sequence
<220> FEATURE:
<223> OTHER INFORMATION: Synthetic C-reactive protein biomarker peptide

<400> SEQUENCE: 21

Glu Ser Asp Thr Ser Tyr Val Ser Leu Lys
1               5                   10

<210> SEQ ID NO 22
<211> LENGTH: 15
<212> TYPE: PRT
<213> ORGANISM: Artificial Sequence
<220> FEATURE:
<223> OTHER INFORMATION: Synthetic heparin cofactor 2 biomarker peptide

<400> SEQUENCE: 22

Phe Thr Val Asp Arg Pro Phe Leu Phe Leu Ile Tyr Glu His Arg
1               5                   10                  15

<210> SEQ ID NO 23
<211> LENGTH: 13
<212> TYPE: PRT
```

```
<213> ORGANISM: Artificial Sequence
<220> FEATURE:
<223> OTHER INFORMATION: Synthetic Sulfhydryl Oxidase 1 biomarker
      peptide

<400> SEQUENCE: 23

Leu Ala Gly Ala Pro Ser Glu Asp Pro Gln Phe Pro Lys
1               5                   10

<210> SEQ ID NO 24
<211> LENGTH: 15
<212> TYPE: PRT
<213> ORGANISM: Artificial Sequence
<220> FEATURE:
<223> OTHER INFORMATION: Synthetic Rho-GDP Dissociation Inhibitor 1,
      Isoform a (ARHGDIA) biomarker peptide

<400> SEQUENCE: 24

Ala Glu Glu Tyr Glu Phe Leu Thr Pro Val Glu Glu Ala Pro Lys
1               5                   10                  15

<210> SEQ ID NO 25
<211> LENGTH: 10
<212> TYPE: PRT
<213> ORGANISM: Artificial Sequence
<220> FEATURE:
<223> OTHER INFORMATION: Synthetic Peptidase inhibitor 16 biomarker
      peptide

<400> SEQUENCE: 25

Trp Asp Glu Glu Leu Ala Ala Phe Ala Lys
1               5                   10

<210> SEQ ID NO 26
<211> LENGTH: 9
<212> TYPE: PRT
<213> ORGANISM: Artificial Sequence
<220> FEATURE:
<223> OTHER INFORMATION: Synthetic Cadherin-2 (N-Cadherin) biomarker
      peptide

<400> SEQUENCE: 26

Gly Pro Phe Pro Gln Glu Leu Val Arg
1               5

<210> SEQ ID NO 27
<211> LENGTH: 11
<212> TYPE: PRT
<213> ORGANISM: Artificial Sequence
<220> FEATURE:
<223> OTHER INFORMATION: Synthetic Dipeptidyl peptidase 4 biomarker
      peptide

<400> SEQUENCE: 27

Trp Glu Tyr Tyr Asp Ser Val Tyr Thr Glu Arg
1               5                   10

<210> SEQ ID NO 28
<211> LENGTH: 8
<212> TYPE: PRT
<213> ORGANISM: Artificial Sequence
<220> FEATURE:
<223> OTHER INFORMATION: Synthetic extracellular superoxide dismutase
      [Cu-Zn] biomarker peptide

<400> SEQUENCE: 28

Val Thr Gly Val Val Leu Phe Arg
1               5
```

```
<210> SEQ ID NO 29
<211> LENGTH: 17
<212> TYPE: PRT
<213> ORGANISM: Artificial Sequence
<220> FEATURE:
<223> OTHER INFORMATION: Synthetic Thrombospondin-4 biomarker peptide

<400> SEQUENCE: 29

Asp Val Asp Ile Asp Ser Tyr Pro Asp Glu Glu Leu Pro Cys Ser Ala
1               5                   10                  15

Arg

<210> SEQ ID NO 30
<211> LENGTH: 13
<212> TYPE: PRT
<213> ORGANISM: Artificial Sequence
<220> FEATURE:
<223> OTHER INFORMATION: Synthetic receptor-type tyrosine-protein
      phosphatase mu biomarker peptide

<400> SEQUENCE: 30

Gly Phe Gly Pro Pro Ala Thr Asn Gln Phe Thr Thr Lys
1               5                   10
```

METHODS FOR DETECTION, STAGING, AND SURVEILLANCE OF COLORECTAL ADENOMAS AND CARCINOMAS

CROSS-REFERENCE TO RELATED APPLICATIONS

This patent application is a national stage application under 35 U.S.C. § 371 of International Application No. PCT/US2017/037045, filed Jun. 12, 2017, which claims the benefit of U.S. Provisional Patent Application No. 62/348,290, filed Jun. 10, 2016, all of which are incorporated herein by reference in their entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: 16-816-PRO_ST25_6-9-16.txt, date recorded: Jun. 9, 2016, file size 11 KB).

BACKGROUND OF THE INVENTION

Field of the Invention

This invention provides methods for detecting one or a plurality of protein biomarkers wherein the protein biomarkers are leucine-rich alpha-2-glycoprotein, peptidase inhibitor 16, CD44, cadherin 2, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, serum amyloid P component, vitamin D binding protein, complement factor I, superoxide dismutase 3, vitronectin, thrombospondin-4 and quiescin sulfhydryl oxidase 1. The invention further provides minimally invasive methods, reagents, diagnostic and prognostic markers useful for staging, prognosis and surveillance of cancerous or pre-cancerous colon lesions, and therapeutic intervention in individuals with colorectal cancers, or individuals who may be susceptible to developing colorectal cancers. Particular embodiments of the invention employ serum biomarkers that identify the clinical stage of cancerous or pre-cancerous lesions of the colon.

Description of Related Art

In 2016, approximately 135,000 new cases of colon and rectal cancers will be diagnosed and nearly 50,000 will die from this disease, making it the one of the most common causes of cancer related death in the United States. Siegel R L, Miller K D, Jemal A. Cancer statistics, 2016. CA: a cancer journal for clinicians. 2016; 66(1):7-30. doi: 10.3322/caac.21332. PubMed PMID: 26742998. Early diagnosis has a high survival rate but there is low adherence to the recommended screening guidelines with approximately 23 million United States citizens (30-40%) remaining unscreened. Winawer S J, Fischer S E, Levin B. Evidence-Based, Reality-Driven Colorectal Cancer Screening Guidelines: The Critical Relationship of Adherence to Effectiveness. JAMA: the journal of the American Medical Association. 2016; 315(19):2065-6. doi: 10.1001/jama.2016.3377. PubMed PMID: 27187294.

In the United States, the primary method of colorectal cancer prevention is early detection by screening colonoscopy. Winawer SJ, et al., supra. Recent studies assessing the risk-benefit of routine colon cancer screening/surveillance by colonoscopy in the United States indicate that repeated colonoscopy is burdensome on the healthcare system and has less benefit than expected for patients. Kruse GR, Khan SM, Zaslaysky AM, Ayanian JZ, Sequist TD. Overuse of colonoscopy for colorectal cancer screening and surveillance. J Gen Intern Med. 2015; 30(3):277-83. Austin GL, Fennimore B, Ahnen DJ. Can colonoscopy remain cost-effective for colorectal cancer screening? The impact of practice patterns and the Will Rogers phenomenon on costs. The American journal of gastroenterology. 2013; 108(3): 296-301. A recent study identified a 2% re-admittance rate due to complications from colonoscopy within one week of the procedure Ranasinghe I, Parzynski CS, Searfoss R, Montague J, Lin Z, Allen J, et al. Differences in Colonoscopy Quality Among Facilities: Development of a Post-Colonoscopy Risk-Standardized Rate of Unplanned Hospital Visits. Gastroenterology. 2016; 150(1): 103-13. In February 2016, Canadian health officials issued new colon cancer screening guidelines stating that low-risk asymptomatic patients without a family history of colorectal cancer should no longer be screened by colonoscopy. Boggs W. Canadian experts say 'no' to colonoscopy for colon cancer screening. Reuters (Internet). 2016 4/14/2016. Less invasive stool-based tests such as Fecal Occult Blood Tests or Fecal Immunochemical Tests (FOBT and FIT) were recommended.

The majority of colon cancers begin as a benign adenomatous polyp and through the sequential accumulation of genetic mutations, progress to invasive carcinomas (FIG. 1). Suehiro Y, Hinoda Y. Genetic and epigenetic changes in aberrant crypt foci and serrated polyps. Cancer Sci. 2008; 99(6):1071-6. Epub 2008/April 2004. doi: 10.1111/j.1349-7006.2008.00784.xCAS784 [pii]. PubMed PMID: 18384435; Fearon E R, Hamilton S R, Vogelstein B. Clonal analysis of human colorectal tumors. Science. 1987; 238 (4824):193-7. Epub 1987/10/09. PubMed PMID: 2889267. Biopsies of polyps identified during colonoscopy are evaluated by pathologists who determine if a polyp is cancerous. Colonoscopy cases diagnosed with non-cancerous polyps are classified by risk for developing cancer with recommendations for follow-up surveillance based on the projected risk.

The ability to accurately predict a colorectal tumor's localized progression remains largely unsolved in the field of colon cancer biology. While molecular genetics approaches have resulted in the development of tests that use gene arrays to predict risk for recurrence, they remain limited in their ability to predict lymph node involvement (stage 3) at the time of diagnosis. Maak M, Simon I, Nitsche U, Roepman P, Snel M, Glas A M, et al. Independent Validation of a Prognostic Genomic Signature (ColoPrint) for Patients With Stage II Colon Cancer. Ann Surg. 2013. Epub 2013/01/09. doi: 10.1097/SLA.0b013e31827c1180. PubMed PMID: 23295318. Imaging techniques used to identify stage 4 metastases (CT scans) have not been able to reliably identify the presence of lymph node invasion. Furthermore, regional lymph nodes are not adequately visualized by any of the imaging methods used during current patient work-up procedures (CT scan, MRI, PET/MRI), and resolving small affected lymph nodes, or partially affected lymph nodes, is unlikely even with future technological breakthroughs within these imaging fields.

Currently lymph node invasion can only be detected reliably by surgical resection and pathologic analysis of the lymph nodes. Up to 35% of colorectal surgery patients suffer from post-operative complications, which have been shown to be at higher risk for mortality, poor oncologic outcomes, additional complications, and worse quality of life. Artinyan A, Orcutt S T, Anaya D A, Richardson P, Chen G J, Berger D H. Infectious postoperative complications decrease long-term survival in patients undergoing curative surgery for colorectal cancer: a study of 12,075 patients. Annals of surgery. 2015; 261(3):497-505. doi: 10.1097/SLA.0000000000000854. PubMed PMID: 25185465. Localized surgical techniques such as endoscopic resection, that could reduce the incidence of patient morbidity, are possible if regional lymph node status is known.

Rectal cancers cause significant patient morbidity and mortality compared to colon cancers due to the sensitivity of the region being treated. The level of morbidity and mortality associated with rectal cancers is an ongoing concern during clinical management. The primary therapy for both colon and rectal cancers is surgery to remove the tumor(s). Some rectal cancer patients benefit from neoadjuvant treatment (prior to surgery) in the form of radiation and/or chemotherapy. However, not all patients will benefit from neoadjuvant therapy. Furthermore, the toll of the successive treatments, coupled with frequent need for a temporary ostomy (which must be removed by a second surgery after any adjuvant chemotherapy treatment), means that patients with rectal cancer sometimes refuse necessary treatments due to the toll it takes on daily health and lifestyle.

Thus, there is also a need in the art to accurately and reliable identify patients with rectal cancers who will benefit from neoadjuvant treatments. In particular, there is a need for methods to achieve consistent staging of patients' lymph node status before offering neoadjuvant treatment. Physicians who do not do any staging are often over treating patients, particularly if they have T1 or T2 tumors. Physicians who do stage a rectal cancer patient prior to treatment will often offer neoadjuvant treatment for any patient with a T3 or T4 tumor (without knowing anything about lymph node status). This is due to the likelihood of lymph node involvement when a primary tumor has grown further into the intestinal wall. However, this means that many patients are being over-treated, lengthening the amount of time a patient is undergoing therapy in addition to the pains of going through unnecessary chemotherapy and radiation.

SUMMARY OF THE INVENTION

This invention provides methods for detecting one or a plurality of protein biomarkers wherein the protein biomarkers are leucine-rich alpha-2-glycoprotein, peptidase inhibitor 16, CD44, cadherin 2, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, serum amyloid P component, vitamin D binding protein, complement factor I, superoxide dismutase 3, vitronectin, thrombospondin-4 and quiescin sulfhydryl oxidase 1. This invention further provides minimally invasive methods, reagents, diagnostic and prognostic markers useful for staging, prognosis and surveillance of colorectal cancers, and therapeutic intervention in individuals with colorectal cancers, or individuals who may be susceptible to developing colorectal cancers.

In one aspect, provided herein are methods for detecting one or a plurality of protein biomarkers in a biosample, the method comprising: assaying a biosample for one or a plurality of protein biomarkers, wherein the protein biomarkers are leucine-rich alpha-2-glycoprotein, peptidase inhibitor 16, CD44, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, and quiescin sulfhydryl oxidase 1; and detecting the level of one or a plurality of the protein biomarkers in the biosample.

In another aspect, provided herein are methods for detecting one or a plurality of protein biomarkers in a biosample, the method comprising: assaying a biosample for one or a plurality of protein biomarkers, wherein the protein biomarkers are leucine-rich alpha-2-glycoprotein, CD44, dipeptidyl peptidase 4, inter-alpha trypsin inhibitor, heavy chain H3, epidermal growth factor receptor; and detecting the level of one or a plurality of the protein biomarkers in the biosample.

In still another aspect, provided herein are methods for detecting one or a plurality of protein biomarkers in a biosample, the method comprising: assaying a biosample for one or a plurality of protein biomarkers, wherein the protein biomarkers are C-reactive protein, inter-alpha trypsin inhibitor, heavy chain H4, inter-alpha trypsin inhibitor, heavy chain H3, and quiescin sulfhydryl oxidase 1; and detecting the level of one or a plurality of the protein biomarkers in the biosample.

In some embodiments, provided herein are methods for detecting one or a plurality of protein biomarkers in a biosample, the method comprising: assaying a biosample for one or a plurality of protein biomarkers, wherein the protein biomarkers are C-reactive protein, CD44, epidermal growth factor receptor, and quiescin sulfhydryl oxidase 1; and detecting the level of one or a plurality of the protein biomarkers in the biosample.

In other embodiments, provided herein are methods for detecting one or a plurality of protein biomarkers in a biosample, the method comprising: assaying a biosample for one or a plurality of protein biomarkers, wherein the protein biomarkers are coagulation factor V, C-reactive protein, peptidase inhibitor 16, inter-alpha trypsin inhibitor, heavy chain H4, and leucine-rich alpha-2-glycoprotein; and detecting the level of one or a plurality of the protein biomarkers in the biosample.

In still other embodiments, provided herein are methods for detecting one or a plurality of protein biomarkers in a biosample, the method comprising: assaying a biosample for one or a plurality of protein biomarkers, wherein the protein biomarkers are C-reactive protein and peptidase inhibitor 16; and detecting the level of one or a plurality of the protein biomarkers in the biosample.

In exemplary, non-exclusive embodiments, the disclosure provides serum biomarkers for distinguishing between normal tissue, low-risk adenomas, and high-risk adenomas (also known as an advanced adenoma).

In other exemplary, non-exclusive embodiments, the disclosure provides serum biomarkers for distinguishing between normal tissue, low-risk adenomas, and villous adenomas;

In still other exemplary, non-exclusive embodiments, the disclosure provides serum biomarkers for distinguishing between local (stages 1 and 2) or regional (stage 3) colorectal cancers.

In further exemplary, non-exclusive embodiments, the disclosure provides serum biomarkers for detecting growing adenomas.

In yet further exemplary, non-exclusive embodiments, the disclosure provides serum biomarkers for identifying the recurrence of a cancerous or pre-cancerous colon lesion following a polypectomy, colectomy, or other therapeutic intervention.

Some exemplary, non-exclusive embodiments of the disclosure provide gender-specific serum biomarkers for distinguishing between normal tissue, low-risk adenomas, and advanced adenomas.

Other exemplary, non-exclusive embodiments provide specific serum biomarkers for identifying the presence of rectal polyps in a subject.

In some aspects, the disclosure provides serum biomarkers and methods for identifying colorectal cancer in a subject by comparing the level of the one or a plurality of the protein biomarkers in the biosample to a reference level of said one or a plurality of protein biomarkers.

In particular embodiments the biosample is from a cancerous or pre-cancerous colon lesion. In other embodiments the method further comprises identifying the stage of the cancerous or precancerous colon lesion by comparing the level of the one or a plurality of the protein biomarkers in the biosample to a reference level of said one or a plurality of protein biomarkers in stage 0, stage 1, stage 2, stage 3, or stage 4 carcinomas.

In particular embodiments, the biosample is from a cancerous or pre-cancerous colon lesion. In other embodiments the method further comprises identifying the lesion as a high-risk adenoma, advanced adenoma, a low-risk adenoma, or colorectal carcinoma by comparing the level of the one or a plurality of the protein biomarkers in the biosample to a reference level of said one or a plurality of protein biomarkers in low-risk adenoma, high-risk adenoma and colorectal carcinoma.

In particular embodiments, the biosample is from a cancerous or precancerous colon lesion. In other embodiments, the method further comprises identifying the recurrence of a cancerous or pre-cancerous colon lesion following a polypectomy (termed post-polypectomy herein) or a surgical resection to remove colorectal cancer when the level of one or a plurality of the protein biomarkers is different than the level detected in a cancerous or pre-cancerous colon lesion pre-polypectomy.

In embodiments, the disclosure provides a method of detecting one or a plurality of protein biomarkers in a biosample comprising: selecting one or more detectably labeled synthetic peptides with homology to one or a plurality of the protein biomarkers; combining the detectably labeled synthetic peptides with the biosample; and subjecting the combination to a physical separation method.

"Homology" as used herein refers to a nucleic acid, peptide, amino acid, or protein sequence with identity to a nucleic acid or amino acid sequence of a biomarker. In particular embodiments, a nucleic acid, peptide, amino acid, or protein sequence with homology to a nucleic acid or amino acid sequence of a biomarker has about 80%, 85%, 90%, 95%, or greater identity to all or a portion of the sequence of the biomarker.

In some embodiments, the physical separation method of the disclosure is liquid chromatography and the synthetic peptides are isotopically labeled.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

BRIEF DESCRIPTION OF THE DRAWINGS

FIG. 5 further illustrates the demographics of patients enrolled in the examples of the disclosure. Approximately equal numbers of males and females were enrolled. The age range of patients was between 30 and 88 years with an approximate median age of 60 years. Most patients with polyps had 1-2 polyps, and 71 of the polyp-bearing patients had advanced adenomas. The majority of cancer cases were localized to the intestinal wall (stages 1&2) while 12 cases were regional (stage 3). Among these non-metastatic cases, the majority of reported CEA levels were at normal levels of less than 2.5 ng/mL.

FIG. 7 shows a schematic of the calculation of the pre-/post-polypectomy ratios The pre-/post-polypectomy ratios are a ratio of ratios (where each individual ratio is referred to herein as "relative ratio-to-reference standard data"). First the ratio of each biological sample is taken compared to the internal, heavy-labeled reference standard. Second, the ratios are used to calculate the final pre-/post-polypectomy ratio. Proteins upregulated in colon adenomas or carcinomas should show a pre-/post-polypectomy ratio that is also upregulated. Proteins downregulated in colon adenomas or carcinomas should have a pre-/post-polypectomy ratio that is also downregulated.

In FIG. 25B, each bar represents the pre-/post-polypectomy ratio for a single patient. Because PI16 is typically downregulated, pre-/post-ratios below 1 are considered reversions toward normal protein expression levels after polypectomy.

In FIG. 26B, each bar represents the pre-/post-polypectomy ratio for a single patient. Because CRP is typically upregulated, pre-/post-ratios above 1 are considered reversions toward normal protein expression levels after polypectomy. In this case, most of the significant reversions occurred in advanced adenoma cases.

DETAILED DESCRIPTION OF THE INVENTION

Figure 1:
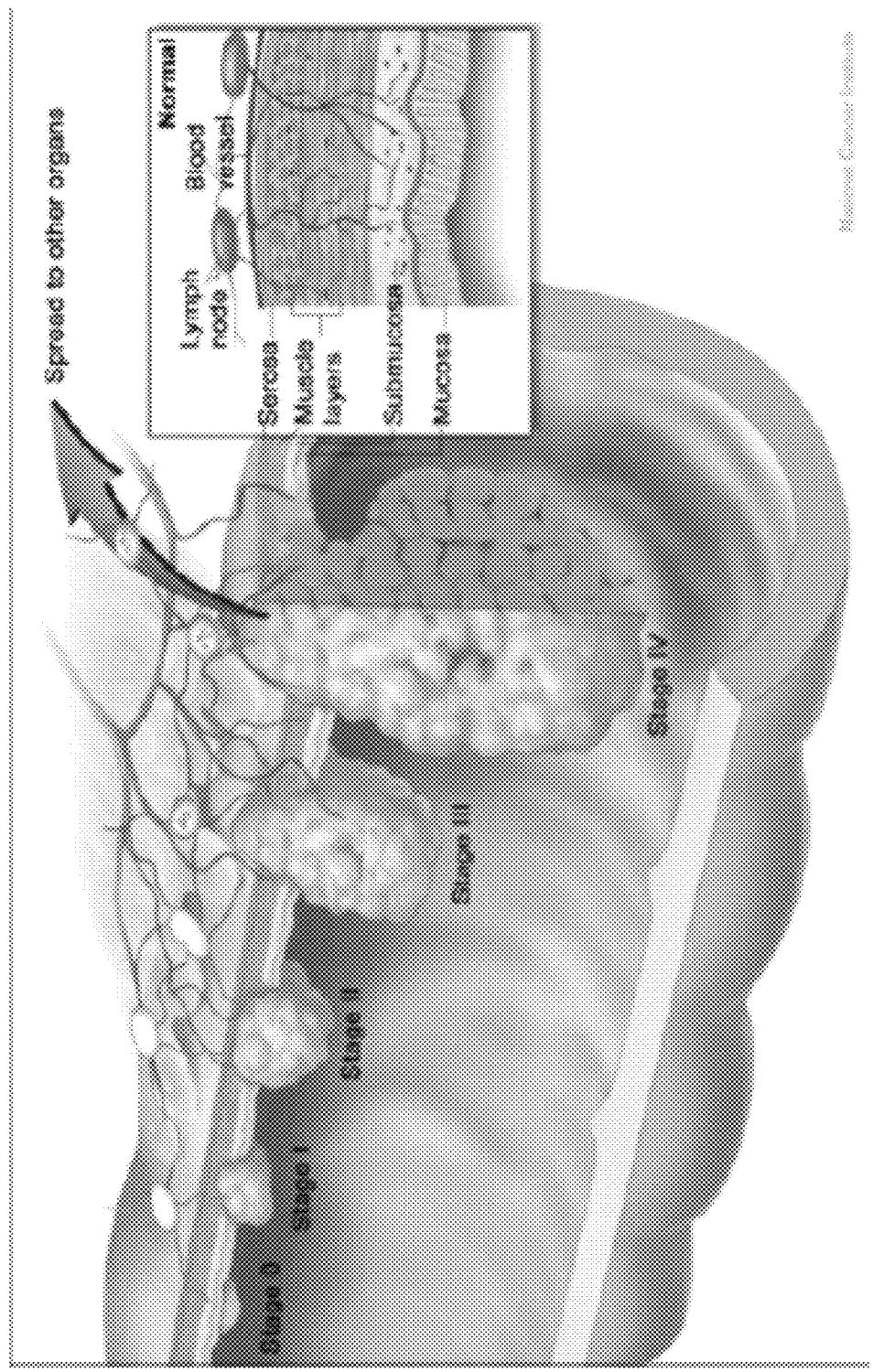
FIG. 1 illustrates an image from the United States National Cancer Institute identifying the generalized stages of colorectal cancer. Stage 0 is a pre-cancerous polyp, often termed an adenoma. Stages 1 & 2 are cancerous but have not invaded regional lymph nodes. Stage 3 is the point at which regional lymph nodes are infected. Stage 4 is metastatic cancer.

All publications, patents and patent applications cited herein are hereby expressly incorporated by reference for all purposes.

Provided herein are non-invasive methods for diagnosis and prognosis, in particular staging, typing or predicting outcome in subjects with cancerous or pre-cancerous lesions of the colon. A "lesion" as used herein refers to an abnormal region of the colon, and includes dysplasia, aberrant crypts, as well as benign or cancerous polyps.

A "polyp" as used herein refers to a polyp present in any of the four stages of colorectal cancer, or to a polyp of a precancerous condition. As used herein, "colorectal cancer" refers to a condition comprised of any of the 4 stages, ranging from stage 1 to stage 4, classified by the American Joint Committee on Cancer (AJCC) according to the TNM system (which evaluates histological properties (T), tumor presence in nearby lymph nodes (N), and metastatic spread (M)). Gunderson L L, Jessup J M, Sargent D J, Greene F L, Stewart A K. Revised T N categorization for colon cancer based on national survival outcomes data. Journal of clinical oncology: official journal of the American Society of Clinical Oncology. 2010; 28(2):264-71. Epub 2009/12/02. doi: 10.1200/JC0.2009.24.0952. PubMed PMID: 19949014; PubMed Central PMCID: PMC2815715; Greene F L. The American Joint Committee on Cancer: updating the strategies in cancer staging. Bulletin of the American College of Surgeons. 2002; 87(7):13-5. Epub 2007/03/29. PubMed PMID: 17387902. (Table 1.)

TABLE 1

TNM staging system by the American Joint Committee on Cancer (AJCC), 6th Edition

| AJCC Stage | TNM Stage | TNM staging criteria |
| --- | --- | --- |
| Stage 0 | Tis N0 M0 | Tis: Tumor is confined to mucosal layer. Cancer-in-situ |
| Stage I | T1 N0 M0 | T1: Tumor invades submucosa |
| Stage I | T2 N0 M0 | T2: Tumor invades muscle layer |
| Stage II-A | T3 N0 M0 | T3: Tumor invades serosa or beyond without metastasis to other organs |
| Stage II-B | T4 N0 M0 | T4: Tumor invades adjacent organs or perforates the visceral peritoneum |
| Stage III-A | T1-2 N1 M0 | N1: Metastasis to 1-3 lymphnodes. T1 or T2 |
| Stage III-B | T3-4 N1 M0 | N1, and T3 or T4 |
| Stage III-C | any T, N2 M0 | N2: Metastasis to 4 or more regional lymphnodes. Any T |
| Stage IV | any T, any N, M1 | M1: Distant metastases, Any T, any N |

A "pre-cancerous condition" as used herein refers to a patient with a pre-invasive, pre-metastatic lesion that disposes a person to colon cancer. Examples include dysplasia, the presence of aberrant crypts, and the presence of adenomas. The AJCC formally characterizes adenomas as pre-cancerous polyps ("Stage 0") by a T-stage of "Tis", where the "is" stands for carcinoma in situ. Tis adenomas are characterized by a polyp sitting in the large intestinal mucosa, with no invasion of the intestinal wall. (Table 1.)

"Normal tissue" as used herein refers to tissue of the colon and/or rectum that looks healthy in appearance by colonoscopy and/or histopathology.

"Advanced adenoma" as used herein refers to a polyp or grouping of pre-cancerous polyps within a patient that presents high-risk for developing into cancer.

"Villous adenoma" as used herein refers to a type of polyp with a specific histopathology that is particularly prone to becoming cancerous. It is diagnosed by microscopy and often has a "cauliflower"-like appearance. Tubular adenomas are a shape of adenoma that can be seen by colonoscopy without the need for histopathology. Tubulovillous refers to an adenoma with a tubular shape that under a microscope has a villous pathology.

"Local" colorectal cancer as used herein refers to TNM stage 1 and TNM stage 2 colorectal cancer. Specifically, these are cancers that have penetrated the large intestinal wall anywhere from the mucosa to the serosa (FIG. 2).

Figure 2:
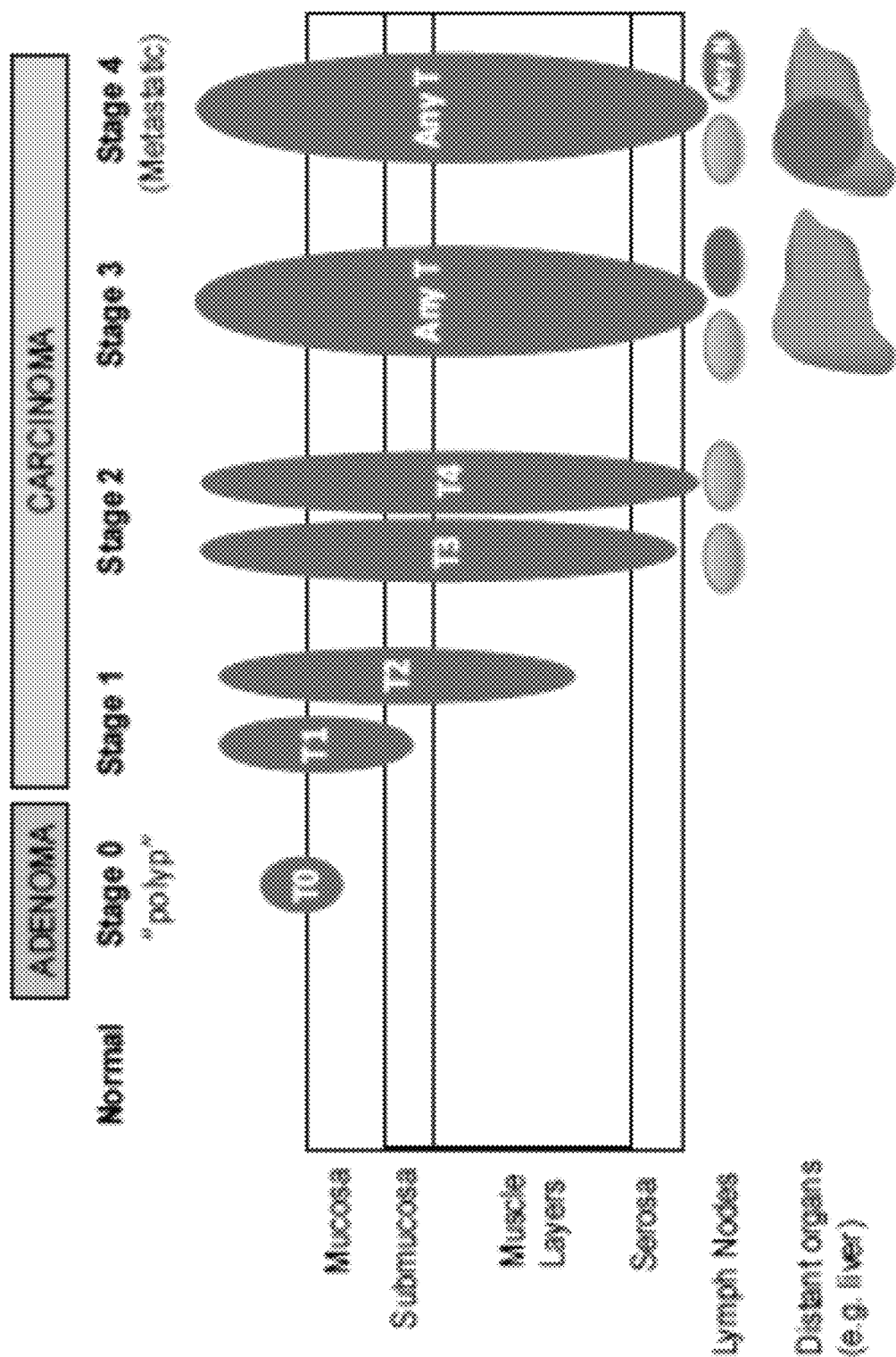
FIG. 2 shows colorectal cancer staging with an emphasis on localization of polyp growth in the tissues of the colon. The epithelial layer is categorized into 4 different tissue layers: Mucosa, Submucosa, Muscle tissue, and Serosa. Just beyond the exterior of the colon and rectal wall are adjacent lymph nodes followed by the other tissues of the body that can be affected by colon tumorigenesis. The first stage of colon cancer is stage 0, where a polyp forms on the intestinal mucosa. This stage is not cancerous. All other stages are called carcinomas, which are cancerous.
Figure 3:
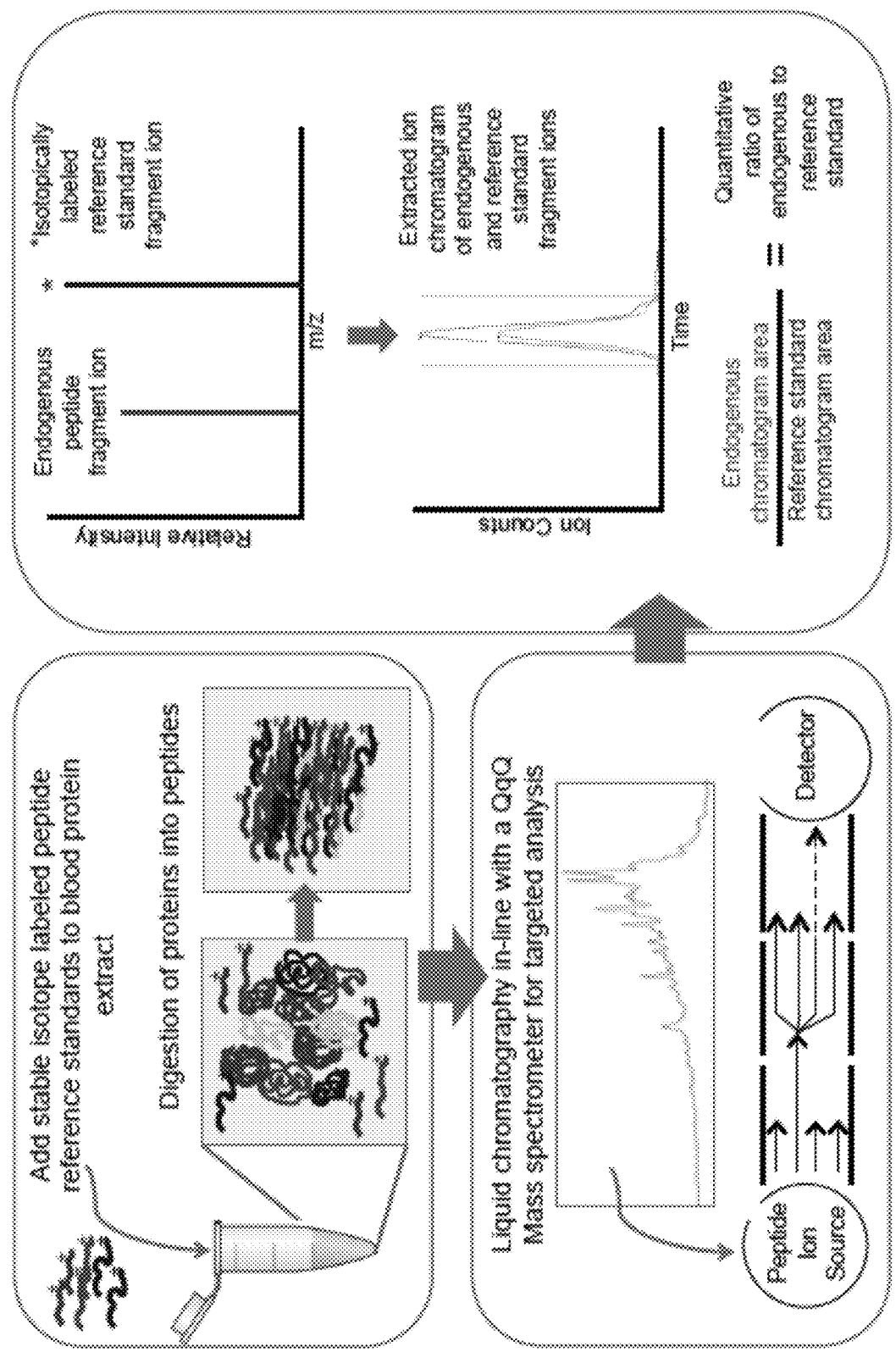
FIG. 3 is a schematic illustrating the workflow of a targeted quantitative proteomics experiment. Stable isotope labeled reference standards are spiked into a protein extract prior to enzymatic digestion. These standards match the endogenous peptide sequence of a target protein of interest but contain one heavy stable isotope labeled amino acid. Peptides are chromatographically separated by reversed-phase chromatography followed by analysis in-line with a triple quadrupole mass spectrometer (QQQ-MS) where targeted precursor and fragment ion masses (transitions) are selected. Two sensitive quadrupole mass filters are used to select the precursor (Q1) and fragment peptide ions (Q3) of interest, with q2 used as a collision cell. Quantification of the heavy and light peptides is achieved using extracted ion chromatogram areas. A ratio of endogenous chromatogram area to reference standard chromatogram area is used to obtain the relative ratio. The relative ratio to reference standard can be compared across biological samples to determine relative differential expression among biological groups.

"Regional" colorectal cancer as used herein refers to colorectal cancers that have invaded any number of regions of the large intestinal wall and have infected lymph nodes localized just outside the intestinal wall (FIG. 2).

In some embodiments, methods are provided for detecting one or a plurality of protein biomarkers comprising: (a) assaying a biosample for one or a plurality of protein biomarkers, wherein the protein biomarkers are leucine-rich alpha-2-glycoprotein, peptidase inhibitor 16, CD44, cadherin 2, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, serum amyloid P component, vitamin D binding protein, complement factor I, superoxide dismutase 3, vitronectin, thrombospondin-4 and quiescin sulfhydryl oxidase 1; and (b) detecting the level of one or a plurality of the protein biomarkers in the biosample.

In other embodiments the method further comprises identifying the stage of a cancerous or precancerous colon lesion by comparing the level of the one or a plurality of the protein biomarkers in the biosample to a reference level of said one or a plurality of protein biomarkers in stage 0, stage 1, stage 2, stage 3, or stage 4 carcinomas.

As used herein, "stage" or "staging" refers to one or more clinical classification systems used to describe the progression and severity of cancerous or pre-cancerous lesions in the colon. Colorectal tumor stage describes the location and level of tumor invasion into the intestinal wall, regional lymph nodes, and adjacent or distant tissues.

A nonexclusive example of a tumor staging system used in connection with embodiments of the present disclosure is the TNM system (See Gunderson L L, et al.; Greene, F L, supra) (Table 1). In the TNM system, stages 1 and 2 have T-stages of T1 or T2 and T3 or T4, respectively, with no invasion of lymph nodes or metastasis (N0 M0). Stage 1 lesions have passed into the submucosa and possibly the muscle layer. Stage 2 lesions have invaded the serosa and may have grown through the intestinal wall but has not invaded any nearby lymph nodes. Stage 3 lesions are very complex with three sub classifications, but can broadly be characterized by having any T-stage and the invasion of some or many nearby lymph nodes. Stage 4, constituting malignant, metastatic colon cancer, can have any T or any N classification but has metastasized other organs, most commonly the liver. (Table 1.)

In embodiments of the disclosure, "staging" of tumors is accomplished by classifying them in relative categories, such as advanced adenomas versus low risk adenomas. In other embodiments, staging is accomplished by classifying tumors into advanced adenomas versus a category that pools low risk adenomas and normal tissue.

In other embodiments, staging is accomplished by classifying tumors into categories relating to the pathophysiology or anatomy of the tumors. For example, staging is accomplished by classifying tumors into villous or tubulovillous adenomas versus low risk adenomas (without villous or tubulovillous characteristics), or versus normal tissue. Alternatively, staging is accomplished by classifying tumors based on growth characteristics, such as growing adenomas, versus static or regressing adenomas.

In still further embodiments, staging is accomplished by classifying tumors based on their localization in a subject. Thus, in some embodiments local (stages 1 and 2) tumors are distinguished from regional (stage 3) tumors in colorectal cancer.

Those skilled in the art will recognize alternative staging systems useful in connection with the presently disclosed methods. Examples of other staging systems include the Duke's classification system (Dukes, C. E., *Journal of Pathological Bacteriology* 1932, 35:323), and the Astler-Coller classification system (Astler V. B. and Coller F. A., *Ann Surg* 1954, 139:846).

In some embodiments, methods are provided for analyzing the clinical grade of lesions in the colon of a subject. As used herein, "tumor grade" refers to a histological assessment that describes the degree to which the tumor cells have differentiated into normal colon tissue cells. Current tumor grade classifications are part of the TNM guidelines of colon cancer classification and range from G1 to G4. Cells rated G1 histologically look the most like healthy colon tissue cells. G2 rated cells are moderately differentiated, G3 rated cells are poorly differentiated, and G4 cells are undifferentiated. Higher-grade cells tend to grow more rapidly and can influence the method of cancer treatment. In some embodiments, the protein biomarkers and methods provided herein can be used to assess the level of cellular differentiation (tumor grade) and influence patient treatment strategies.

In some embodiments, the methods involve detecting the level of one or a plurality of protein biomarkers a in a subject and then comparing the level to a reference level or range. Typically, the reference level is representative of a protein biomarker in a large number of persons or tissues with colon cancer and whose clinical prognosis data are available, as measured using a tissue sample or biopsy or other biological sample such as a cell, serum or blood.

In some embodiments, methods are provided for detecting one or a plurality of protein biomarkers in a biosample, the method comprising: assaying a biosample for one or a plurality of protein biomarkers, wherein the protein biomarkers are leucine-rich alpha-2-glycoprotein, peptidase inhibitor 16, CD44, cadherin 2, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, serum amyloid P component, vitamin D binding protein, complement factor I, superoxide dismutase 3, vitronectin, thrombospondin-4 and quiescin sulfhydryl oxidase 1; and detecting the level of one or a plurality of the protein biomarkers in the biosample. In other embodiments, the method further comprises identifying a cancerous or pre-cancerous colon lesion as a high-risk (advanced) adenoma, a low-risk adenoma, or colorectal carcinoma by comparing the level of the one or a plurality of the protein biomarkers in the biosample to a reference level of said one or a plurality of protein biomarkers in low-risk adenoma, high-risk adenoma and colorectal carcinoma.

Risk of developing colorectal cancer is classified as "low" or "high" (Table 2). Low-risk patients are recommended for follow-up screening by colonoscopy within 5-10 years. Patients with polyps considered high risk are recommended for follow-up screening by colonoscopy within 3-5 years. High-risk polyps are also referred to as "advanced adenomas." Patients with a high risk for developing colorectal cancer have one or several of the following characteristics: a clinical or familial history of colorectal cancer; a polyp greater than 10 millimeters; 3-10 tubular adenomas, one or more adenoma with villous properties; or a serrated adenoma with dysplasia. Patients with a low risk for developing colorectal cancer have: no polyps at colonoscopy; polyps with hyperplastic properties unless serrated or greater than 10 millimeters; less than 3 tubular adenomas smaller than 10 millimeters; or sessile serrated polyps with no dysplasia.

TABLE 2

Polyp risk factors of the eventual development of colorectal cancer.

| | |
|---|---|
| LOW RISK FACTORS | A screening normal colonoscopy (no polyps/biopsies collected for pathology analsysis) |
| | Hyperplastic polyps (especially those that are distal), Exceptions; Hyperplastic polyps that are serrated or those that are greater than 10 mm |
| | 1-2 tubular adenomas less than 10 mm |
| | 1-2 sessile serrated polyps less than 10 mm and with no apparent dysplasia |
| HIGH RISK FACTORS | Any polyp that is greater than 10 mm |
| | 3-10 tubular adenomas less than 10 mm |
| | One or more villous adenoma |
| | Any adenoma with high-grade dysplasia |
| | Sessile serrated polyp(s) ≥10 mm |
| | Sessile serrated polyp with dysplasia |
| | Traditional serrated adenoma |
| | Known clinical history of colonic polyps or a familial history and colon polyps identified at the time of colonoscopy |

In further embodiments, the disclosure provides methods of identifying colorectal cancer in a subject by comparing the level of the one or a plurality of the protein biomarkers in the biosample to a reference level of said one or a plurality of protein biomarkers.

In some embodiments, methods are provided for detecting one or a plurality of protein biomarkers in a biosample, the method comprising: assaying a biosample for one or a plurality of protein biomarkers, wherein the protein biomarkers comprise leucine-rich alpha-2-glycoprotein, peptidase inhibitor 16, CD44, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, and quiescin sulfhydryl oxidase 1.

In other embodiments, methods are provided for detecting one or a plurality of protein biomarkers in a biosample, the method comprising: assaying a biosample for one or a plurality of protein biomarkers, wherein the protein biomarkers comprise leucine-rich alpha-2-glycoprotein, CD44, dipeptidyl peptidase 4, inter-alpha trypsin inhibitor, heavy chain H3, epidermal growth factor receptor.

In further embodiments, the disclosure provides methods of identifying advanced adenomas, low risk adenomas, or normal tissue in a subject. In some embodiments, identifying the advanced adenomas, low risk adenomas, or normal tissue in a subject comprises detecting the level of one or a plurality of the protein biomarkers, wherein the protein biomarkers comprise C-reactive protein and epidermal growth factor receptor.

In yet further embodiments, the disclosure provides methods of identifying tubulovillous adenomas, low risk adenomas, or normal tissue in a subject. In some embodiments, identifying the tubulovillous adenomas, low risk adenomas, or normal tissue in a subject comprises detecting the level of one or a plurality of the protein biomarkers, wherein the protein biomarkers comprise C-reactive protein, inter-alpha trypsin inhibitor, heavy chain H4, inter-alpha trypsin inhibitor, heavy chain H3, and quiescin sulfhydryl oxidase 1.

In certain embodiments, the disclosure provides methods of identifying local (stages 1 and 2) or regional (stage 3) colorectal cancer in a subject. In embodiments, identifying local (stages 1 and 2) or regional (stage 3) colorectal cancer in a subject comprises detecting the level of one or a plurality of the protein biomarkers, wherein the protein biomarkers comprise C-reactive protein, CD44, epidermal growth factor receptor, and quiescin sulfhydryl oxidase 1.

In other embodiments, the disclosure provides methods of identifying growing adenomas in a subject. In embodiments, identifying growing adenomas in a subject comprises detecting the level of one or a plurality of the protein biomarkers, wherein the protein biomarkers comprise coagulation factor V, C-reactive protein, peptidase inhibitor 16, inter-alpha trypsin inhibitor, heavy chain H4, and leucine-rich alpha-2-glycoprotein.

In still other embodiments, the method further comprises identifying the recurrence of a cancerous or pre-cancerous colon lesion following a polypectomy when the level of one or a plurality of the protein biomarkers is different than the level detected in a cancerous or pre-cancerous colon lesion pre-polypectomy. In some embodiments, identifying the recurrence of a cancerous or pre-cancerous colon lesion following a polypectomy comprises detecting the level of one or a plurality of the protein biomarkers, wherein the protein biomarkers comprise C-reactive protein and peptidase inhibitor 16.

In some embodiments, the method comprises identifying advanced adenomas, low risk adenomas, or normal tissue in a female subject. In embodiments, identifying advanced adenomas, low risk adenomas, or normal tissue in a female subject comprises detecting the level of one or a plurality of protein biomarkers, wherein the protein biomarkers comprise coagulation factor V, CD44, and epidermal growth factor receptor.

In other embodiments, the method comprises identifying advanced adenomas, low risk adenomas, or normal tissue in a male subject. In embodiments, identifying advanced adenomas, low risk adenomas, or normal tissue in a male subject comprises detecting the level of one or a plurality of protein biomarkers, wherein the protein biomarkers comprise C-reactive protein, peptidase inhibitor 16, inter-alpha trypsin inhibitor, heavy chain H4, and complement factor I.

In further embodiments, the method comprises identifying the presence of rectal polyps in a subject by comparing the level of one or a plurality of protein biomarkers in a biosample to a reference level of the one or a plurality of protein biomarkers. In certain embodiments, identifying the presence of rectal polyps in a subject comprises detecting the level of one or a plurality of protein biomarkers, wherein the protein biomarkers comprise peptidase inhibitor 16, CD44, inter-alpha trypsin inhibitor, heavy chain H3, and quiescin sulfhydryl oxidase 1.

One of skill in the art would understand the parameters for determining the intervals for which surveillance of the colon should be performed based on for example, family history of colorectal cancer or polyps and stage of resected polyp or lesion. In particular embodiments, the biosample for surveillance is collected within 1 month, 2 months, 3 months, 4 months, 5 months, or 6 months post-polypectomy. In other embodiments, the biosample is collected within one year or two years post-polypectomy.

Inter-alpha-trypsin inhibitors, heavy chain H3 (ITIH3) and heavy chain 4, isoform 1 (ITIH4) are provided as biomarkers useful to practice the present methods. The inter-alpha trypsin inhibitors are involved in the covalent binding and stabilization of hyaluronic acid on the extracellular matrix. Chen L, Mao S J, McLean L R, Powers R W, Larsen W J. Proteins of the inter-alpha-trypsin inhibitor family stabilize the cumulus extracellular matrix through their direct binding with hyaluronic acid. The Journal of biological chemistry. 1994; 269(45):28282-7. Epub 1994/11/11. PubMed PMID: 7525572. Hyaluronan is a large epithelial glycosaminoglycan complex known to increase in size with the growth of colonic polyps and tumors [14]. In addition, ITIH3 has previously been identified as upregulated in the plasma of human gastric cancer patients and has a predicted role in the prevention of metastasis and tumor invasion activities in colon cancer. Misra S, Hascall V C, Berger F G, Markwald R R, Ghatak S. Hyaluronan, CD44, and cyclooxygenase-2 in colon cancer. Connective tissue research. 2008; 49(3):219-24. Epub 2008/07/29. doi: 10.1080/03008200802143356. PubMed PMID: 18661347; Chong P K, Lee H, Zhou J, Liu S C, Loh M C, Wang T T, et al. ITIH3 is a potential biomarker for early detection of gastric cancer. Journal of proteome research. 2010; 9(7): 3671-9. Epub 2010/06/03. doi: 10.1021/pr100192h. PubMed PMID: 20515073.

In addition, epidermal growth factor receptor (EGFR) is provided as a biomarker useful to practice the present methods. EGFR is implicated in poor tumor prognosis. Lieto E, Ferraraccio F, Orditura M, Castellano P, Mura A L, Pinto M, et al. Expression of vascular endothelial growth factor (VEGF) and epidermal growth factor receptor (EGFR) is an independent prognostic indicator of worse outcome in gastric cancer patients. Annals of surgical oncology. 2008; 15(1):69-79. Epub 2007/09/27. doi: 10.1245/s10434-007-9596-0. PubMed PMID: 17896140.

Certain enzymes implicated in the inflammation response are provided as biomarkers useful to practice the present methods. Leucine-rich alpha-2-glycoprotein (LRG1) is thought to play a role in acute phase response and inflammation. Hsu S J, Nagase H, Balmain A. Identification of Fetuin-B as a member of a cystatin-like gene family on mouse chromosome 16 with tumor suppressor activity. Genome/National Research Council Canada=Genome/Conseil national de recherches Canada. 2004; 47(5):931-46. Epub 2004/10/23. doi: 10.1139/g04-043. PubMed PMID: 15499407; Shirai R, Hirano F, Ohkura N, Ikeda K, Inoue S. Up-regulation of the expression of leucine-rich alpha(2)-glycoprotein in hepatocytes by the mediators of acute-phase response. Biochemical and biophysical research communications. 2009; 382(4):776-9. Epub 2009/03/28. doi: 10.1016/j.bbrc.2009.03.104. PubMed PMID: 19324010. LRG1 has shown upregulation in multiple mouse studies and has been shown to be upregulated in the plasma of human colon cancer patients. Chong, P K, et al., Shirai, et al., supra; Ladd J J, Busald T, Johnson M M, Zhang Q, Pitteri S J, Wang H, et al. Increased plasma levels of the APC-interacting protein MAPRE1, LRG1, and IGFBP2 preceding a diagnosis of colorectal cancer in women. Cancer Prev Res (Phila). 2012; 5(4):655-64. Epub 2012/01/27. doi: 10.1158/1940-6207.CAPR-11-0412. PubMed PMID: 22277732; PubMed Central PMCID: PMC3419141; Hung K E, Faca V, Song K, Sarracino D A, Richard L G, Krastins B, et al. Comprehensive proteome analysis of an Apc mouse model uncovers proteins associated with intestinal tumorigenesis. Cancer Prev Res (Phila). 2009; 2(3):224-33. Epub 2009/02/26. doi: 10.1158/1940-6207.CAPR-08-0153. PubMed PMID: 19240248; PubMed Central PMCID: PMC2874864.

LRG1 is an acute phase response protein that is upregulated in the blood of humans and murine models of colon cancer. Chong, P K, et al., Ladd, J J, et al., supra; Ivancic M M, Huttlin E L, Chen X, Pleiman J K, Irving A A, Hegeman A D, et al. Candidate serum biomarkers for early intestinal cancer using 15N metabolic labeling and quantitative proteomics in the ApcMin/+ mouse. Journal of proteome research. 2013; 12(9):4152-66. Epub 2013/08/09. doi: 10.1021/pr400467c. PubMed PMID: 23924158; PubMed Central PMCID: PMC3792563. Studies have shown that this protein is also upregulated in the serum of patients with ulcerative colitis, suggesting that LRG1 may also be a systemic indicator of intestinal disease. Serada S, Fujimoto M, Terabe F, Iijima H, Shinzaki S, Matsuzaki S, et al. Serum leucine-rich alpha-2 glycoprotein is a disease activity biomarker in ulcerative colitis. Inflammatory bowel diseases. 2012; 18(11):2169-79. Epub 2012/03/01. doi: 10.1002/ibd.22936. PubMed PMID: 22374925. One study showed that LRG1 promotes endothelial cell formation via signaling by the TGF-β pathway through interactions with ALK1-SMAD 1, 5, and 8, thus inducing an angiogenic state. Wang X, Abraham S, McKenzie J A, Jeffs N, Swire M, Tripathi V B, et al. LRG1 promotes angiogenesis by modulating endothelial TGF-beta signalling. Nature. 2013; 499(7458):306-11. Epub 2013/07/23. doi: 10.1038/nature12345. PubMed PMID: 23868260; PubMed Central PMCID: PMC3836402. Angiogenesis, one of the fundamental attributes of tumor invasion and metastasis, can be triggered very early in tumor formation. Hanahan D, Weinberg R A. Hallmarks of cancer: the next generation. Cell. 2011; 144(5):646-74. Epub 2011/03/08. doi: 10.1016/j.cell.2011.02.013. PubMed PMID: 21376230. Other studies have shown that circulating levels of LRG1 in blood plasma may be useful to diagnose colorectal cancer and identify regional tumor localization within the colon, recto-sigmoid junction, and the rectum (Surinova, S. et al., EMBO Mol Med 2015, 7, 1153-1165; Surinova, S. et al., EMBO Mol Med 2015, 7, 1166-1178).

C-reactive protein (CRP) is also provided as one of the biomarkers useful to practice the present methods. CRP is an annular (ring-shaped), pentameric protein found in blood plasma, and the levels of which rise in response to inflammation. CRP is an acute-phase protein of hepatic origin that increases following interleukin-6 secretion by macrophages and T cells.

Coagulation factor V (F5) is also provided as one of the biomarkers useful to practice the present methods. F5 is a cofactor for activated coagulation factor X (Xa) which assists in cleaving prothrombin to form an active thrombin protein which is vital for blood clotting. Davie E W, Fujikawa K, Kisiel W. The coagulation cascade: initiation, maintenance, and regulation. Biochemistry. 1991; 30(43):10363-70. Epub 1991/10/29. PubMed PMID: 1931959. Perturbation in hemostasis is a commonly observed side effect of cancer, with venous thromboembolism as a documented complication in colon cancer patients. Falanga A, Marchetti M, Vignoli A. Coagulation and cancer: biological and clinical aspects. Journal of thrombosis and haemostasis: JTH. 2013; 11(2):223-33. Epub 2013/01/03. doi: 10.1111/jth.12075. PubMed PMID: 23279708; Alcalay A, Wun T, Khatri V, Chew H K, Harvey D, Zhou H, et al. Venous thromboembolism in patients with colorectal cancer: incidence and effect on survival. Journal of clinical oncology: official journal of the American Society of Clinical Oncology. 2006; 24(7):1112-8. Epub 2006/03/01. doi: 10.1200/JCO.2005.04.2150. PubMed PMID: 16505431. Coagulants such as fibrinogen, F5, and other coagulation factors have increased levels in colon cancer patients. Paspatis G A, Sfyridaki A, Papanikolaou N, Triantafyllou K, Livadiotaki A, Kapsoritakis A, et al. Resistance to activated protein C, factor V leiden and the prothrombin G20210A variant in patients with colorectal cancer. Pathophysiology of haemostasis and thrombosis. 2002; 32(1):2-7. Epub 2002/09/06. doi: 57282. PubMed PMID: 12214157; Vossen C Y, Hoffmeister M, Chang-Claude J C, Rosendaal F R, Brenner H. Clotting factor gene polymorphisms and colorectal cancer risk. Journal of clinical oncology: official journal of the American Society of Clinical Oncology. 2011; 29(13):1722-7. Epub 2011/03/23. doi: 10.1200/JCO.2010.31.8873. PubMed PMID: 21422408. In addition, F5 is most known for its association with the Factor V Leiden coagulation disease. Factor V Leiden is caused by a single nucleotide polymorphism (SNP) involving an R506Q mutation. This mutation reduces the ability of the activated protein C anticoagulant protein from binding F5. Normal interactions between activated protein C and F5 lead to the degradation of F5. However, in the absence of this interaction, F5 levels increase and cause excessive coagulation. Patients homozygous for the factor V Leiden mutation show a nearly 6-fold increased risk for colorectal cancer. Vossen, C Y, et al., supra. A recent biomarker study has indicated that F5 may be a blood plasma marker to distinguish localized versus metastatic colorectal cancers (Surinova, S. et al., *EMBO Mot Med* 2015, 7, 1153-1165).

Dipeptidyl peptidase-4 (DPP4) can also be used as a biomarker in the methods disclosed herein. The protein encoded by the DPP4 gene is an antigenic enzyme expressed on the surface of most cell types and is associated with immune regulation, signal transduction and apoptosis. It is an intrinsic membrane glycoprotein and a serine exopeptidase that cleaves X-proline dipeptides from the N-terminus of polypeptides.

Non-Exclusive NCBI Accession Data for Certain Exemplary Biomarkers Presented Herein

| Protein Name | Protein Symbol | NCBI RefSeq Number (Mouse/Rat/Human) |
|---|---|---|
| epidermal growth factor receptor isoform 1 | EGFR | NP_997538.1/NP_113695/NP_958439 |
| leucine-rich alpha-2-glycoprotein | LRG1 | NP_084072/NP_001009717/NP_443204 |
| inter-alpha-trypsin inhibitor heavy chain H3 | ITIH3 | NP_032433/NP_059047/NP_002208 |
| inter alpha-trypsin inhibitor, heavy chain 4 isoforrn 1 | ITIH4 | NP_061216/NP_062242/NP_001159921 |
| Dipeptidyl peptidase-4 | DPP4 | NP_034204/NP_036921/NP_001926 |
| Peptidase inhibitor 16 | PI16 | NP_076223/NP_001163952/NP_699201 |
| coagulation factor V | F5 | NP_032002.1/NP_001041343/NP_000121 |
| C-reactive protein | CRP | NP_031794.3/NP_058792/NP_000558 |
| hemopexin | HPX | NP_059067.2/NP_445770/NP_000604 |
| Extracellular superoxide dismutase [Cu—Zn] | SOD3 | NP_035565/NP_037012/NP_003093 |
| Cadherin-2 | CDH2 | NP_031690/NP_112623/NP_001783 |
| fetuin-B | FETUB | NP_067539/NP_445800/NP_055190 |
| CD44 Antigen | CD44 | NP_033981/NP_037056/NP_001189485 |
| vitamin D-binding protein | GC | NP_032122/NP_036696/NP_001191235 |
| complement factor I | CFI | NP_031712/NP_077071/NP_031712 |
| serum amyloid P-component | APCS | NP_035448/NP_058866/NP_001630 |
| quiescin Q6 sulfhydryl oxidase 1 | QSOX1 | NP_075757/NP_001103368/NP_002817 |
| thrombospondin-4 | THBS4 | NP_035712/NP_058829/NP_003239 |
| vitronectin | VTN | NP_035837/NP_062029/NP_000629 |

Certain aspects of the invention provide assaying the biosample for protein biomarkers wherein the assaying step comprises extracting a desired peptide from a biosample and separating the extracted peptide mixture. In particular embodiments, the protein is extracted from a biological material of interest and the isolated proteins are enzymatically digested with a protease to generate peptide fragments. The complex peptide mixture is chromatographically separated using reversed-phase chromatography. In a particular embodiment the reversed phase chromatography is high pH reversed phase chromatography. Alternatively, the complex peptide mixture is chromatographically separated using offline ion exchange chromatography or high pH reversed-phase chromatography. Furthermore, those of skill in the art will recognize that other extraction and separation techniques are suitable for practicing embodiments of the present methods.

In particular embodiments, a stable isotope labeled standard is spiked into the protein extract prior to an enzymatic digest. The reference standard can be used for relative or absolute quantification. Yocum A K, Chinnaiyan A M. Current affairs in quantitative targeted proteomics: multiple reaction monitoring-mass spectrometry. Briefings in functional genomics & proteomics. 2009; 8(2):145-57. Epub 2009/03/13. doi: 10.1093/bfgp/e1n056. PubMed PMID: 19279071; PubMed Central PMCID: PMC2722263. A common absolute quantification method is known as AQUA (standing for Absolute QUAntification). AQUA peptides are identical in sequence to the endogenous peptide with the exception of a heavy stable isotope amino acid spiked into a sample at a known concentration. Thus, the exact concentration of the endogenous peptide, when compared to the AQUA peptide, can be determined. Gerber S A, Rush J, Stemman O, Kirschner M W, Gygi S P. Absolute quantification of proteins and phosphoproteins from cell lysates by tandem MS. Proceedings of the National Academy of Sciences of the United States of America. 2003; 100(12):6940-5. Epub 2003/05/29. doi: 10.1073/pnas.0832254100. PubMed PMID: 12771378; PubMed Central PMCID: PMC165809. When the exact concentration of stable isotope-labeled peptide is unknown, the peptide can be spiked into the sample at a known ratio and used for relative quantification. Reference standards can also be made as whole proteins or synthetic concatenated tryptic peptides in vivo using stable isotope labeled proteins (PSAQ) or concatemers (QconCAT), respectively. Kaiser S E, Riley B E, Shaler T A, Trevino R S, Becker C H, Schulman H, et al. Protein standard absolute quantification (PSAQ) method for the measurement of cellular ubiquitin pools. Nature methods. 2011; 8(8):691-6. Epub 2011/07/12. doi: 10.1038/nmeth.1649. PubMed PMID: 21743460; PubMed Central PMCID: PMC3196335; Pratt J M, Simpson D M, Doherty M K, Rivers J, Gaskell S J, Beynon R J. Multiplexed absolute quantification for proteomics using concatenated signature peptides encoded by QconCAT genes. Nature protocols. 2006; 1(2):1029-43. Epub 2007/04/05. doi: 10.1038/nprot.2006.129. PubMed PMID: 17406340.

Particular embodiments disclosed herein employ reversed-phase chromatography that is optimized to resolve low-level endogenous peptides and optimize peak shapes for quantitative peak integration. For example, in certain embodiments the HPLC system is an Eksigent Nano 2D LC equipped with a Nanoflex cHiPLC system. The Nanoflex system is optionally equipped with C18 microfluidic chips that are used for trapping and chromatographically eluting peptides in a reversed-phase gradient. In addition, the Nanoflex system is optionally equipped with a column heater to optimize the effect of temperature on peak resolution.

In particular embodiments, the methods provided herein use optimized chromatography gradient lengths to identify low abundance endogenous peptides by shifting the number of co-eluting species and reducing localized sample complexity. Accordingly, in a particular embodiment the methods herein provide an effective gradient length of 90-minutes for chromatographic separations.

To achieve high specificity, the peptide amino acid sequence of the reference standard is unique to the protein biomarker. Lange V, Picotti P, Domon B, Aebersold R. Selected reaction monitoring for quantitative proteomics: a tutorial. Molecular systems biology. 2008; 4:222. Epub 2008/10/16. doi: 10.1038/msb.2008.61. PubMed PMID: 18854821; PubMed Central PMCID: PMC2583086. Peptide length is kept between approximately 6-20 amino acids to achieve good chromatographic peak shape, proper ionization, and optimal fragmentation. Elias J E, Haas W, Faherty B K, Gygi S P. Comparative evaluation of mass spectrometry platforms used in large-scale proteomics investigations. Nature methods. 2005; 2(9):667-75. Epub 2005/08/25. doi: 10.1038/nmeth785. PubMed PMID: 16118637; Kirkpatrick D S, Gerber S A, Gygi S P. The absolute quantification strategy: a general procedure for the quantification of proteins and post-translational modifications. Methods. 2005; 35(3):265-73. Epub 2005/02/22. doi: 10.1016/j.ymeth.2004.08.018. PubMed PMID: 15722223; Picotti P, Clement-Ziza M, Lam H, Campbell D S, Schmidt A, Deutsch E W, et al. A complete mass-spectrometric map of the yeast proteome applied to quantitative trait analysis. Nature. 2013; 494(7436):266-70. Epub 2013/01/22. doi: 10.1038/nature11835. PubMed PMID: 23334424. In certain embodiments, peptide collision energies are optimized to provide the most intense fragment ions, and a scheduling method is implemented so that only a limited number of transitions are analyzed over a given cycle time. Those skilled in the art will recognize that scheduling has the capacity to increase dwell times (length of time a transition is analyzed) in order to maximize signal for a particular ion. In one embodiment, a scheduling window of 5-7 minutes is chosen resulting in dwell times of at least 20 ms or more within a 1.5-second cycle time for peptides used in the present methods. Alternatively, scheduling windows and cycle times of different lengths are also contemplated.

The use of a stable isotope as reference standard provides the ability to directly compare two or more samples within the same analysis, thus eliminating problems associated with the run-to-run variability observed in label-free methods. These standards, unique to the target protein biomarker, contain a heavy stable isotope labeled amino acid to differentiate it from the target endogenous peptide biomarker. Further, these reference standards also have the ability to assist in identifying the correct peptide isomer of interest when multiple similar peptide sequences exist in a complex protein digest, thus contributing to the specificity of the assay. Banack S A, Downing T G, Spacil Z, Purdie E L, Metcalf J S, Downing S, et al. Distinguishing the cyanobacterial neurotoxin beta-N-methylamino-L-alanine (BMAA) from its structural isomer 2,4-diaminobutyric acid (2,4-DAB). Toxicon: official journal of the International Society on Toxinology. 2010; 56(6):868-79. Epub 2010/06/22. doi: 10.1016/j.toxicon.2010.06.006. PubMed PMID: 20561540.

In certain embodiments, the levels of the one or plurality of the protein biomarkers in the biosample are detected using mass spectrometry. In particular embodiments, the levels of protein biomarkers are detected using selected reaction monitoring mass spectrometry (SRM-MS). In other embodiments, the levels of the one or plurality of the protein biomarkers in the biosample are detected using other quantitative mass spectrometry techniques, including, without limitation, spectral counting, isobaric mass tagging, or ion mobility mass spectrometry.

In further embodiments, the absolute concentration of the one or a plurality of protein biomarkers is determined. In some embodiments, absolute concentration of the one or a plurality of protein biomarkers is determined using SRM-MS in combination with the AQUA method.

In other embodiments, the detecting step of the claimed methods employs alternatives to mass spectrometry. For example, in certain embodiments, a level of protein biomarker is detected using routine immunoassay techniques known to the art. Such immunoassay techniques include, without limitation, Enzyme-Linked immunosorbent assay (ELISA), protein arrays, Western blotting, flow cytometry cell sorting, immunohistochemstry, immunocytochemistry, or immunocytometry. In some embodiments of the presently disclosed methods, the detecting step comprises variations on routine immunoassay techniques, including, without limitation, microfluidic chip-based ELISAs or Westerns.

In still other embodiments, the detecting step of the presently disclosed methods employ quantification by electrophoresis. For example, in some embodiments, the detecting step comprises, without limitation, one- or two-dimensional electrophoresis, or capillary electrophoresis. Those skilled in the art will recognize still further quantitative electrophoresis methods suitable for practicing the present disclosure.

In still further embodiments, the levels of the one or plurality of the protein biomarkers in the biosample are detected by traditional protein quantification techniques. For example, in certain embodiments the levels of one or a plurality of biomarkers are detected using, without limitation, UV-VIS spectroscopy, Bradford, BCA, or Lowry Assays. In some embodiments, detecting the levels of one or a plurality of biomarkers is accomplished after the biomarker is purified from the biosample.

In other embodiments, the detecting step of the present disclosure comprises subjected the biosample to one or more chromatographic quantitation techniques. Examples of liquid chromatography methods include cation exchange, anion exchange, reversed-phase, and size exclusion chromatography. Those skilled in the art recognize that the area under a chromatographic peak is representative of the relative amount of a biomarker present in a biosample.

"Differentially expressed" as used herein refers to a comparison between a biomarker determined in two or more biosamples, or between a biomarker determined in a biosample and a biomarker reference standard, wherein expression levels of a measured biomarker are different between the compared biosamples, or between the biosample and the reference standard. In some embodiments, differential expression comprises an increase in a compared biomarker level. In other embodiments, differential expression comprises a decrease in a compared biomarker level. In still other embodiments, differential expression comprises a change in a compared biomarker over time. In yet other embodiments, differential expression comprises a change in a compared biomarker between different stages of polyps or tumors present in the colon of a subject. In still other embodiments, differential expression comprises a change in a compared biomarker during treatment of a lesion present in the colon of a subject.

In embodiments, differential expression of one or a plurality of biomarkers of the present disclosure is used to determine the stage of lesions in the colon of a subject. In particular embodiments, differential expression comprises a deviation in the level of one or a plurality of biomarkers in a biosample from a reference biosample, or from a biomarker reference standard. In some embodiments, a deviation in one or a plurality of biomarkers of about 10%, about 20%, about 30%, about 40% about 50%, about 60%, about 70%, about 80%, or about 90%, from the corresponding reference amount, is indicative of the presence or stage of a lesion in the colon of a subject. In alternative embodiments, a deviation in one or a plurality of biomarkers of about 2-fold, about 4-fold, about 8-fold, about 10-fold, about 20-fold, about 40-fold, about 80-fold, or about 100-fold, from the corresponding reference amount, is indicative of the presence or stage of a lesion in the colon of a subject.

Methods are provided to determine the level of one or a plurality of protein biomarkers in a biosample collected from a human, non-human primate, mouse, rat, dog, cat, horse, or cow. As used herein, a "biosample" is comprised of biologic material isolated from a subject and includes, without limitation, blood, serum, tissue, plasma or blood cells.

Notably, the biomarkers useful for the presently disclosed methods comprise a bodily response at times occurring distant from the tumor or adenoma or polyp cells. Major examples include hepatically produced acute-phase and inflammatory response proteins. Acute phase, inflammatory and immune responses have been identified as a common response to tumor presence. Mantovani A, Allavena P, Sica A, Balkwill F. Cancer-related inflammation. Nature. 2008; 454(7203):436-44. Epub 2008/07/25. doi: 10.1038/nature07205. PubMed PMID: 18650914; Grivennikov S I, Greten F R, Karin M. Immunity, inflammation, and cancer. Cell. 2010; 140(6):883-99. Epub 2010/03/23. doi: 10.1016/j.cell.2010.01.025. PubMed PMID: 20303878; PubMed Central PMCID: PMC2866629. And cell adhesion represents an important function related to cancer metastasis. Hyaluronan-binding proteins such as the inter-alpha-trypsin inhibitors provide vital transport of this glycosaminoglycan to growing tumors. These are just a few examples presented here relating to the systemic response to cancer. Accordingly, one of skill in the art will recognize that the biosamples of the present invention are derived from both tumor and non-tumor cells. Furthermore, one of skill in the art will recognize that the biosamples of the present invention are optionally isolated from a broad range of materials, including without limitation blood, serum, plasma, tissue, ascites fluid, urine, and fecal matter.

Embodiments of the present disclosure provide a biosample-based test for colorectal cancer that has the sensitivity and specificity to provide an alternative to routine screening using colonoscopy as a primary screening or diagnostic mechanism. Embodiments of the method of screening use a high-throughput targeted mass spectrometry procedure, which multiplexes many protein markers into a single quantitative screening assay.

In particular embodiments, the biosample-based test for colorectal cancer using SRM-MS advantageously provides a reduced cost per biomarker, potential for increased throughput in a biomarker panel analysis, and increased sensitivity and specificity.

Certain embodiments provide methods for routine screening of populations for the presence of pre-cancerous or cancerous conditions. These methods include routine collection of blood and other materials useful for diagnostic purposes. In addition, in certain embodiments the biosample of the present invention is obtained during, or coincident to, a colonoscopy or polypectomy procedure. In still further embodiments, the biosample of embodiments of the present invention is obtained periodically following colonoscopy or polypectomy. In still further embodiments, the biosample is obtained prior to colonoscopy and levels of protein biomarkers determined to identify patients requiring colonoscopy.

Embodiments of the present methods are useful for routine screening of patient populations. The present methods are particularly advantageous in cases where compliance of eligible subjects with existing screening recommendations is low, primarily because existing screening methods can be invasive, expensive, and unavailable in rural areas. In addition, embodiments of the present methods are useful for screening of patient populations that do not present elevated risk factors for colorectal cancer (e.g. family history), or would not otherwise be indicated for currently existing screening or diagnostic methods.

In still other embodiments, methods are provided for identifying individuals who would benefit from further clinical assessment or treatment, including but not limited to, further assessment or treatment by colonoscopy or polypectomy procedures. In other embodiments, post-surgical or post-polypectomy patient monitoring is provided. In still other embodiments, the present methods are useful for monitoring responsiveness of a patient to chemopreventative or chemotherapuetic agents.

In addition, methods are provided that are capable of enhancing the diagnostic and prognostic utility of currently existing colorectal screening, diagnostic, prognostic and treatment techniques. Accordingly, certain embodiments disclosed here are useful in combination with other techniques known to the art, including colonoscopy, CT scan, or Fecal Occult Blood Test.

In a further aspect, the disclosure is directed to a kit for staging of colorectal lesions in a subject. The kit includes one or more detecting reagents for detecting the one or a plurality of biomarkers of the present disclosure, and optionally includes a set of standard values for one or a plurality of protein biomarkers associated with the stage of cancerous or pre-cancerous colorectal lesions.

Moreover, the present disclosure relates to a kit adapted for carrying out methods of the present disclosure referred to above comprising; a) means for detecting the amounts of the one or a plurality of biomarkers in a biosample of the present disclosure, b) means for comparing the amounts determined in step a) with reference amounts. In some embodiments, the kit comprises instructions for carrying out methods of the present disclosure. In other particular embodiments, the kit includes a collection container in which the biosample is collected. The collection container can include solutions for preparing the biosample for assaying.

The term "kit" as used herein refers to a collection of the aforementioned means, suitably, provided separately or within a single container. The container, also suitably, comprises instructions for carrying out methods of the present disclosure.

The invention will be further described in the following examples, which do not limit the scope of the invention described in the claims.

The examples that follow are illustrative of specific embodiments of the invention and various uses thereof. They are set forth for explanatory purposes only and are not to be taken as limiting the invention.

Examples

Patient Populations

Figure 4:
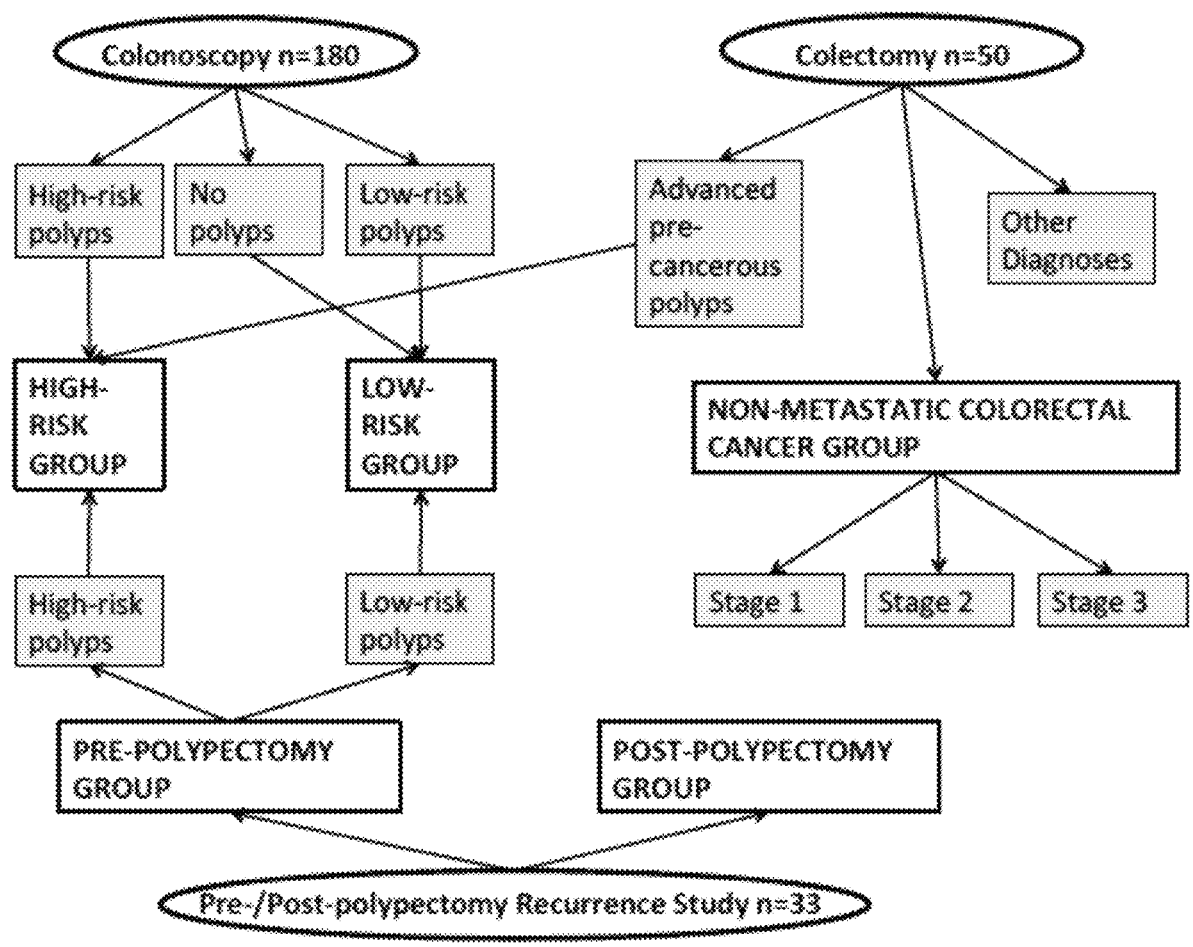
FIG. 4 illustrates the three distinct patient enrollment populations (ovals) and the subsequent patient groups (white boxes) derived from the enrolled patients. From the colonoscopy group, there were three distinct classes of patients: those with high-risk polyps (Advanced adenomas), low-risk polyps, and no polyps. The "no polyps" and "low-risk polyps" patients all were placed into the overall low risk group. Any patients with high-risk polyps were placed into the high-risk group. Pre-polypectomy patients from the "Pre-/Post-" study had known polyps as indicated by CT colonography. Each of those patients' polyps either fell into the low-risk or high-risk groups. Most of the patients undergoing colorectal surgery (Colectomy) fell into the non-metastatic cancer group. One patient ended up having an advanced adenoma (high-risk) and several other patients ended up with other diagnoses (e.g. neuroendocrine tumor). The non-metastatic group could be split into the three non-metastatic stages of colorectal cancer: Stage 1, Stage 2, and Stage 3. The hallmark of Stage 3 is regional lymph node invasion.

Patients were enrolled from three distinct patient groups (FIG. 4). Asymptomatic adults undergoing routine screening colonoscopy (n=180), patients with colorectal cancer undergoing surgical resection for removal and staging of the disease (n=50), and patients with polyps (n=33) as observed by CT colonography (virtual colonoscopy). CT colonography patients with polyps subsequently underwent colonoscopy for their removal (polypectomy).

Every biopsied polyp or surgical resection was sent to clinical pathology for analysis. Patients with non-cancerous polyps were categorized as having an advanced adenoma (high-risk) or low-risk polyps according to the current standard of care criteria outlined in Table 2. Surgical resections were staged according to the TNM staging system shown in Table 1.

Prior to colonoscopy or colorectal surgery, a blood sample was taken from each patient. Patients that underwent CT Colonography and subsequent colonoscopy returned 3-4 weeks post-polypectomy for a second blood draw to monitor the changes in biomarker expression after polyps had been removed.

Each of the patients in the longitudinal CT Colonography/ colonoscopy study was monitored for between 2 and 11 years by CT colonography, and polyps biopsied during a colonoscopy if one was classified as likely growing during the monitored time period. Final growth classifications were made based on either the polyp length or measured volume as determined by CT colonography. However, some patients had more than one polyp, and not all polyps in a single patient were necessarily classified as growing. Table 9 describes how patient growth was classified in cases where more than one polyp was present at the time of colonoscopy. Therefore, one mode of analysis for the pre-/post-polypectomy cases was to classify the patient cases into the same low- and high-risk categories as done for the colonoscopy only cases regardless of growth status, and analyze cases specifically based on their pre- and post-polypectomy status (Table 2). The second mode of analysis was to examine the effect longitudinal growth by comparing pre-polypectomy values in growing adenoma cases with adenomas of unknown growth from routine screening colonoscopy (i.e. cases that were not monitored longitudinally by CT colonography).

Protein Biomarker Candidate Selection

Serum proteins for SRM-MS analysis were chosen from two different studies. First, some proteins were selected from quantitative proteomic data from the serum of the Apc$^{Min/+}$ mouse compared with wild-type, as described in Ivancic, M M, Huttlin, E L, et al., supra. Nearly all of the proteins validated in an Apc$^{Pirc/+}$ rat biomarker validation study were also used. Ivancic M M, Irving A A, Jonakin K G, Dove W F, Sussman M R. The concentrations of EGFR, LRG1, ITIH4, and F5 in serum correlate with the number of colonic adenomas in ApcPirc/+ rats. Cancer Prev Res (Phila). 2014; 7(11):1160-9. Epub 2014/09/10. doi: 10.1158/1940-6207.CAPR-14-0056. PubMed PMID: 25200834; PubMed Central PMCID: PMC4221466. An isotopically labeled peptide reference standard unique to each selected biomarker candidate was synthesized by the UW-Madison Biotechnology Center's peptide synthesis core facility, with the incorporation of one heavy stable isotope labeled amino acid (example: $^{13}C^{15}N$ carbons and nitrogens) in each reference peptide. The selected biomarkers are listed in Table 3.

TABLE 3

List of proteins and associated abbreviations for biomarkers.

| Protein Name | Protein Symbol |
|---|---|
| epidermal growth factor receptor isoform 1 | EGFR |
| leucine-rich alpha-2-glycoprotein | LRG1 |
| inter-alpha-trypsin inhibitor heavy chain H3 | ITIH3 |
| inter alpha-trypsin inhibitor, heavy chain 4 isoform 1 | ITIH4 |
| Dipeptidyl peptidase-4 | DPP4 |
| Peptidase inhibitor 16 | PI16 |

TABLE 3-continued

List of proteins and associated abbreviations for biomarkers.

| Protein Name | Protein Symbol |
|---|---|
| coagulation factor V | F5 |
| C-reactive protein | CRP |
| hemopexin | HPX |
| Extracellular superoxide dismutase [Cu—Zn] | SOD3 |
| Serum Amyloid P | APCS |
| CD44 antigen | CD44 |
| Complement Factor I | CFI |
| Fetuin B | FETUB |
| Vitamin D-binding protein | GC (VitD) |
| Sulfhydryl Oxidase 1 | QSOX1 |
| Cadherin-2 | CDH2 |
| Thrombospondin-4 | THBS4 |
| Vitronectin | VTN |

TABLE 4

Exemplary Peptide Sequences Useful in Disclosed Embodiments

| SEQ ID NO | Peptide Sequence | Protein Biomarker Name |
|---|---|---|
| 1 | YGFIEGHVVIPR | CD44 antigen |
| 2 | VFSLQWGEVK | Complement Factor I |
| 3 | VAAGAFQGLR | Leucine-Rich alpha-2-glycoprotein |
| 4 | SLSQQIENIR | Collagen alpha-1(I) chain |
| 5 | IPLENLQIIR | Epidermal Growth Factor Receptor |
| 6 | NYVVTDHGSCVR | |
| 7 | EVSFDVELPK | Inter-alpha-trypsin inhibitor heavy chain H3 |
| 8 | AYVAFPDFFR | Maltase Glucoamylase |
| 9 | SSVYANAFPSTPVNPLR | |
| 10 | NFFNPPIISR | Coagulation factor V |
| 11 | LWWLDLK | Hemopexin |
| 12 | TIEAEAAHGTVTR | Isocitrate dehydrogenase [NADP], mitochondrial |
| 13 | EAEAAIYHLQLFEELR | Pyruvate Kinase, M2 |
| 14 | VLEPTLK | Vitamin D-binding protein |
| 15 | FEDGVLDPDYPR | Vitronectin |
| 16 | FAHTVVTSR | Inter-alpha-trypsin inhibitor, Heavy chain 4 |
| 17 | TLTLLSVTR | CEACAM5 |
| 18 | LCGTFLGGPKPPQR | Cathepsin B |
| 19 | GYVIIKPLVWV | Serum Amyloid P |
| 20 | IFFESVYGQCK | Fetuin B |
| 21 | ESDTSYVSLK | C-reactive protein |
| 22 | FTVDRPFLFLIYEHR | heparin cofactor 2 |

TABLE 4 -continued

Exemplary Peptide Sequences Useful in Disclosed Embodiments

| SEQ ID NO | Peptide Sequence | Protein Biomarker Name |
|---|---|---|
| 23 | LAGAPSEDPQFPK | Sulfhydryl Oxidase 1 |
| 24 | AEEYEFLTPVEEAPK | Rho-GDP Dissociation Inhibitor 1, Isoform a (ARHGDIA) |
| 25 | WDEELAAFAK | Peptidase inhibitor 16 |
| 26 | GPFPQELVR | Cadherin-2 (N-Cadherin) |
| 27 | WEYYDSVYTER | Dipeptidyl peptidase 4 |
| 28 | VTGVVLFR | extracellular superoxide dismutase [Cu-Zn] |
| 29 | DVDIDSYPDEELPCSAR | Thrombospondin-4 |
| 30 | GFGPPATNQFTTK | receptor-type tyrosine-protein phosphatase mu |

Sample Processing

Blood from each patient was processed into serum. Five milliliters of blood was collected into a 1-5 ml red top serum tube and incubated at room temperature (15-25° C.) for 30 min-4 hours. The tube was centrifuged for 15 minutes at 1500×g. All centrifugation steps were carried out at room temperature in a swing-out rotor. Blood serum was aliquoted in 100 µl or 300 µl aliquots into 0.5 mL low bind Eppendorf Tubes and stored at −80° C.

Serum was thawed at room temperature and the top seven major blood proteins were removed using a Human 4.6 mm×100 mm Agilent Multiple Affinity Removal Column. All of the proprietary buffers and filters were used according to manufacturer instructions. A Waters 1740 HPLC equipped with a manual sample injector and a 1 mL sample loop was used. Prior to depletion, 50 µl of serum was added to 400 µl of Agilent Buffer A before filtering. Each sample injection was monitored at 215 and 280 nm using a Waters 2996 photodiode array detector with both bound and unbound fractions collected. Fractions were stored at −80° C. until further use.

Unbound fractions were thawed at room temperature and filtered using Agilent 5 kDa MWCO concentrating filter units at 4000×g (4° C.) until approximately ≤500 µL of liquid remained. The concentrated protein was precipitated by adding cold 50% trichloroacetic acid to a final concentration of 10% and allowing the samples to incubate on ice for 5 min. Proteins were pelleted using a microcentrifuge for 5 min at 4000×g at 4° C. The centrifugation step was repeated with four washes of cold 80% acetone in water followed by one wash in cold 50% methanol in water. The supernatant was removed after each wash, and the pellet was allowed to air-dry after the final wash. Pellets were resolubilized overnight at 4° C. in 50 mM ammonium bicarbonate, 8 M urea, pH 8. The partially dissolved pellets were diluted to 1.6 M urea, 50 mM Ammonium bicarbonate pH 8. Each sample was sonicated for 5-second pulses a total of three times using a sonicating probe.

A BCA protein concentration assay (Pierce) was performed according to the manufacturer's instructions. A 100 µg aliquot of serum protein from each sample underwent reduction and alkylation of cysteine residues, followed by digestion at 37° C. overnight using sequencing grade porcine trypsin (Promega) at a 1:50 trypsing protein ratio. Before reduction and alkylation, the stable isotope labeled peptide reference standard of each target endogenous peptide was added to the serum protein sample. The resultant peptides were desalted on SPEC C18 Pipette Tips (Agilent Technologies) according to the manufacturer's instructions. Eluted peptides were dried using a vacuum centrifuge and stored at −80° C. until LC-MS/MS analysis.

Liquid Chromatography-Mass Spectrometry Method

Liquid chromatography separation of a 2 µg sample was achieved by reversed-phase chromatography using a NanoLC Ultra 2D HPLC (Eksigent) equipped with a nano-flex cHiPLC set to 37° C. A 90-minute gradient was used for peptide separation as described in Ivancic, MM, Huttlin, E L, et al., supra, followed by elution directly into a 5500 QTrap (AbSciex). Peptide precursors were selected in quadrupole 1 (Q1), fragmented in q2, and the top 3 to 4 transitions were selected for monitoring in Q3. All Q1 and Q3 masses were measured at unit resolution. A 7-minute scheduling window was applied with a 2-second cycle time. Method development and peak analysis were done using Skyline software (Ivancic M M, et al. The concentrations of EGFR, LRG1, ITIH4, and F5 in serum correlate with the number of colonic adenomas in ApcPirc/+ rats. Cancer Prev Res (Phila). 2014; 7:1160-9.). All biological samples were analyzed by LC-MS/MS in three technical replicates.

Mass Spectrometry Data Processing and Analysis

Mass spectrometry results were imported into Skyline and peaks integrated. Each peptide was evaluated using the average peak area of the most intense transition over the three technical replicates. For each protein, an average ratio of was calculated for each of the peptides comparing the patient groups as indicated in Table 5.

In addition, the pre-/post-polypectomy ratios for low-risk, high-risk, and villous/serrated polyps were compared. P-values were obtained using a two-tailed non-parametric Mann-Whitney t-test at a 95% confidence interval. Mann-Whitney p-values were filtered using a Benjamini Hochberg 5% false discovery rate calculation for cases that compared adenoma and carcinoma stages. The CTC study and Pre-/Post-polypectomy study utilized Mann-Whitney p-values but was not filtered for false discoveries based on the possibility of too many false negative results given the sample size. Individual protein ROC curves were determined using a logistic regression algorithm. ROC panel curves were optimized using several different machine-learning algorithms including: Linear SVM, Logistic Regression, and Random Forests. iaw AW, M. Classification and Regression by randomForest. R News. 2002; 2/3:5; Burges C J C. A Tutorial on Support Vector Machines for Pattern Recognition. Data Mining and Knowledge Discovery. 1998; 2:121-67; Zou K H, O'Malley A J, Mauri L. Receiver-operating characteristic analysis for evaluating diagnostic tests and predictive models. Circulation. 2007; 115(5):654-7. doi: 10.1161/CIRCULATIONAHA.105.594929. PubMed PMID: 17283280.

TABLE 5

Fold-change between the groups was calculated by dividing Group 1/Comparison Group. The "stages 1&2 combined" group compared to stage 3 is meant to distinguish between regional lymph node invasion (stage 3) and other non-metastatic cancers (stages 1&2).

| Group 1 | Comparison Group |
|---|---|
| No Polyps | Low-Risk Polyps |
| Advance Adenomas | Low-Risk + No polyps |

TABLE 5-continued

Fold-change between the groups was calculated by dividing Group 1/Comparison Group. The "stages 1&2 combined" group compared to stage 3 is meant to distinguish between regional lymph node invasion (stage 3) and other non-metastatic cancers (stages 1&2).

| Group 1 | Comparison Group |
|---|---|
| Stage 1 | Low-Risk + No polyps |
| Stage 2 | Low-Risk + No polyps |
| Stage 3 | Low-Risk + No polyps |
| All Cancer Cases | Low-Risk + No polyps |
| Stage 1 | Advance Adenomas |
| Stage 2 | Advance Adenomas |
| Stage 3 | Advance Adenomas |
| All Cancers | Advance Adenomas |
| Stage 2 | Stage 1 |
| Stage 3 | Stage 1 |
| Stage 3 | Stage 2 |
| Stage 3 | Stages 1 & 2 combined |
| Pre-Polypectomy | Post-Polypectomy |

Example 1: Biomarkers have Diagnostic and Prognostic Utility for Detection of Colorectal Cancers and Precancerous Conditions Blood serum was collected and analyzed for over 260 patient cases from colonoscopy, colectomy, or CT colonography/colonoscopy procedures (FIG. 5). Most colonoscopy cases were categorized into the low-risk group having either no polyps (normal tissue, n=56) or low-risk polyps (n=87). A total of 71 patients had polyps considered advanced adenomas that are high-risk for developing colorectal cancer. Out of 50 colectomy cases, 47 of the patients had non-metastatic cancer. Almost half of the cases were classified as stage 1 (n=22) while the rest were divided among stage 2 (n=13), and stage 3 (n=12) colorectal cancers. A total of 25 pre- and post-polypectomy pairs were collected from patients whose polyps were biopsied by colonoscopy after CT colonography. Eight patients did not return for a post-polypectomy blood collection. In this longitudinally monitored group, 11 low-risk, 22 high-risk cases were analyzed (8 low-risk pre/post pairs, and 17 high-risk cases with pre/post pairs).

Figure 6:
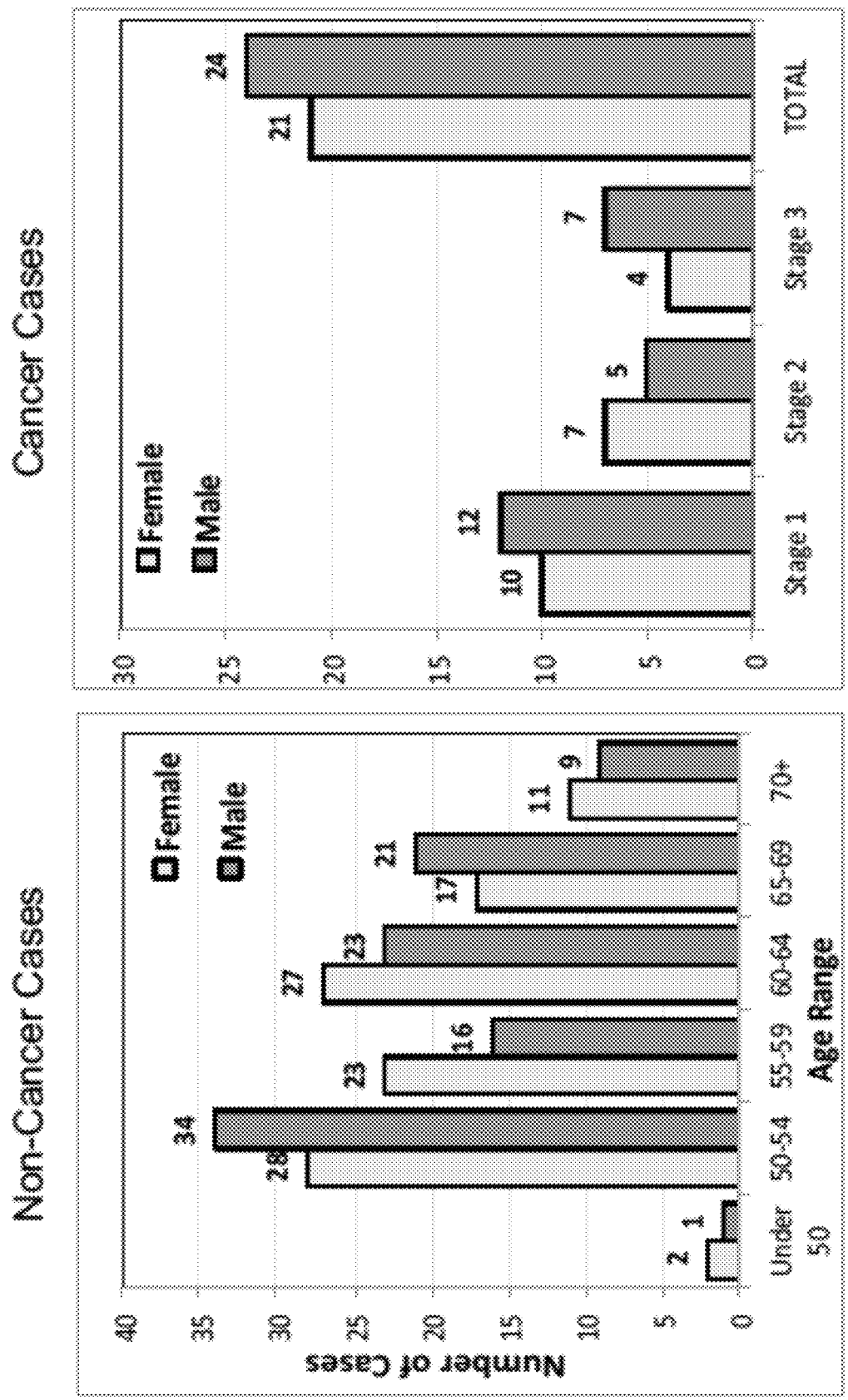
FIG. 6 describes the breakdown of gender for non-cancer cases across the age groups of patients enrolled in the study, and the gender breakdown for each colon cancer stage. In general, there were no significant gender differences in patients enrolled across age groups or cancer stages.
Figure 8:
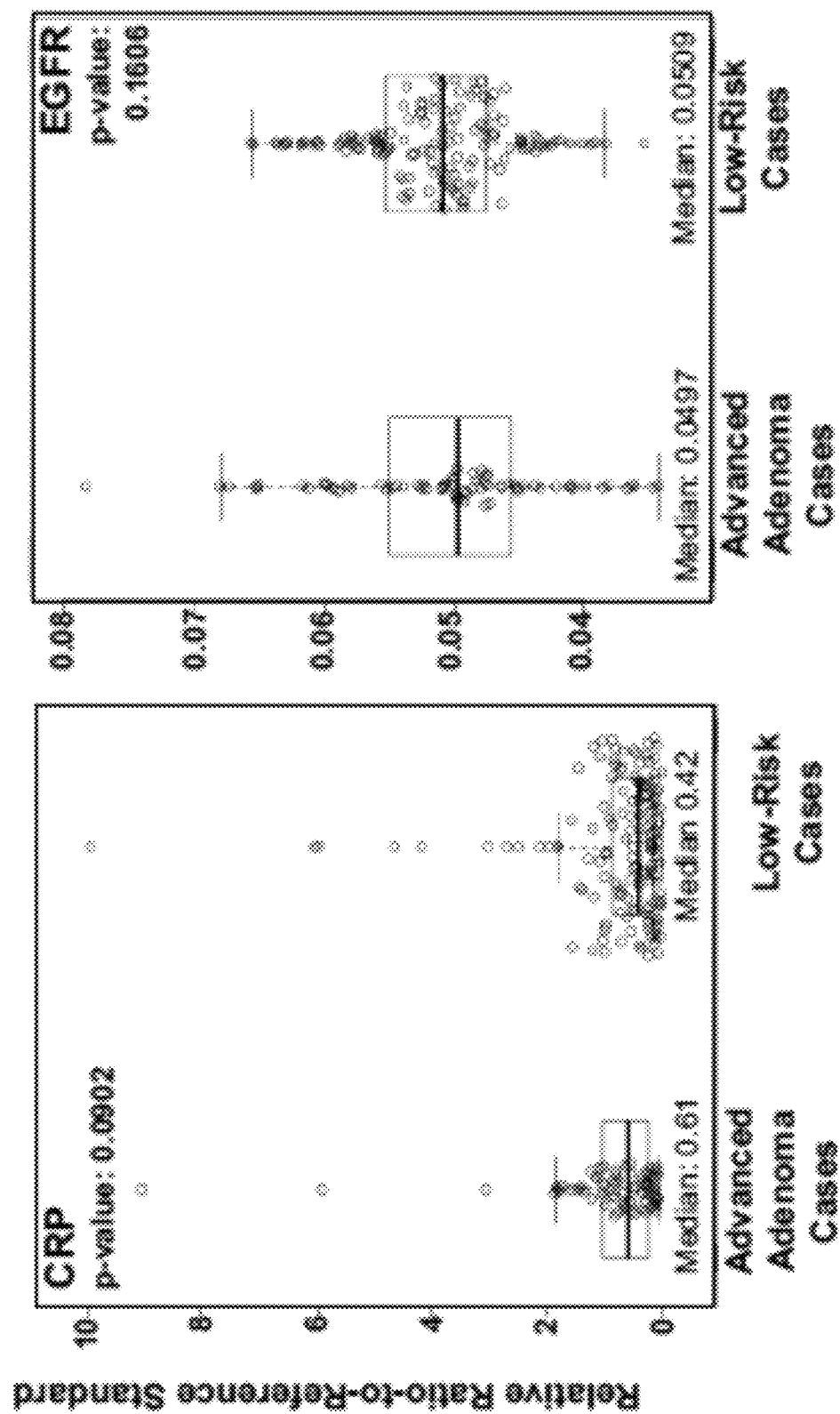
FIG. 8 shows relative ratio-to-reference standard data for CRP and EGFR in advanced adenoma (high-risk) colonoscopy cases compared to low-risk cases. In this figure, low-risk refers to all cases in which screening colonoscopy was normal or had polyps of low-risk for developing into colorectal cancer. Each circle on the dot plots represents a single patient case.
Figure 9:
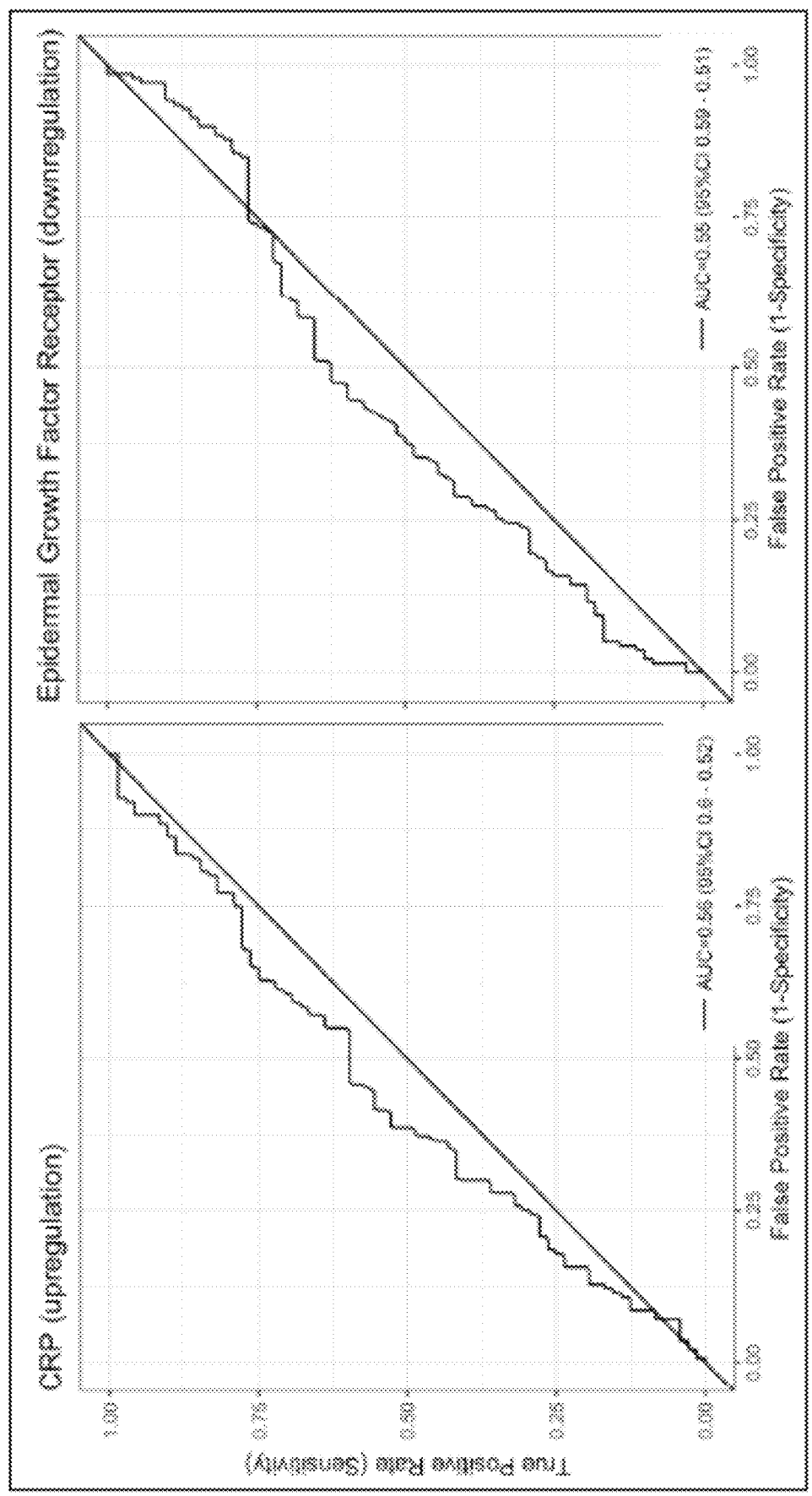
FIG. 9 shows the individual receiver operator characteristic (ROC) curves conveying the sensitivity and specificities of CRP and EGFR for identifying high-risk adenomas. Data points to the left of the diagonal line convey a positive predictive value for identifying advanced adenomas. Data points on or closer to the diagonal line indicate a 50% "coin toss" probability of identifying advanced adenomas, while data points to the right of the diagonal line indicate a negative probability.

Biomarkers Provide Differentiation Between High-Risk and Low-Risk Colorectal Adenomas Approximately equal numbers of males and females were enrolled in the study across patient ages and cancer stages (FIG. 6). CRP shows an average upregulation in expression between advanced adenoma and low-risk cases for all genders combined (FIG. 8, Table 6). Similarly, EGFR exhibits mild downregulation in advanced adenoma cases. Sensitivity and specificity Receiver Operator Characteristic (ROC) curves based on a logistic regression analysis show that these proteins predict advanced adenomas (FIG. 9).

Figure 10:
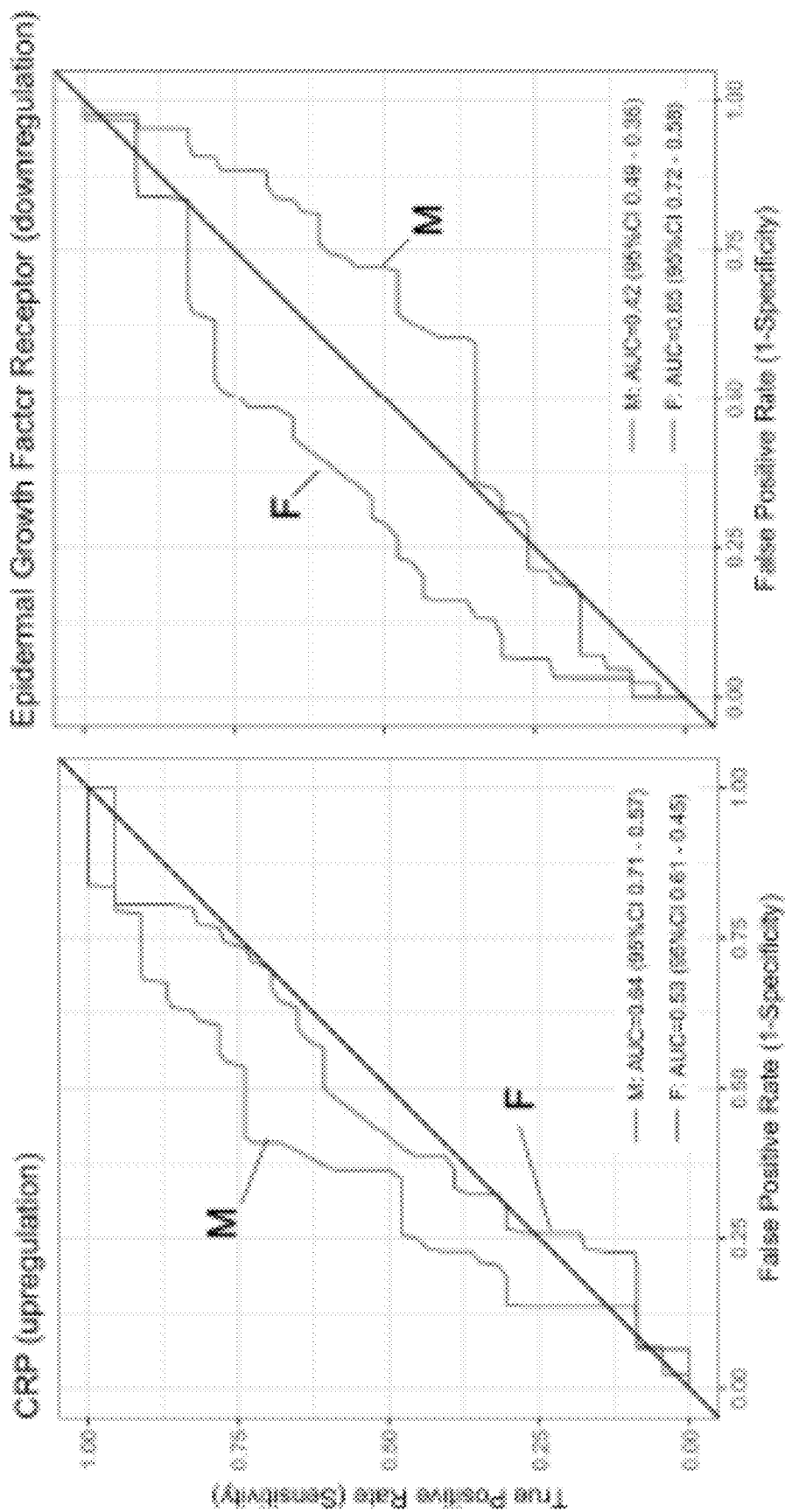
FIG. 10 illustrates the individual receiver operator characteristic (ROC) curves conveying the sensitivity and specificity for CRP and EGFR in identifying advanced adenomas based on patient gender. The ROC curves in the right panels are labeled "F" and "M" for females and males respectively.
Figure 11A:
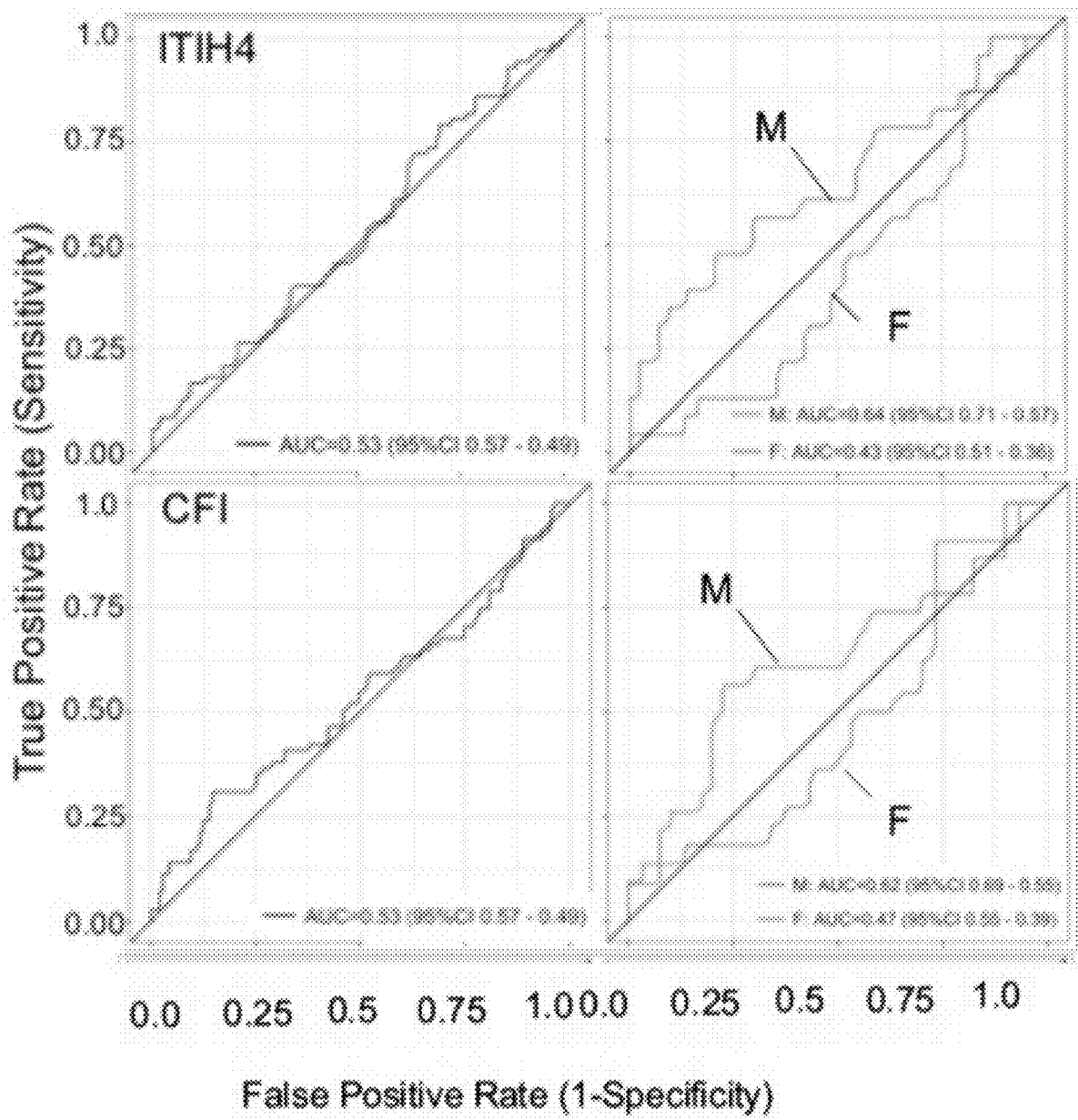
FIG. 11 shows the individual receiver operator characteristic (ROC) curves conveying the sensitivity and specificity of ITIH4, CFI, CD44, and F5 for identifying advanced adenomas in all genders combined (left panels) and when separated by gender (right panels). The ROC curves in the right panels are labeled "F" and "M" for females and males respectively.
Figure 11B:
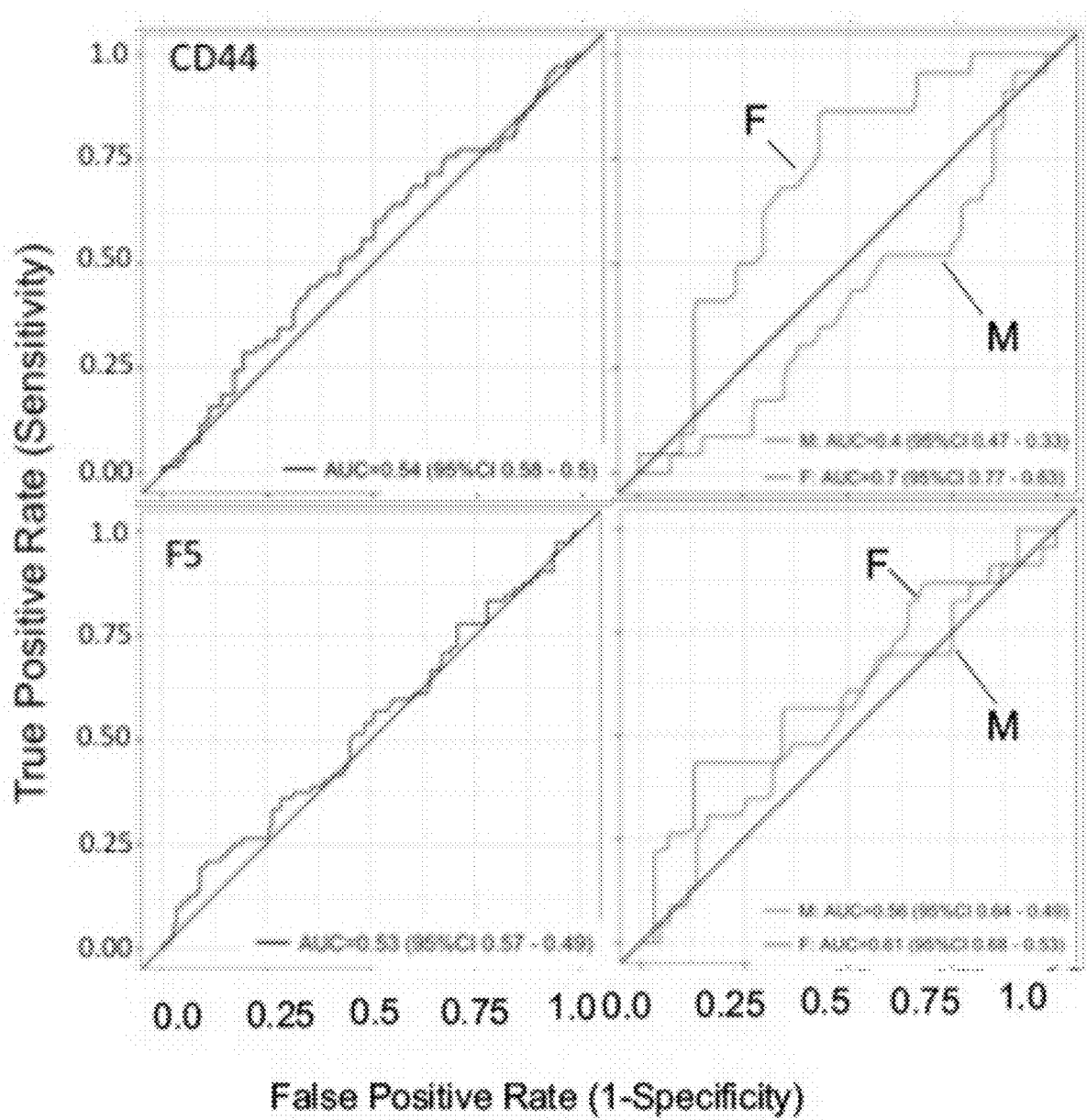

CRP and EGFR ROC curves show differences in sensitivity and specificity when divided by gender (FIG. 10). Similarly, gender differences in advanced adenoma sensitivity and specificity were observed for CD44, F5, CFI, and ITIH4 (FIG. 11).

Figure 12A:
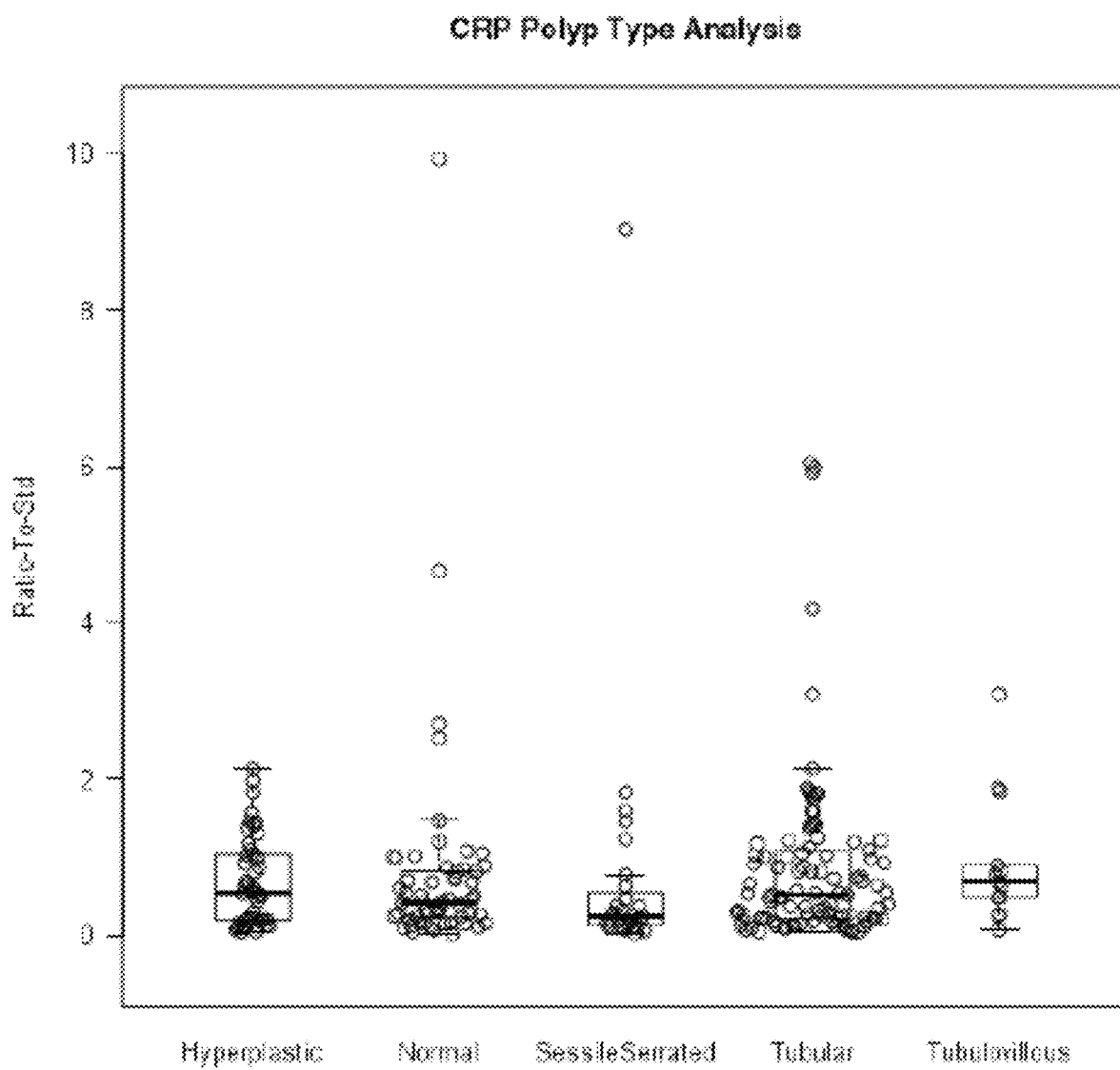
FIG. 12 shows relative ratio-to-reference standard data for ITIH3, ITIH4, and CRP across multiple non-cancerous polyp histopathologies. Each circle on the dot plots represents a single patient case.
Figure 12B:
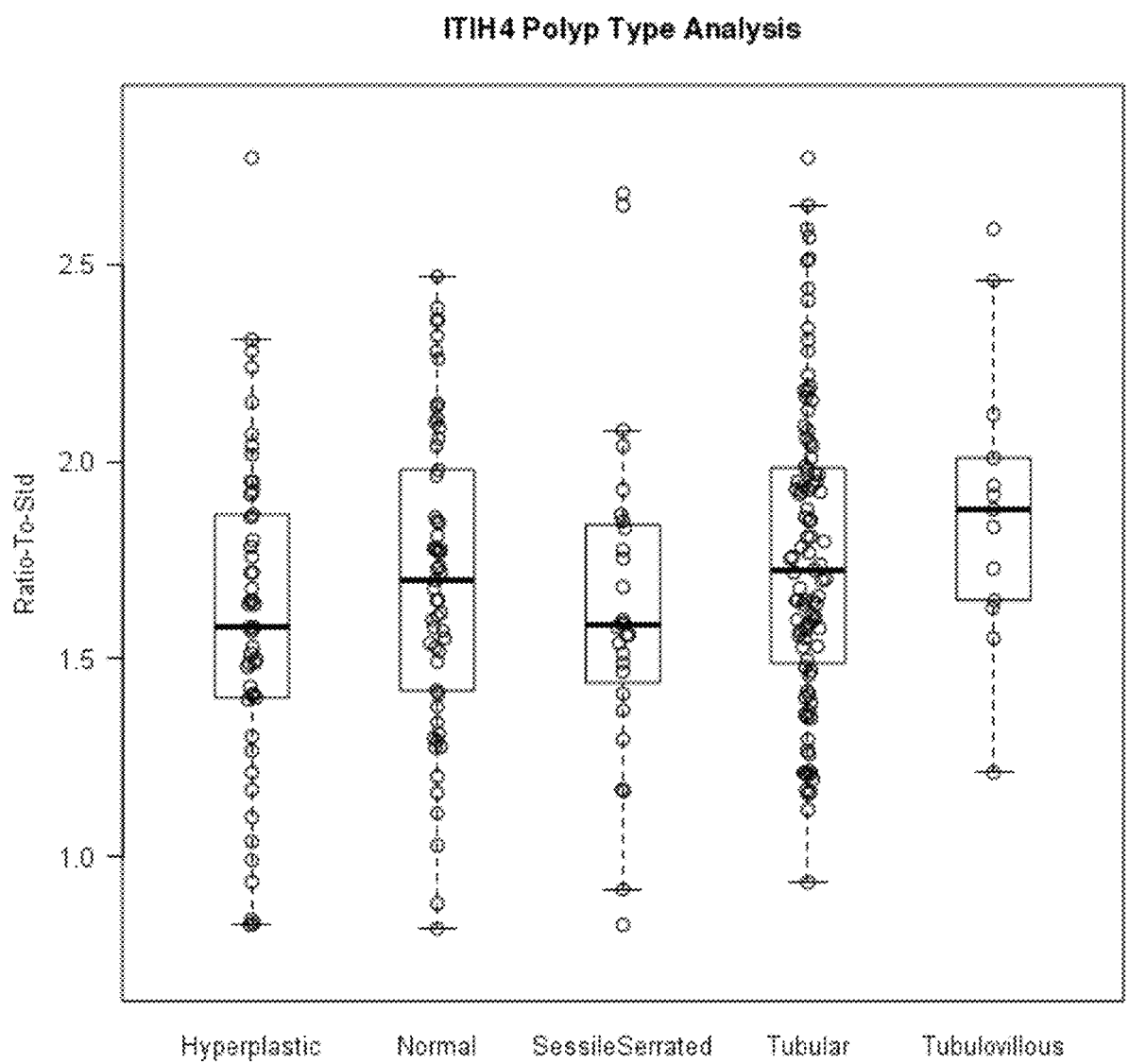
Figure 12C:
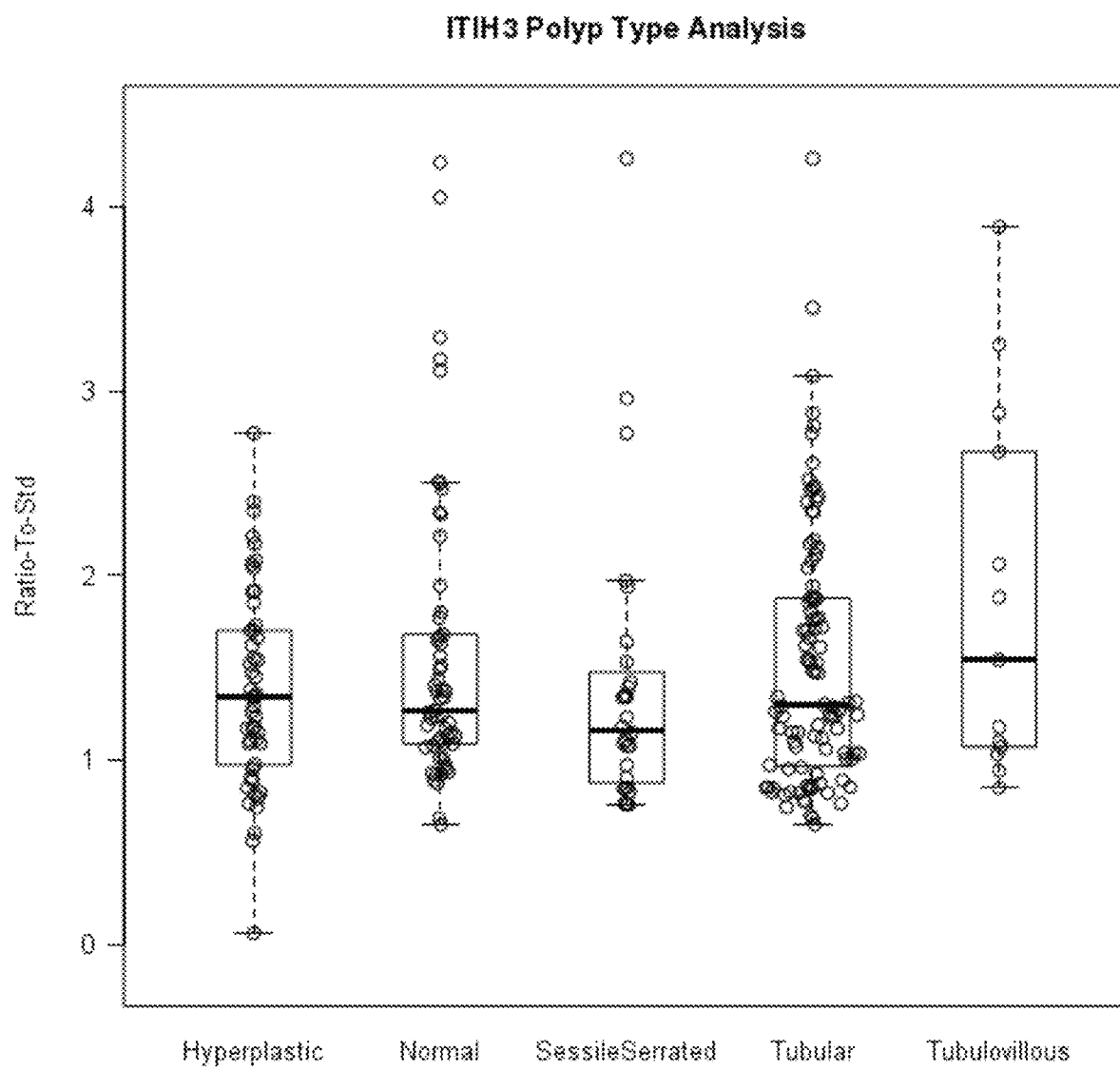

Some proteins showed specific changes in expression based on polyp histology. Villous (tubulovillous) adenomas with any grade of dysplasia have a significantly higher probability of developing into carcinomas than other types of polyps. ITIH3, ITIH4, and CRP showed median upregulation higher than that of other polyp histopathologies in tubulovillous adenomas (FIG. 12).

Figure 13:
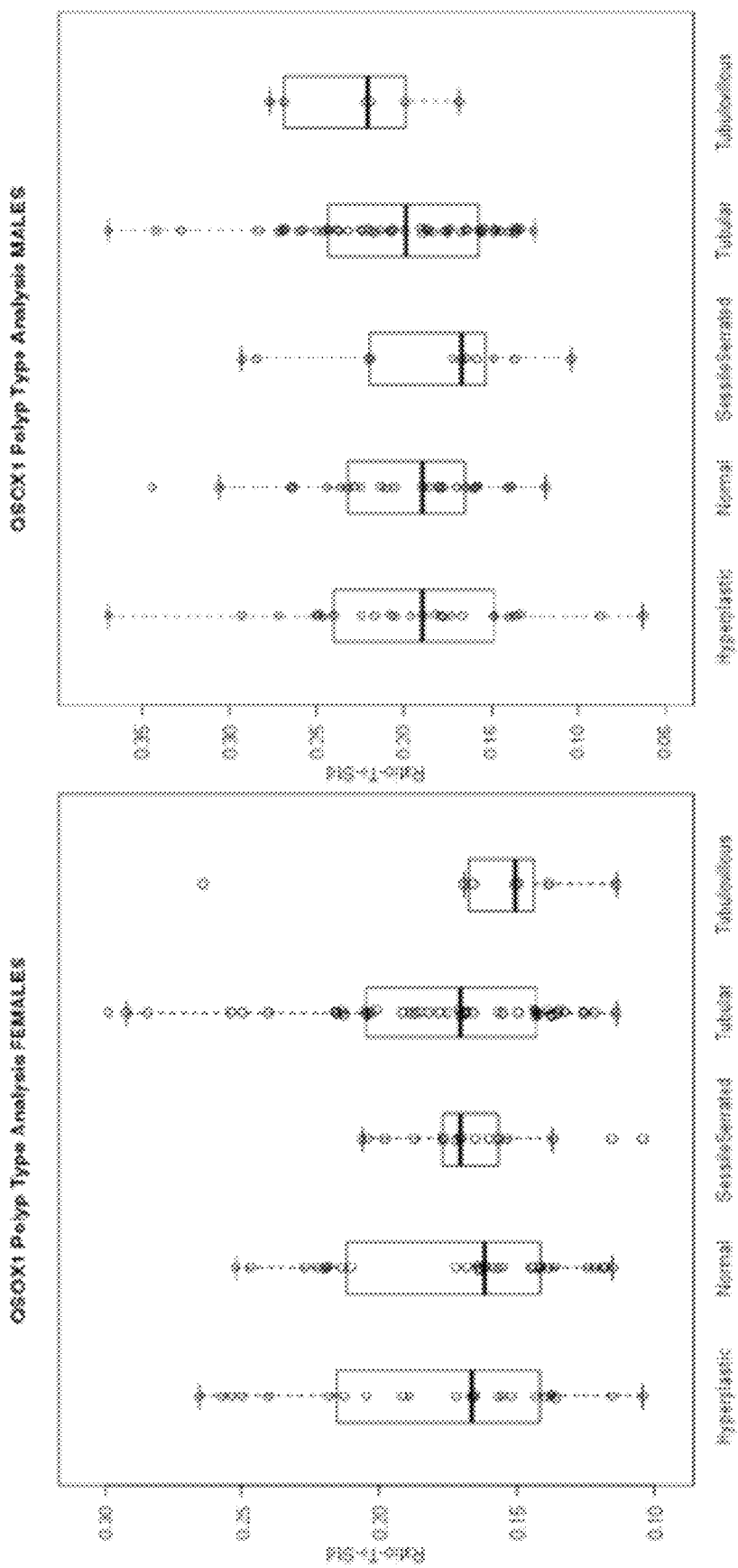
FIG. 13 shows relative ratio-to-reference standard data illustrating gender differences in expression of QSOX 1 in tubulovillous adenomas compared to other types of polyp histopathologies.

QSOX1 shows differential expression in tubulovillous adenoma cases as a function of gender (FIG. 13). Reduced QSOX1 expression was present in females with tubulovillous adenomas, while increased QSOX1 expression was present in males with tubulovillous adenomas.

Biomarkers Provide Differentiation Between Rectal and Colon Adenomas

Figure 14:
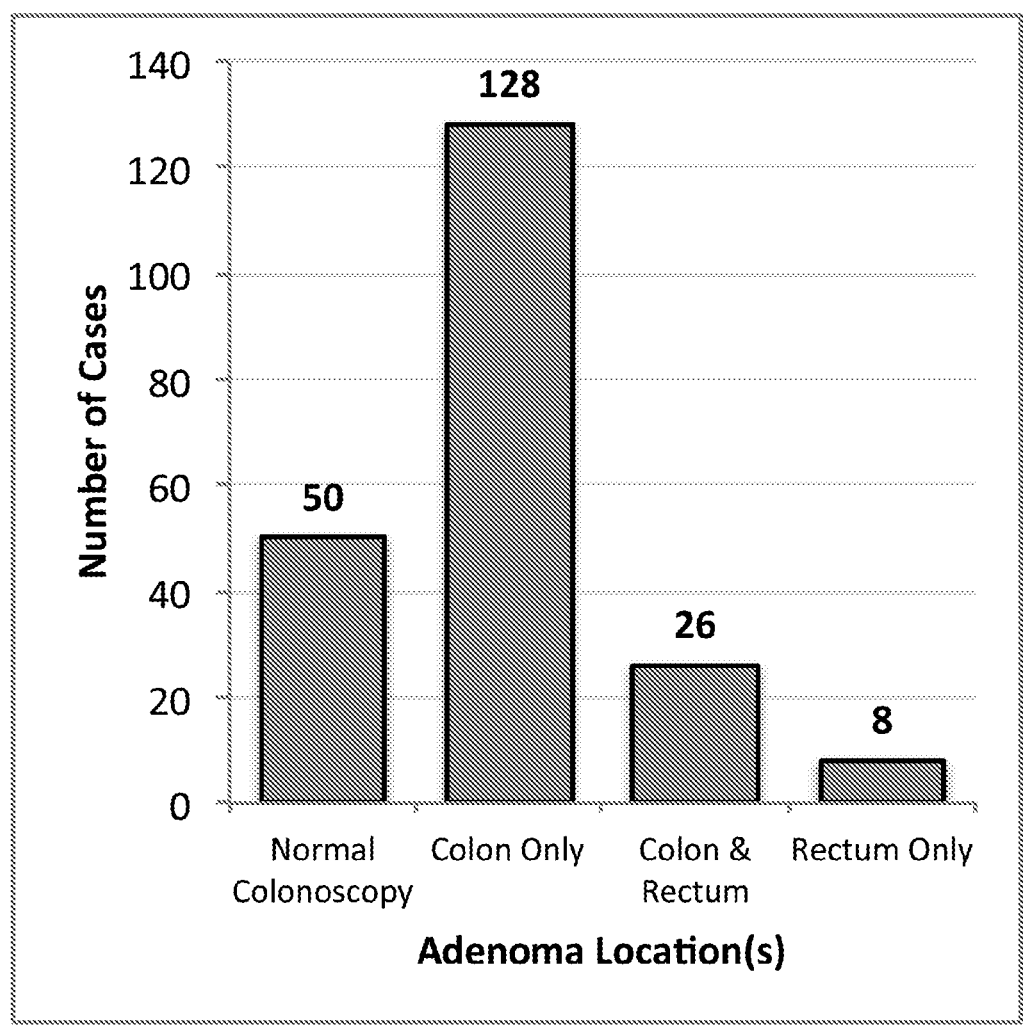
FIG. 14 identifies the number of patient cases that have polyps falling into one of four categories for colon versus rectal cancer comparisons: normal screening colonoscopy, patients with colon polyps only, patients with colon and rectal polyps, and patients with rectal polyps only. Biomarker expression was analyzed in the context of the location of adenomas within these four categories.
Figure 15A:
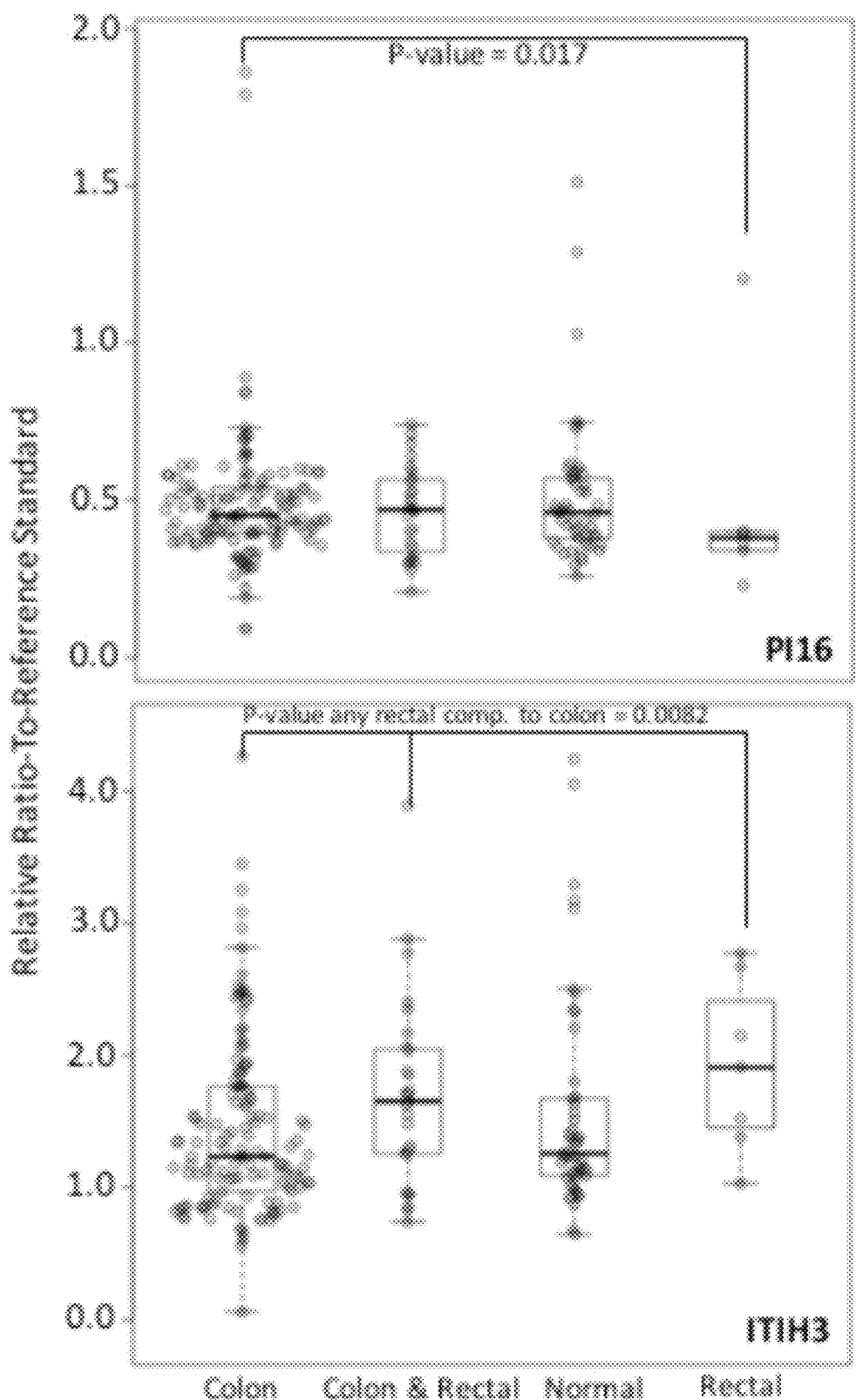
FIG. 15 shows relative ratio-to-reference standard data illustrating the differences in expression for PI16, CD44, ITIH3, and QSOX1 in cases with colon versus rectal polyps. Each circle on the dot plots represents a single patient case.
Figure 15B:
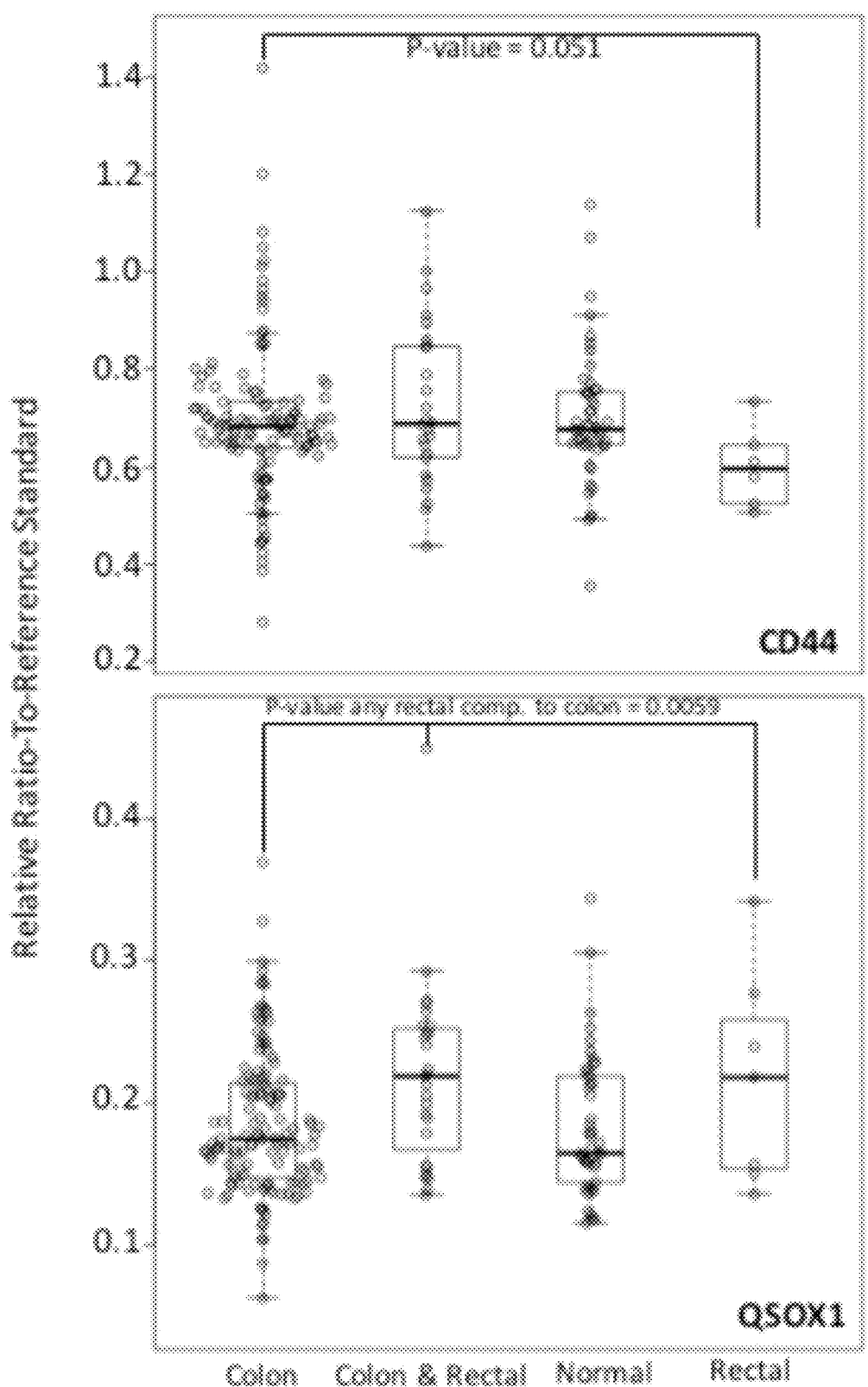

Biomarkers divided by polyp location differentiated adenomas present in the rectum compared to adenomas present in the colon. Colonoscopy patients were divided into four categories: screening normal, colon polyps only, colon and rectal polyps, and rectal polyps only. Most patients with polyps exhibited colon polyps or a mixture of colon and rectal, but some cases were specific to the rectum only (FIG. 14). CD44 and PI16 were both downregulated in cases where only rectal polyps were present (FIG. 15). ITIH3 and QSOX1 were both upregulated in cases where a rectal polyp was present, including in patients that had a mix of both rectal and colon polyps.

Figure 16A:
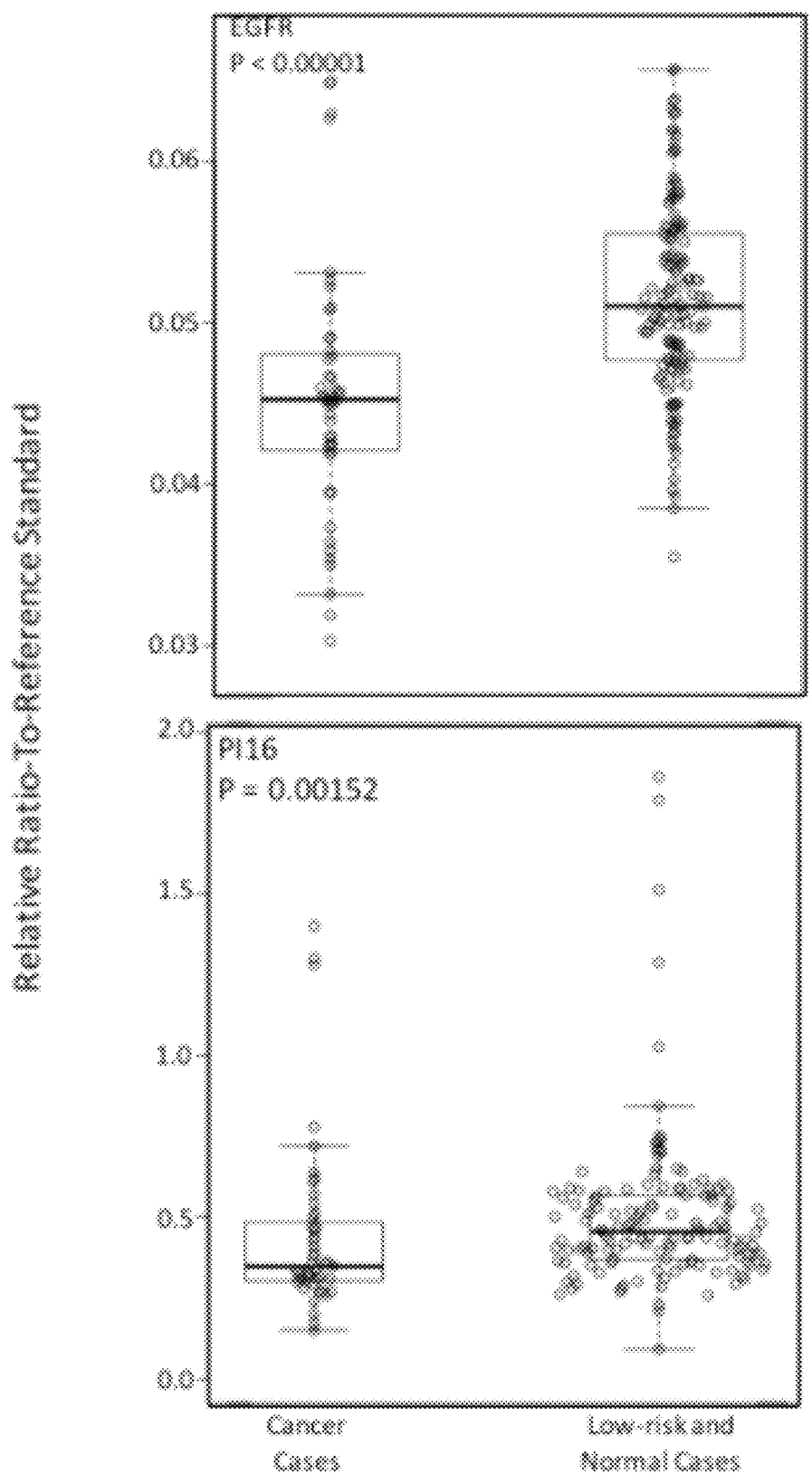
FIG. 16 shows relative ratio-to-reference standard for the indicated biomarkers in pooled low-risk and normal colonoscopy cases ("Low-risk and Normal Cases"), compared to non-metastatic cancers ("Cancer Cases"). P-values represent Mann-Whitney p-values at a 95% confidence. Each circle on the dot plots represents a single patient case.
Figure 16B:
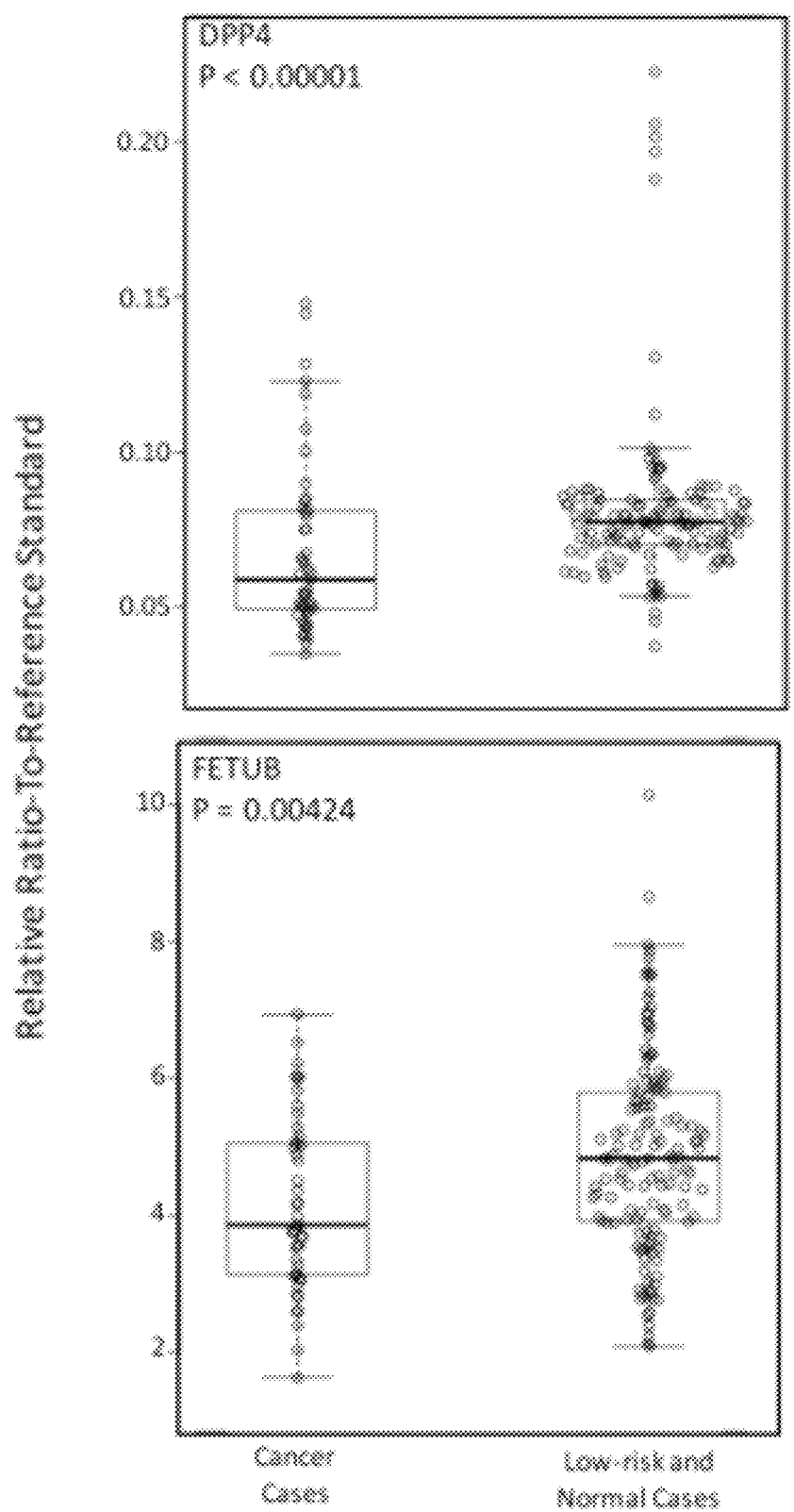
Figure 16C:
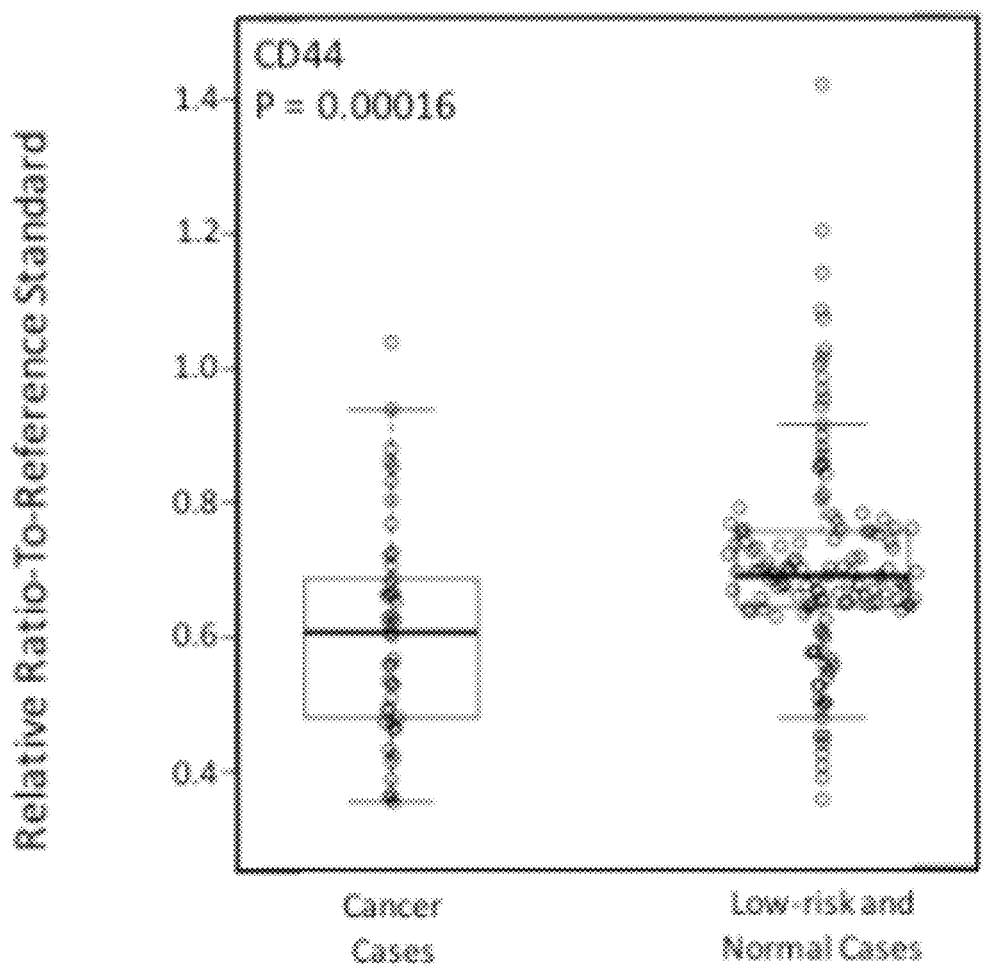
Figure 17A:
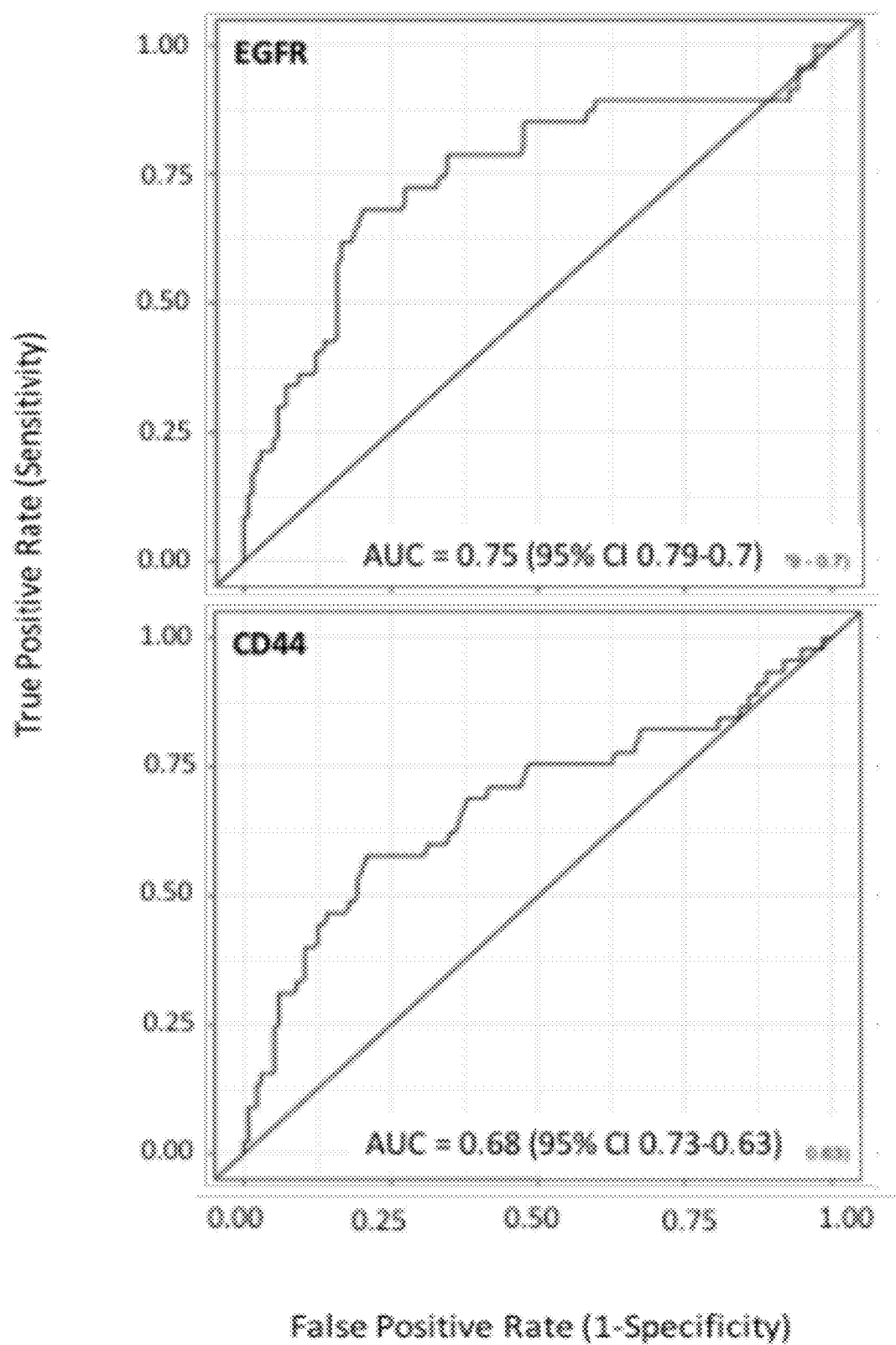
FIG. 17 illustrates the ROC curves for EGFR, DPP4, CD44, FETUB, and PI16 in low-risk and normal colonoscopy cases compared to non-metastatic cancers.
Figure 17B:
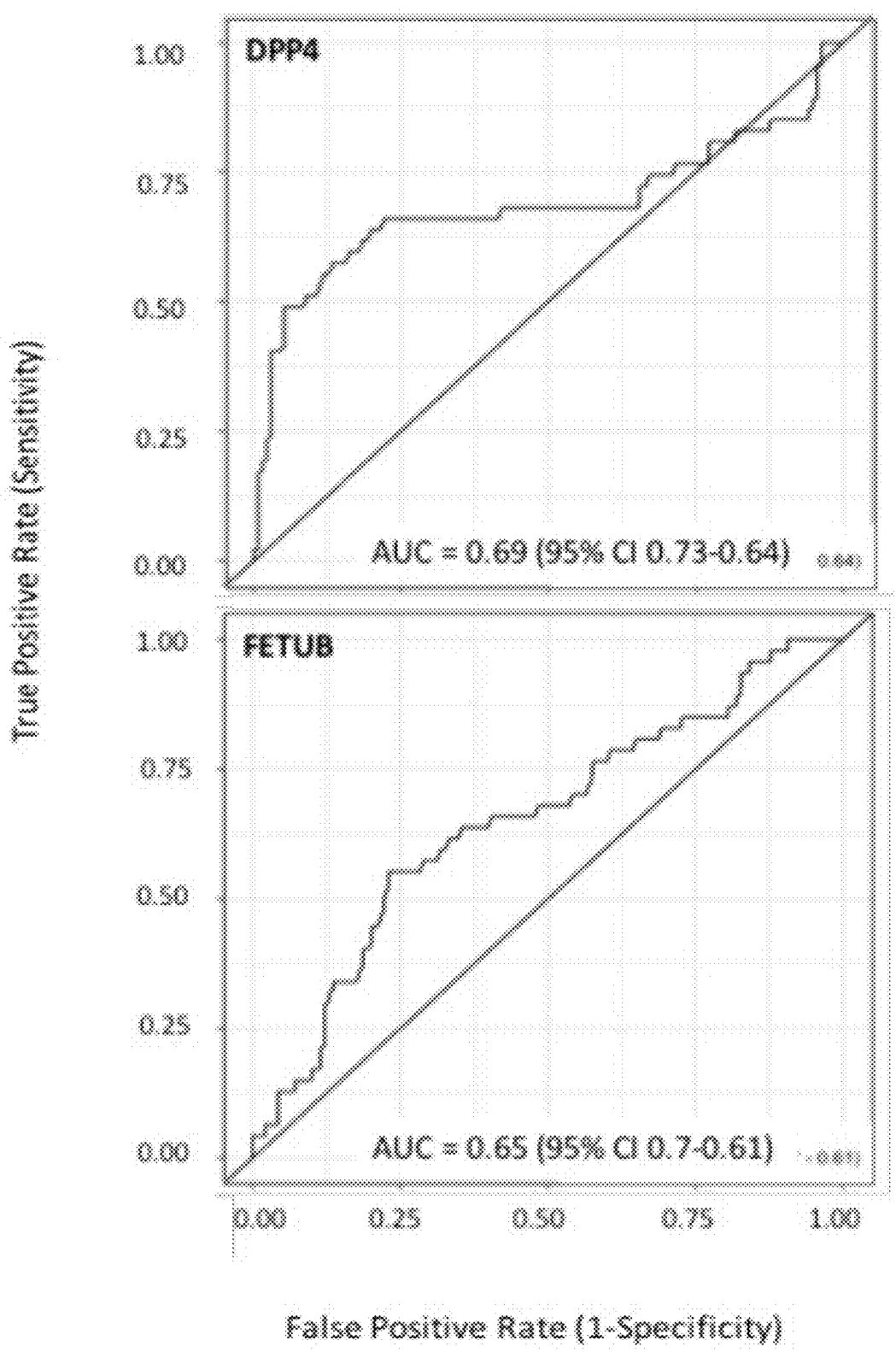
Figure 17C:
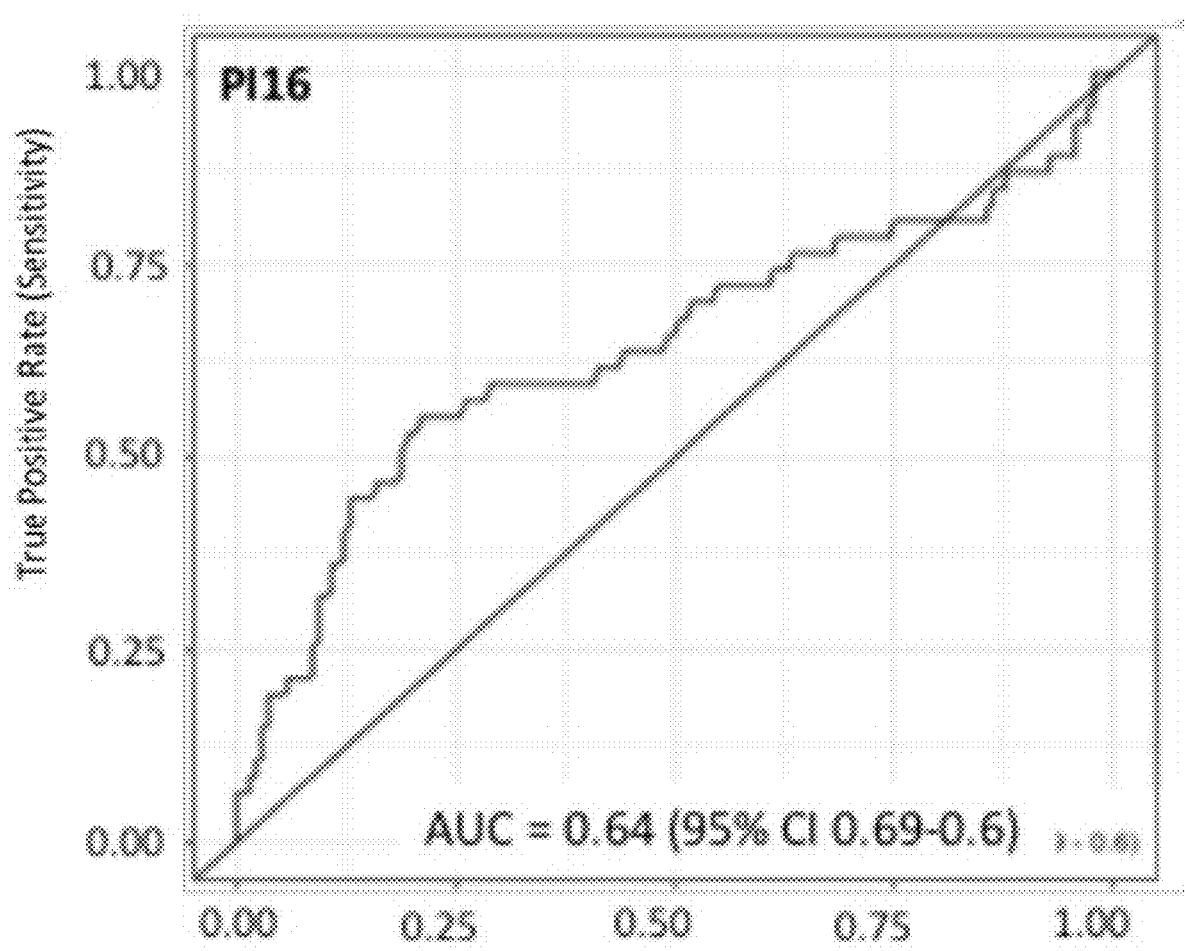
Figure 18A:
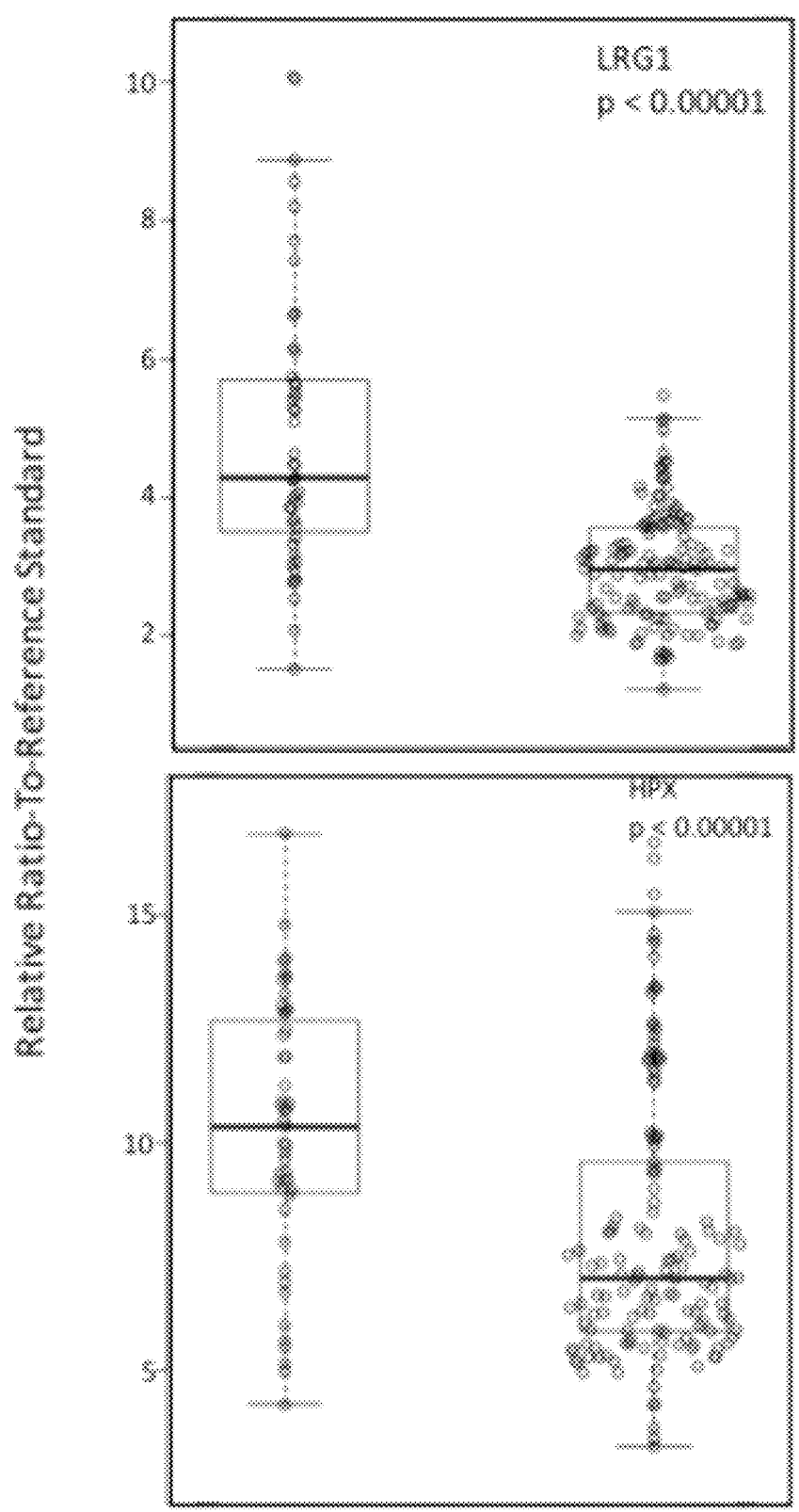
FIG. 18 shows relative ratio-to-reference standard data for the indicated biomarkers in pooled low-risk and normal colonoscopy cases ("Low-risk and Normal Cases"), compared to non-metastatic cancers ("Cancer Cases"). P-values represent Mann-Whitney p-values at a 95% confidence. Each circle on the dot plots represents a single patient case.
Figure 18B:
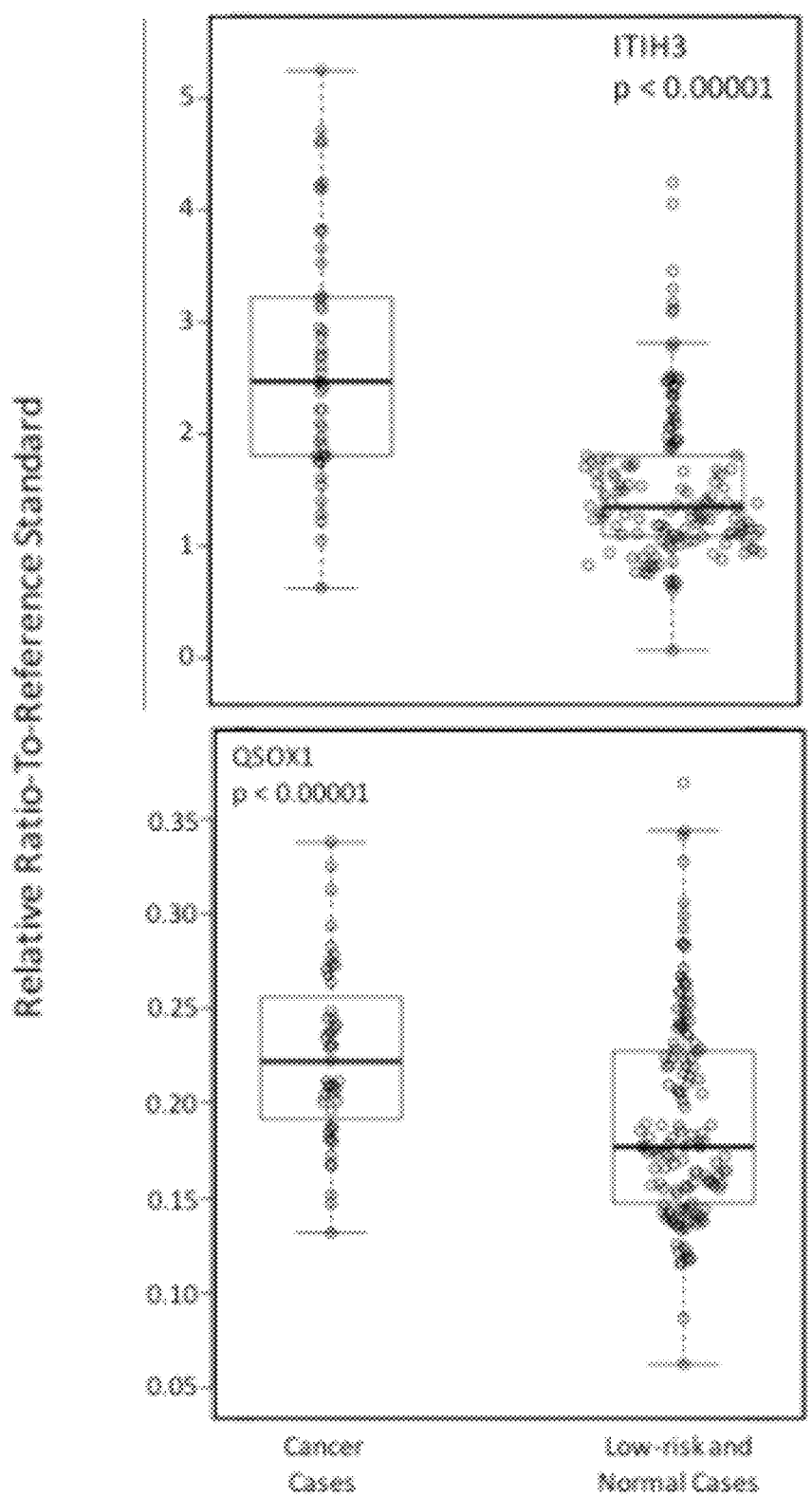
Figure 18C:
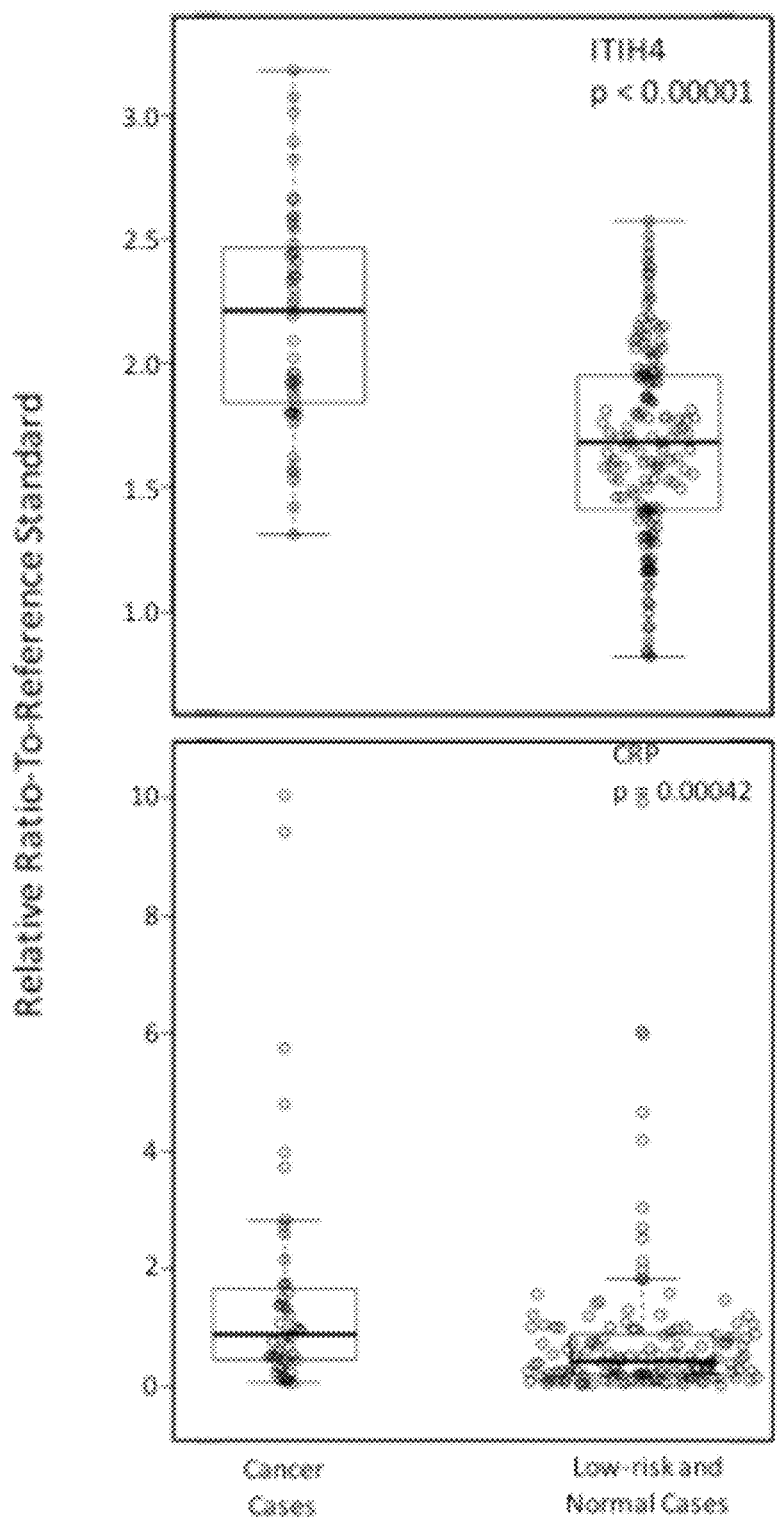
Figure 18D:
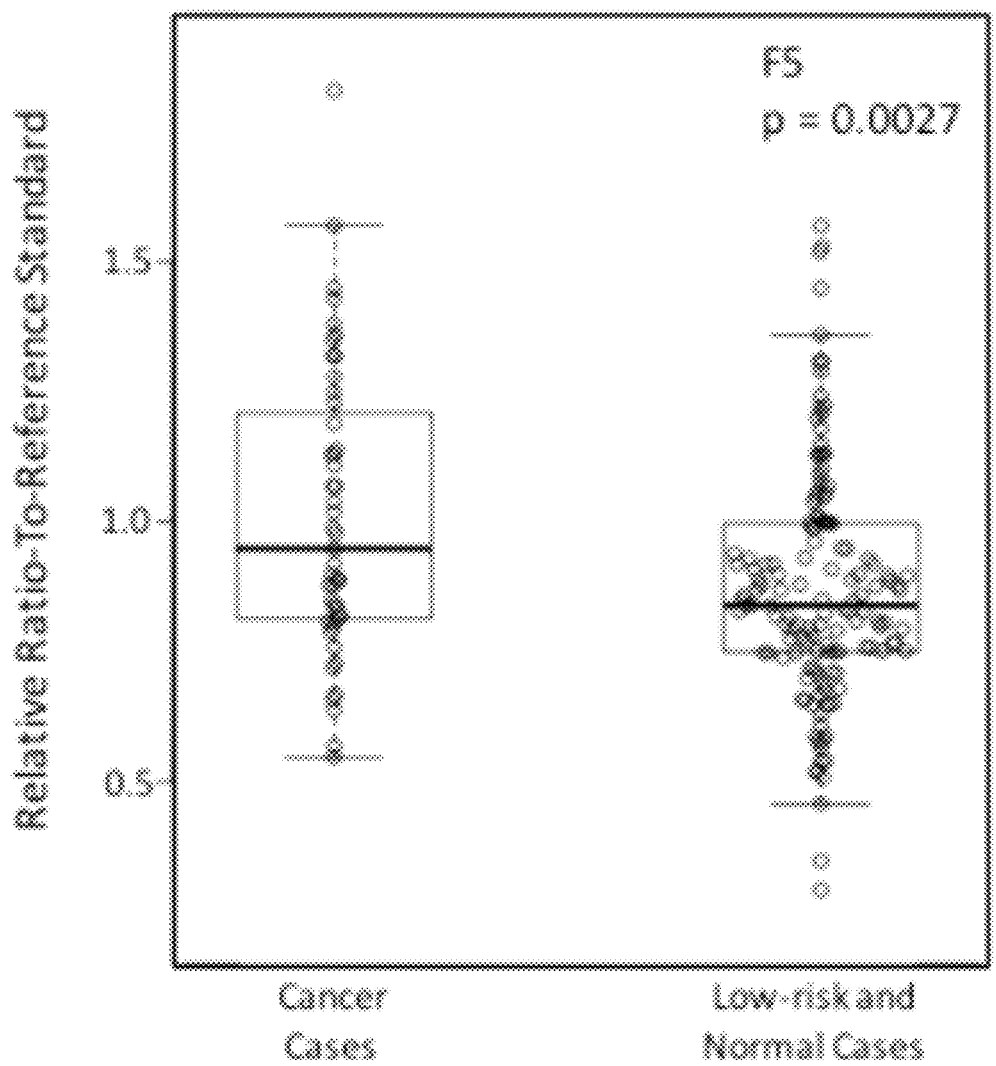
Figure 19A:
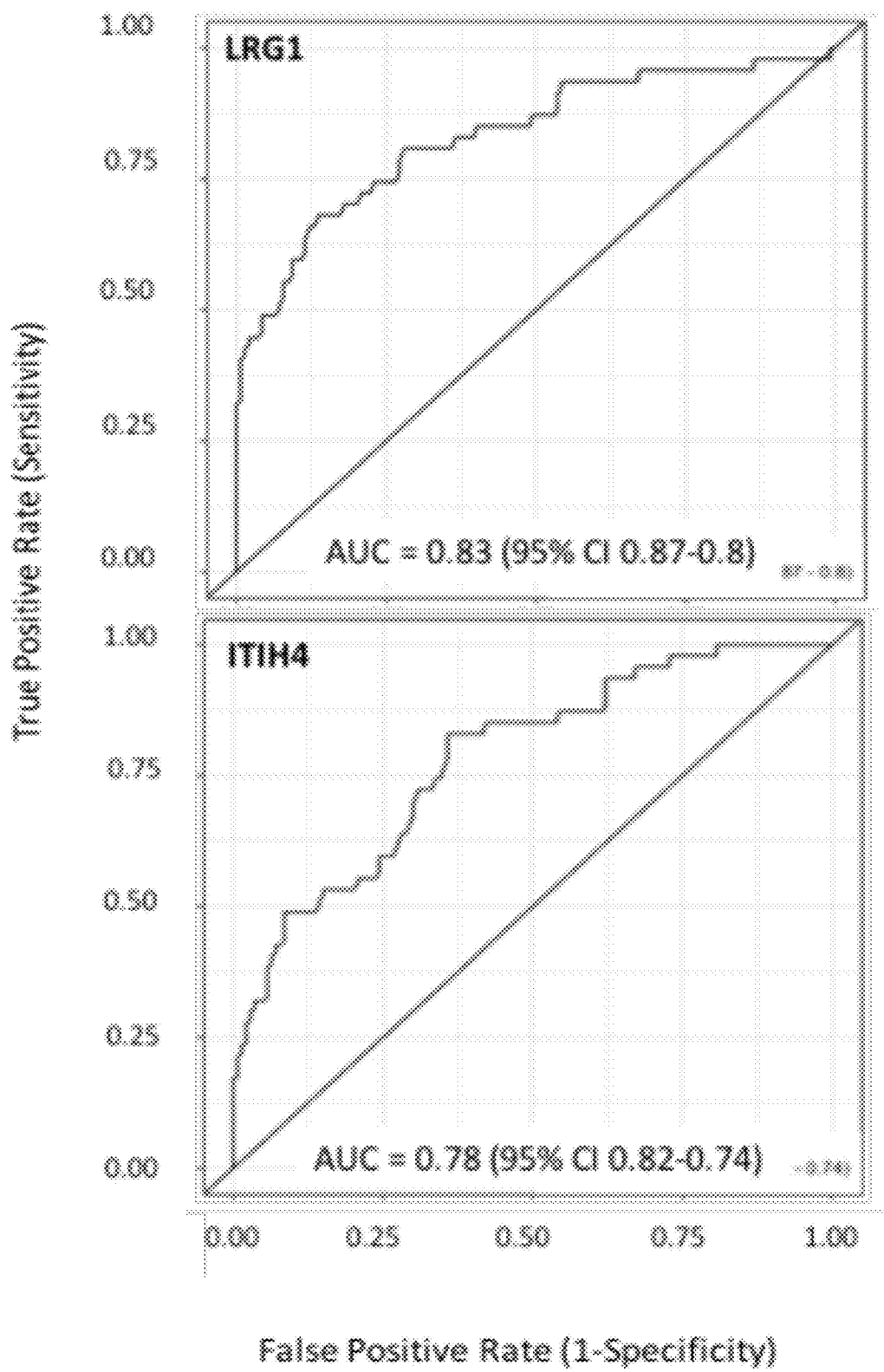
FIG. 19 illustrates the ROC curves for each of the upregulated proteins in pooled low-risk and normal colonoscopy cases ("Low-risk and Normal Cases"), compared to non-metastatic cancers ("Cancer Cases").
Figure 19B:
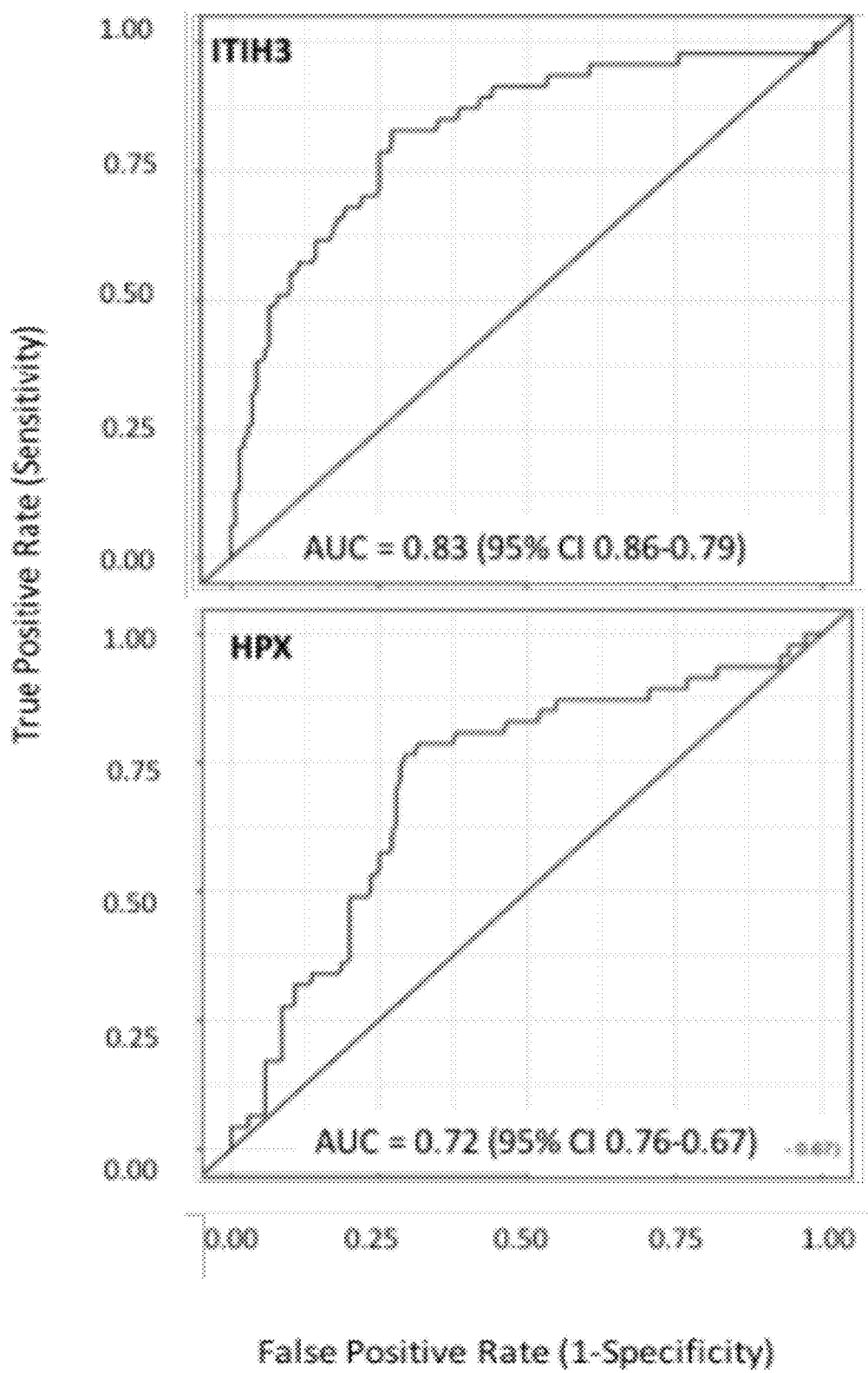
Figure 19C:
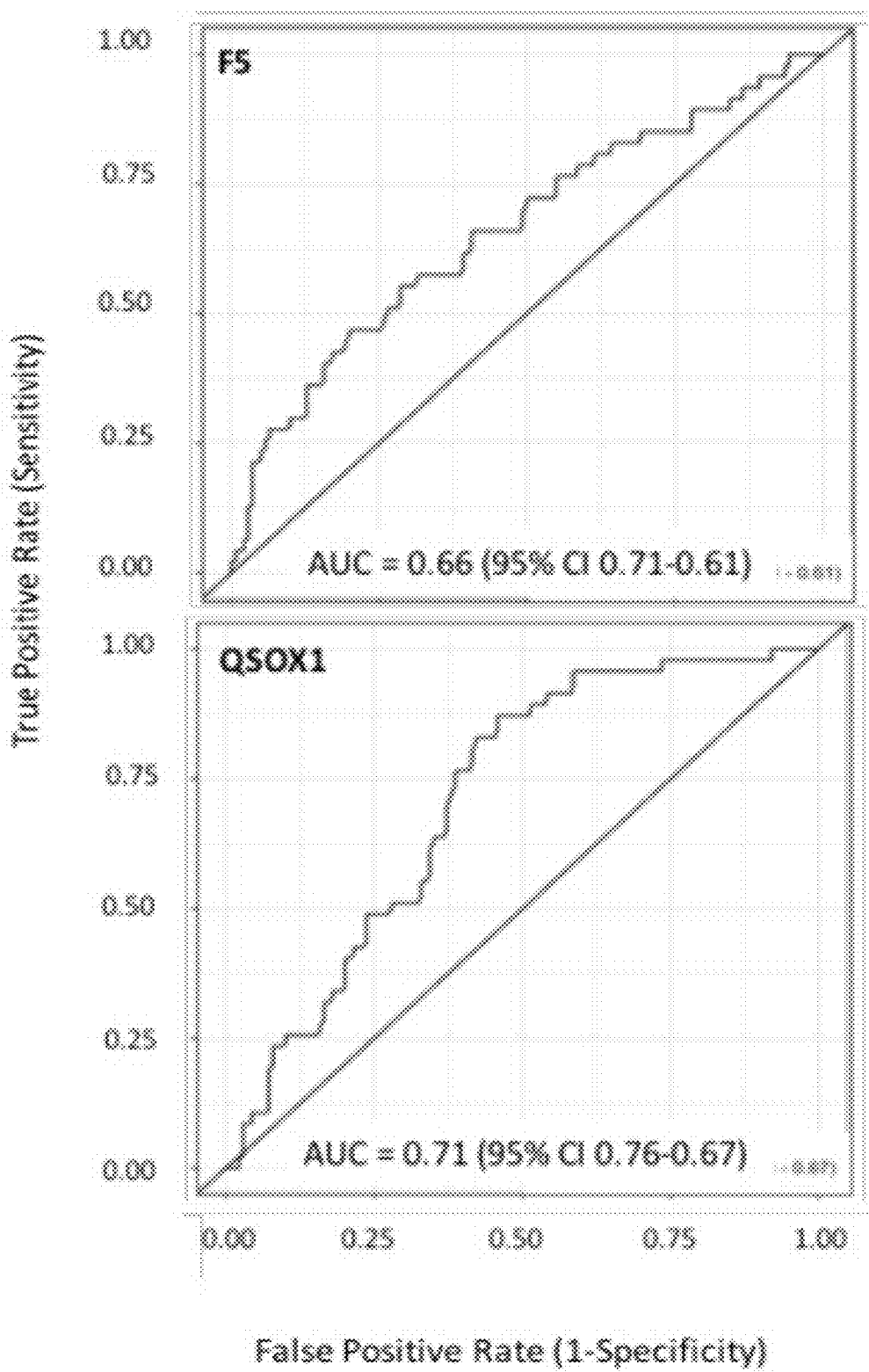
Figure 19D:
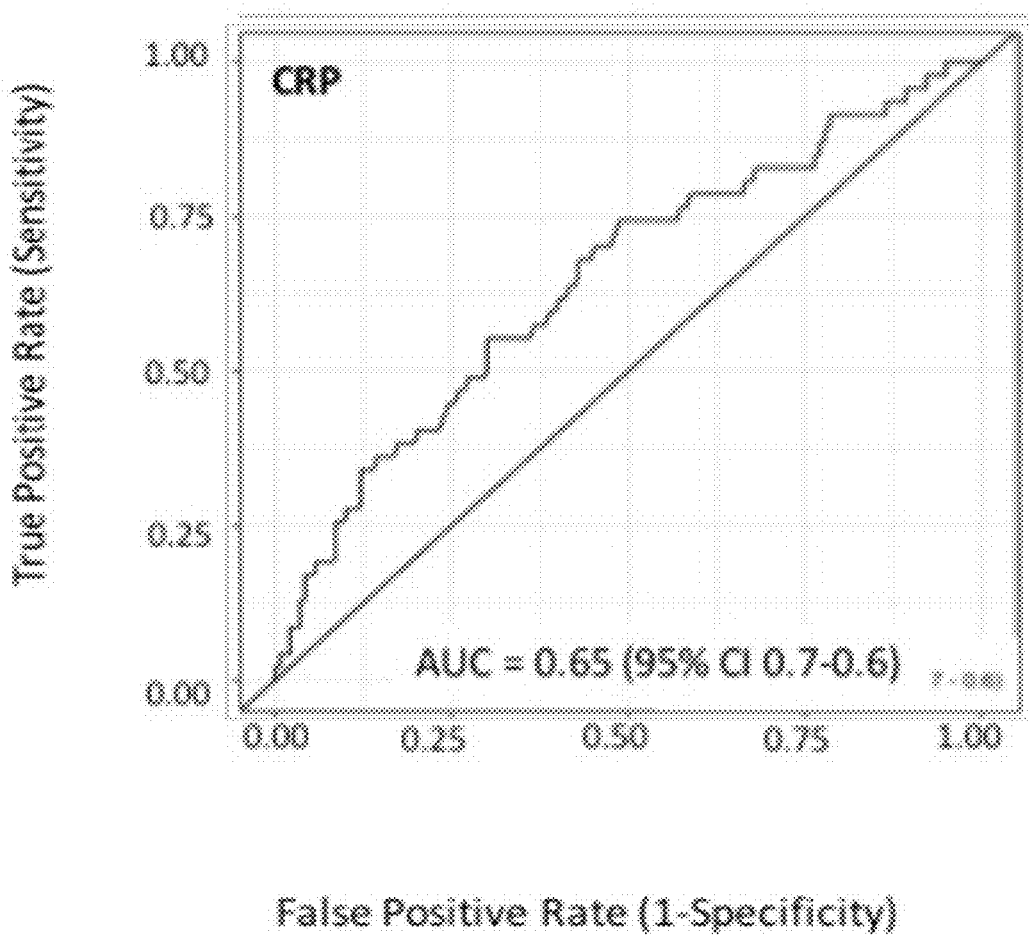
Figure 20A:
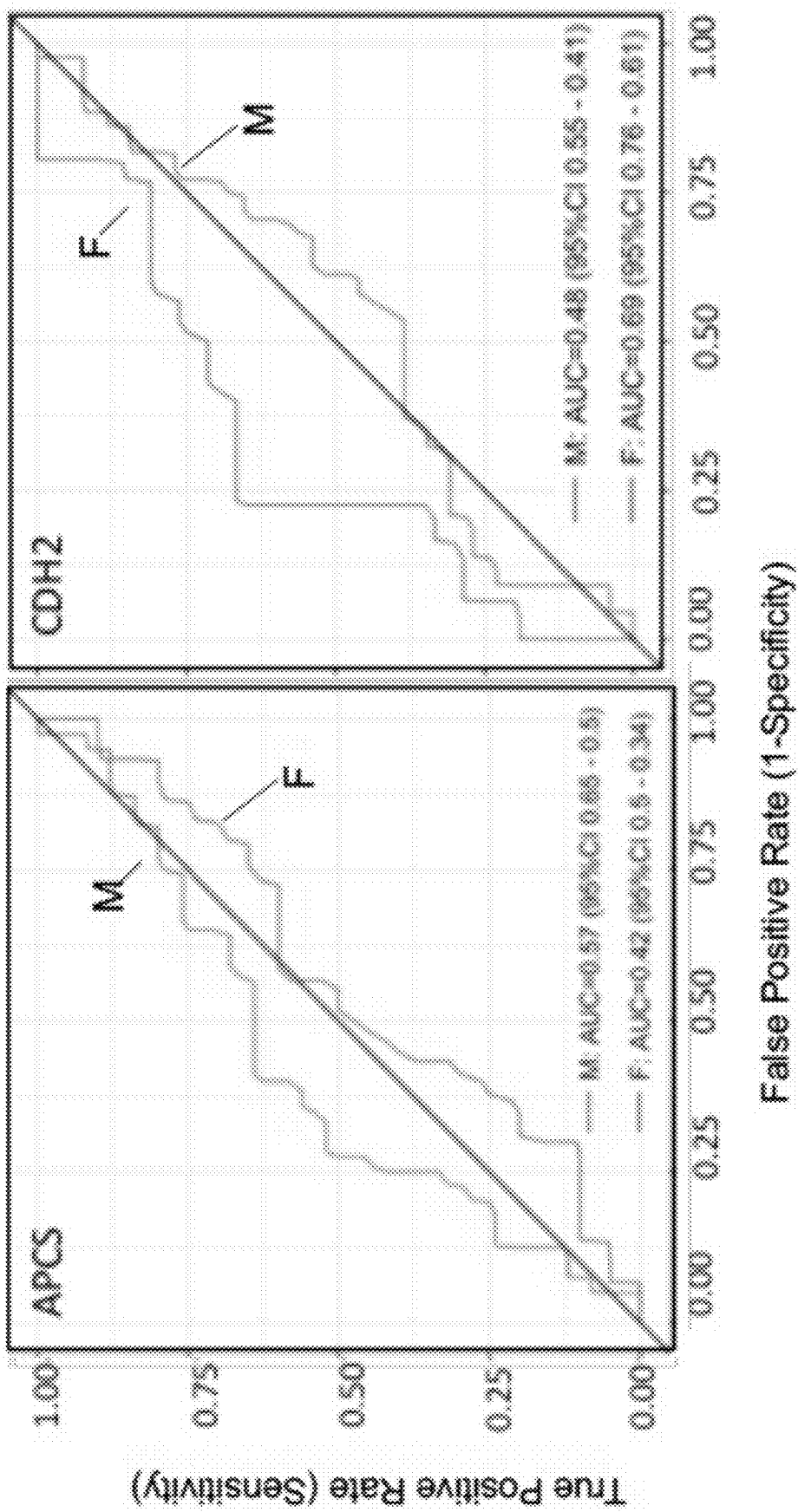
FIG. 20 illustrates ROC curves for the indicated biomarkers that show gender-related differences in sensitivity and specificity for proteins in pooled low-risk and normal colonoscopy cases (left panel) compared to non-metastatic cancers (right panels). The ROC curves are labeled "F" and "M" for females and males respectively.
Figure 20B:
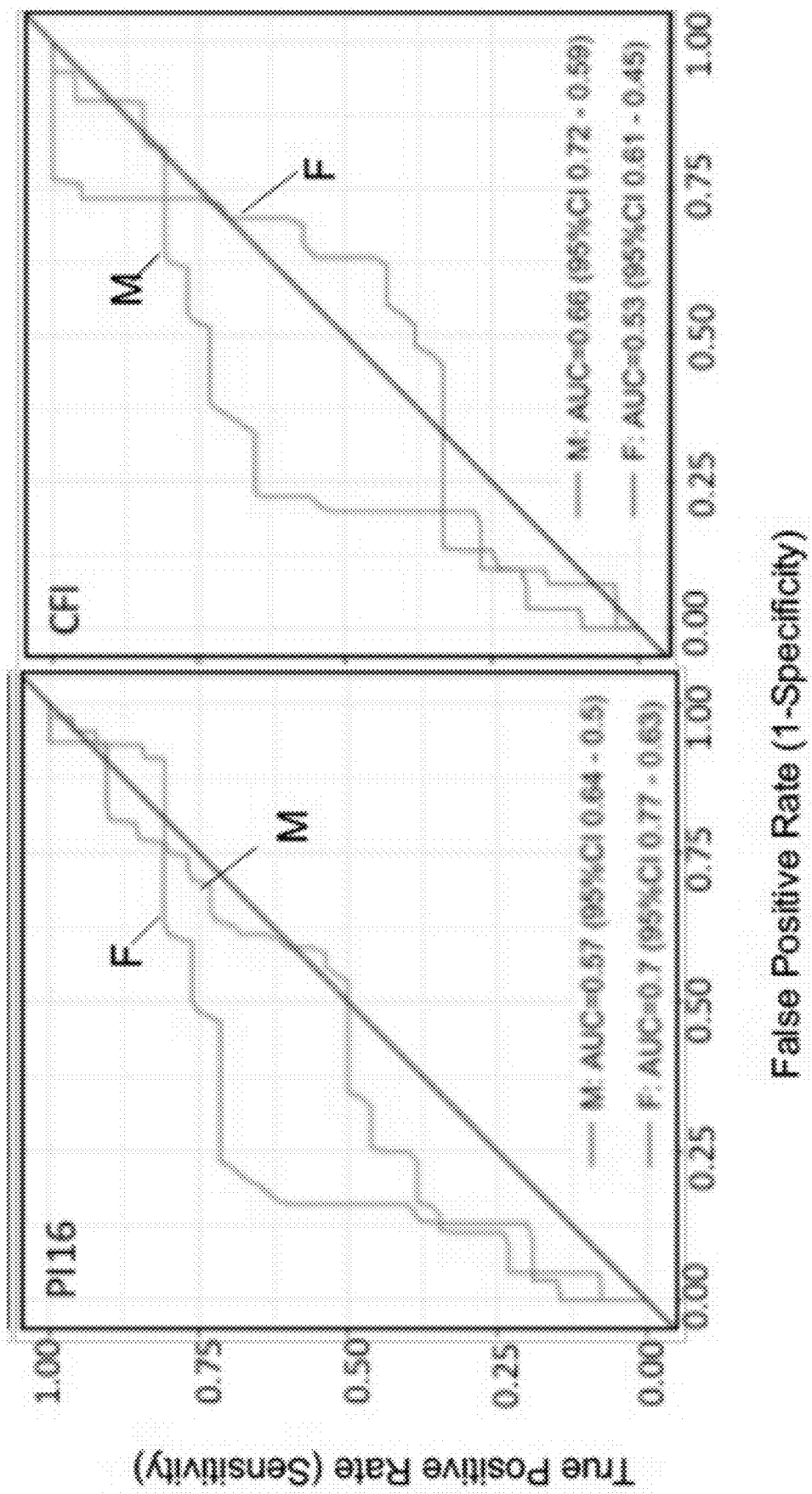
Figure 20C:
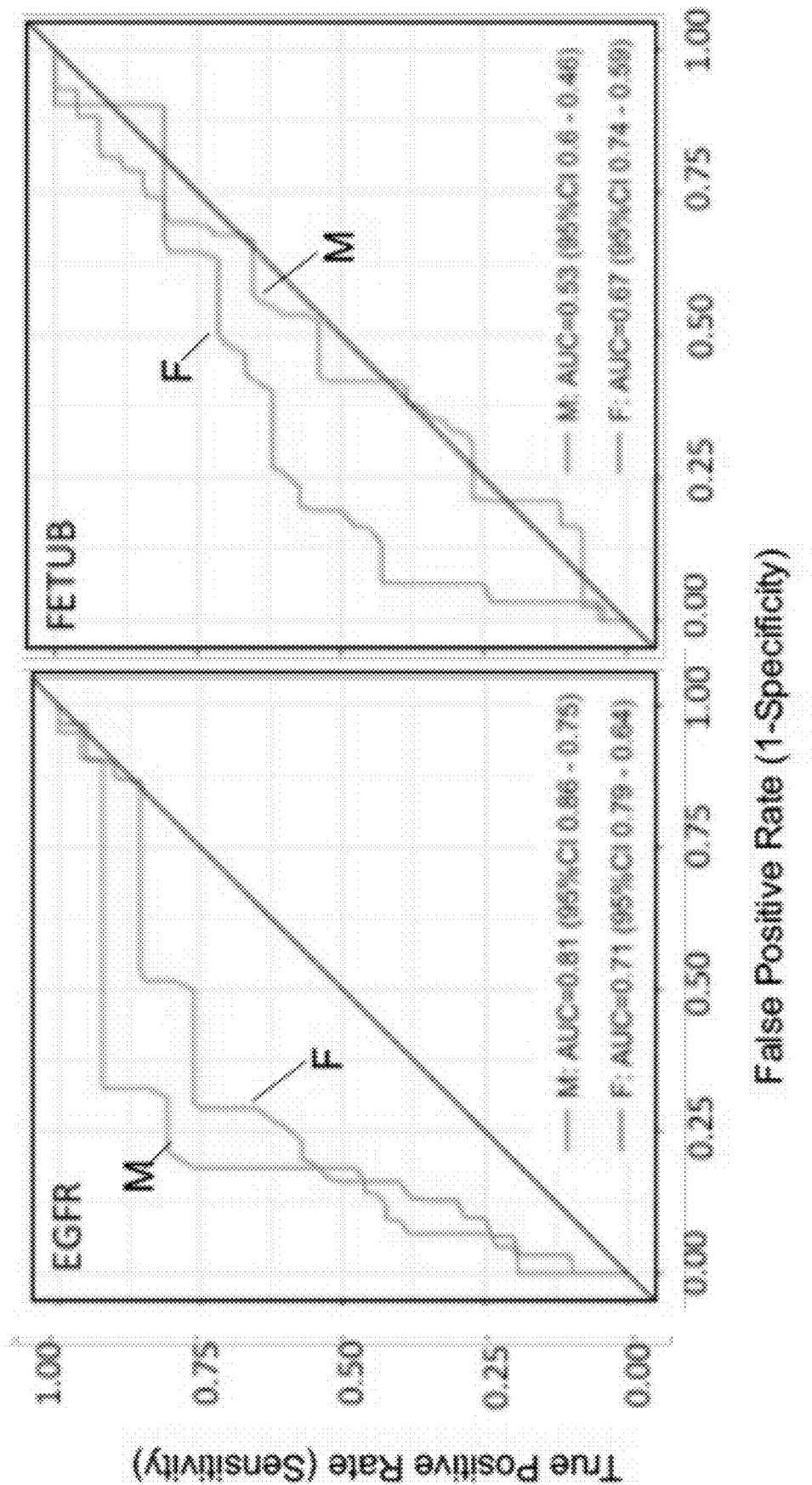
Figure 20D:
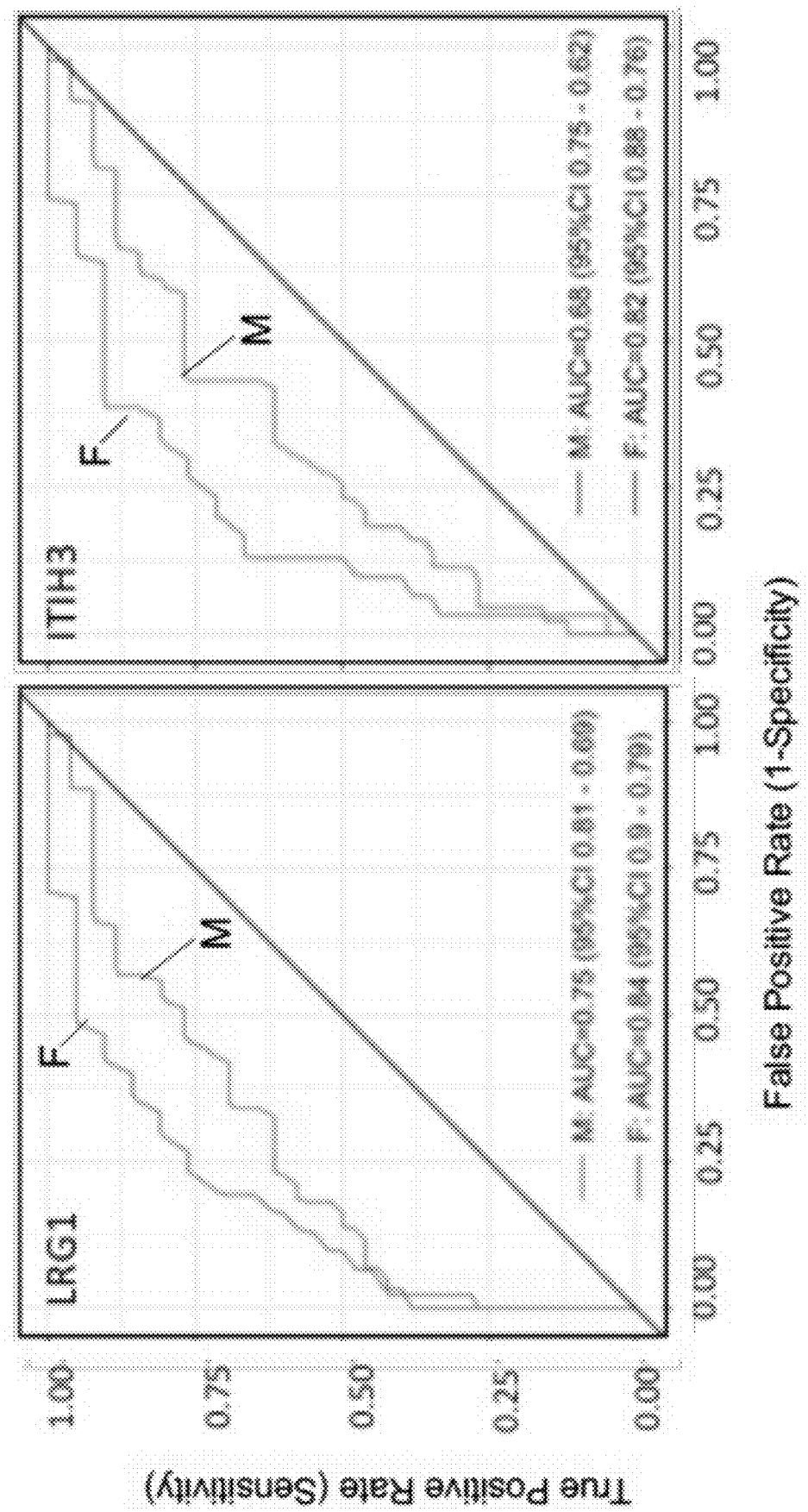

Biomarkers Provide Differentiation Between Colorectal Adenomas and Colorectal Carcinomas Patients with screening normal colonoscopies or low-risk adenomas were differentiated from colorectal cancer cases. An average of all non-metastatic colorectal cancers compared to low-risk cases and normal cases showed downregulation in EGFR, DPP4, CD44, PI16, and FETUB (FIG. 16, Table 6). ROC curves for these proteins (FIG. 17) indicate that EGFR has the highest sensitivity and specificity for predicting colorectal cancers while DPP4 and CD44 are also good predictors. LRG1, ITIH3, ITIH4, HPX, CRP, QSOX1, and F5 are upregulated in cancers compared to low-risk colonoscopy cases (FIG. 18, Table 6). Among all proteins analyzed, LRG1, ITIH3, and ITIH4 had the overall greatest sensitivity and specificity for predicting the presence of colorectal carcinomas as individual markers (FIG. 19).

TABLE 6a

Fold changes in protein biomarker expression within the compared experimental groups

| Comparison | EGFR | LRG1 | ITIH3 | ITIH4 | DPP4 | HPX | PI16 | F5 | CRP |
|---|---|---|---|---|---|---|---|---|---|
| Normal/Low-risk | 1.00 | 1.03 | 0.95 | 0.95 | 0.95 | 0.96 | 0.96 | 1.04 | 0.89 |
| Advanced Adenoma/Low-risk + Normal | 0.98 | 1.03 | 0.98 | 1.04 | 1.03 | 0.93 | 0.94 | 1.04 | 1.15 |
| Stage 1/Low-risk + Normal | 0.90 | 1.43 | 1.70 | 1.24 | 0.81 | 1.28 | 0.77 | 1.14 | 1.74 |
| Stage 2/Low-risk + Normal | 0.88 | 2.00 | 1.82 | 1.39 | 0.75 | 1.30 | 0.89 | 1.29 | 1.81 |
| Stage 3/Low-risk + Normal | 0.85 | 1.65 | 1.75 | 1.32 | 0.98 | 1.27 | 1.12 | 1.06 | 2.88 |
| All Cancer Cases/Low-risk + Normal | 0.88 | 1.64 | 1.75 | 1.30 | 0.84 | 1.28 | 0.89 | 1.16 | 2.05 |
| Stage 1/Advanced Adenoma | 0.92 | 1.38 | 1.73 | 1.20 | 0.79 | 1.37 | 0.82 | 1.10 | 1.51 |
| Stage 2/Advanced Adenoma | 0.89 | 1.94 | 1.85 | 1.34 | 0.73 | 1.40 | 0.95 | 1.24 | 1.58 |
| Stage 3/Advanced Adenoma | 0.87 | 1.60 | 1.78 | 1.27 | 0.95 | 1.37 | 1.19 | 1.02 | 2.50 |
| All Cancers/Advanced Adenoma | 0.90 | 1.59 | 1.78 | 1.26 | 0.81 | 1.38 | 0.95 | 1.11 | 1.78 |
| Stage 2/Stage 1 | 0.98 | 1.40 | 1.07 | 1.11 | 0.92 | 1.02 | 1.16 | 1.13 | 1.04 |

TABLE 6a-continued

Fold changes in protein biomarker expression within the compared experimental groups

| | | | | | | | | |
|---|---|---|---|---|---|---|---|---|
| Stage 3/Stage 1 | 0.95 | 1.15 | 1.03 | 1.06 | 1.20 | 0.99 | 1.46 | 0.93 | 1.65 |
| Stage 3/Stage 2 | 0.97 | 0.82 | 0.96 | 0.95 | 1.30 | 0.98 | 1.26 | 0.82 | 1.58 |
| Stage 3/ Stages 1&2 Combined | 0.96 | 1.00 | 1.00 | 1.01 | 1.23 | 0.99 | 1.38 | 0.89 | 1.63 |

| Comparison | CD44 | FETUB | QSOX1 | CDH2 | SOD3 | APCS | CFI | GC (VitD) |
|---|---|---|---|---|---|---|---|---|
| Normal/Low-risk | 1.00 | 0.96 | 1.07 | 1.16 | 1.26 | 0.95 | 0.95 | 0.98 |
| Advanced Adenoma/Low-risk + Normal | 0.97 | 0.98 | 0.99 | 0.93 | 0.90 | 1.06 | 1.04 | 0.99 |
| Stage 1/Low-risk + Normal | 0.92 | 0.80 | 1.18 | 0.91 | 0.86 | 1.04 | 1.00 | 1.01 |
| Stage 2/Low-risk + Normal | 0.90 | 0.93 | 1.25 | 1.04 | 1.03 | 1.10 | 1.06 | 1.06 |
| Stage 3/Low-risk + Normal | 0.73 | 0.85 | 1.11 | 0.75 | 0.77 | 0.98 | 1.02 | 1.07 |
| All Cancer Cases/Low-risk + Normal | 0.86 | 0.85 | 1.18 | 0.90 | 0.88 | 1.04 | 1.02 | 1.04 |
| Stage 1/Advanced Adenoma | 0.94 | 0.82 | 1.20 | 0.97 | 0.96 | 0.98 | 0.96 | 1.02 |
| Stage 2/Advanced Adenoma | 0.92 | 0.95 | 1.27 | 1.11 | 1.15 | 1.03 | 1.03 | 1.08 |
| Stage 3/Advanced Adenoma | 0.75 | 0.87 | 1.13 | 0.80 | 0.85 | 0.92 | 0.99 | 1.08 |
| All Cancers/Advanced Adenoma | 0.88 | 0.87 | 1.20 | 0.97 | 0.98 | 0.98 | 0.99 | 1.05 |
| Stage 2/Stage 1 | 0.98 | 1.17 | 1.06 | 1.15 | 1.20 | 1.05 | 1.07 | 1.06 |
| Stage 3/Stage 1 | 0.80 | 1.07 | 0.94 | 0.83 | 0.89 | 0.94 | 1.03 | 1.06 |
| Stage 3/Stage 2 | 0.81 | 0.92 | 0.88 | 0.72 | 0.74 | 0.89 | 0.96 | 1.01 |
| Stage 3/Stages 1&2 Combined | 0.80 | 1.01 | 0.92 | 0.78 | 0.83 | 0.92 | 1.00 | 1.04 |

Mann-Whitney P-value cut-off for a Benjamini Hochberg False discovery rate of $q \leq 0.05$ is a $p \leq 0.01352$. All Bolded ratios have a P-value that is 0.01352 or lower.

TABLE 6b

Exact Mann-Whitney P-values for the fold changes in protein expression shown in 6a.

| Comparison | EGFR P-Values | LRG1 P-Values | ITIH3 P-Values | ITIH4 P-Values | DPP4 P-Values | HPX P-Values | PI16 P-Values | F5 P-Values | CRP P-Values |
|---|---|---|---|---|---|---|---|---|---|
| Normal/Low-risk | 0.83366 | 0.68916 | 0.77948 | 0.267 | 0.9442 | 0.5892 | 0.71884 | 0.44726 | 0.98404 |
| Advanced Adenoma/Low-risk + Normal | 0.16152 | 0.74896 | 0.32218 | 0.50926 | 0.41794 | 0.28914 | 0.6818 | 0.44726 | 0.09102 |
| Stage 1/Low-risk + Normal | 0.0001 | 0.000007 | 0.000001 | 0.00008 | 0.00398 | 0.00096 | 0.00298 | 0.08012 | 0.02034 |
| Stage 2/Low-risk + Normal | 0.0007 | 0.000002 | 0.000002 | 0.000008 | 0.00138 | 0.0139 | 0.02382 | 0.00086 | 0.09492 |
| Stage 3/Low-risk + Normal | 0.00328 | 0.00086 | 0.00318 | 0.0018 | 0.08914 | 0.01428 | 0.6672 | 0.52218 | 0.00614 |
| All Cancer Cases/Low-risk + Normal | 5.82E−08 | 1.92E−10 | 1.53E−11 | 1.20E−09 | 0.000038 | 0.000011 | 0.00152 | 0.0027 | 0.00042 |
| Stage 1/Advanced Adenoma | 0.01016 | 0.000093 | 0.000007 | 0.00124 | 0.01552 | 0.000056 | 0.00634 | 0.2113 | 0.1936 |
| Stage 2/Advanced Adenoma | 0.01352 | 0.000006 | 0.000008 | 0.00008 | 0.00672 | 0.00174 | 0.03078 | 0.0088 | 0.42952 |
| Stage 3/Advanced Adenoma | 0.02642 | 0.00148 | 0.00222 | 0.00672 | 0.14706 | 0.00318 | 0.76418 | 0.83366 | 0.03572 |
| All Cancers/Advanced Adenoma | 0.0003 | 8.24E−09 | 1.46E−09 | 9.55E−07 | 0.00096 | 3.17E−07 | 0.00596 | 0.04338 | 0.04136 |
| Stage 2/Stage 1 | 0.70394 | 0.0278 | 0.56192 | 0.15272 | 0.4009 | 0.61006 | 0.92828 | 0.18352 | 0.79486 |
| Stage 3/Stage 1 | 0.6818 | 0.8181 | 0.70394 | 0.5552 | 0.6672 | 0.89656 | 0.18684 | 0.61708 | 0.4413 |
| Stage 3/Stage 2 | 0.97606 | 0.242 | 0.4009 | 0.5287 | 0.28914 | 0.93624 | 0.30302 | 0.08726 | 0.2113 |
| Stage 3/Stages 1&2 Combined | 0.76418 | 0.72634 | 0.5157 | 0.9124 | 0.4354 | 0.89656 | 0.29372 | 0.26272 | 0.27134 |

| Comparison | CD44 P-Values | FETUB P-Values | QSOX1 P-Values | CDH2 P-Values | SOD3 P-Values | APCS P-Values | CFI P-Values | GC (VitD) P-Values |
|---|---|---|---|---|---|---|---|---|
| Normal/Low-risk | 0.75656 | 0.56192 | 0.17384 | 0.06724 | 0.07186 | 0.35238 | 0.32218 | 0.33204 |
| Advanced Adenoma/Low-risk + Normal | 0.35758 | 0.5157 | 0.70394 | 0.32218 | 0.99202 | 0.50926 | 0.4902 | 0.61708 |
| Stage 1/Low-risk + Normal | 0.06288 | 0.0035 | 0.0083 | 0.62414 | 0.1936 | 0.81034 | 0.99202 | 0.88076 |
| Stage 2/Low-risk + Normal | 0.14156 | 0.58232 | 0.00054 | 0.32218 | 0.36282 | 0.68916 | 0.4354 | 0.23014 |
| Stage 3/Low-risk + Normal | 0.000013 | 0.06288 | 0.07186 | 0.05744 | 0.06432 | 0.99202 | 0.52218 | 0.1141 |
| All Cancer Cases/Low-risk + Normal | 0.00016 | 0.00288 | 0.000023 | 0.4777 | 0.20408 | 0.96012 | 0.50286 | 0.23014 |
| Stage 1/Advanced Adenoma | 0.20054 | 0.01108 | 0.00386 | 0.97606 | 0.19706 | 0.99202 | 0.65272 | 0.9124 |
| Stage 2/Advanced Adenoma | 0.27134 | 0.8181 | 0.0002 | 0.15854 | 0.3125 | 0.63122 | 0.6672 | 0.17384 |
| Stage 3/Advanced Adenoma | 0.00024 | 0.11184 | 0.05238 | 0.1936 | 0.06876 | 0.75656 | 0.97606 | 0.1031 |
| All Cancers/Advanced Adenoma | 0.00398 | 0.0198 | 0.000021 | 0.92034 | 0.25428 | 0.72634 | 0.96012 | 0.16758 |
| Stage 2/Stage 1 | 0.95216 | 0.22628 | 0.28014 | 0.25428 | 0.18352 | 0.9442 | 0.4965 | 0.267 |
| Stage 3/Stage 1 | 0.0151 | 0.28014 | 0.1902 | 0.28014 | 0.5157 | 0.7414 | 0.77182 | 0.21498 |
| Stage 3/Stage 2 | 0.0601 | 0.42952 | 0.1096 | 0.04444 | 0.08914 | 0.81034 | 0.4654 | 0.93624 |
| Stage 3/Stages 1&2 Combined | 0.01242 | 0.71138 | 0.1902 | 0.09894 | 0.22246 | 0.72634 | 0.88866 | 0.37346 |

Mann-Whitney P-value cut-off for a Benjamini Hochberg False discovery rate of $q \leq 0.05$ is a $p \leq 0.01352$. Bolded are P-values of 0.01352 or lower that fall within the false discovery rate calculation.

Multi-Marker Panels have the Capability of Increasing Sensitivity and Specificity of Colorectal Cancer Detection for Screening Purposes.

Figure 21:
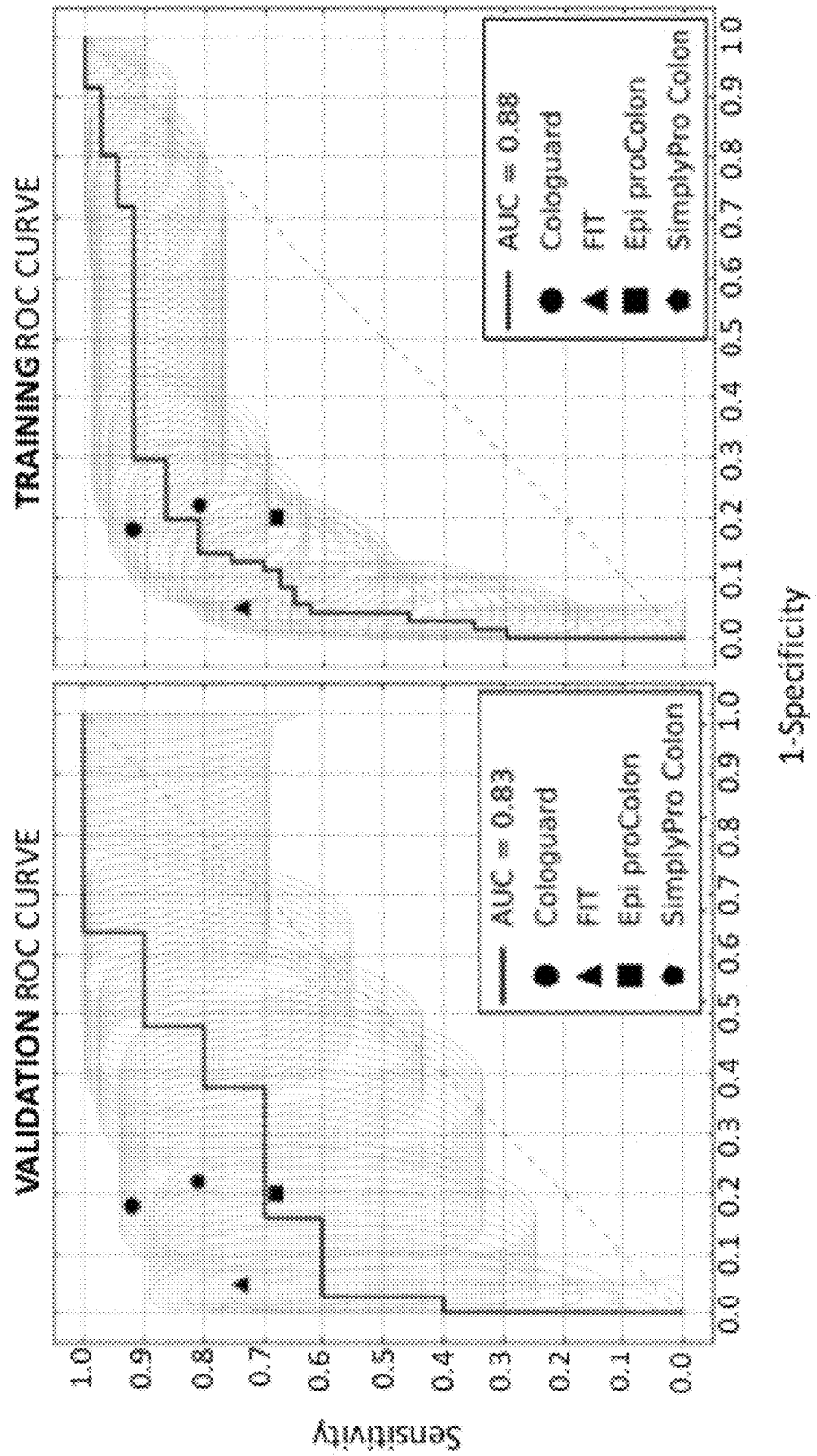
FIG. 21 illustrates five-marker panel ROC curves using logistic regression analysis. The left-most curve illustrates validation data for the five markers: CD44, DPP4, EGFR, ITIH3, and LRG1. The training curve for the same data is the right-most ROC curve. Gray spheres represent the confidence interval. Included in the ROC curve are set sensitivity and specificity points for commercially available screening tests for CRC.
Figure 22:
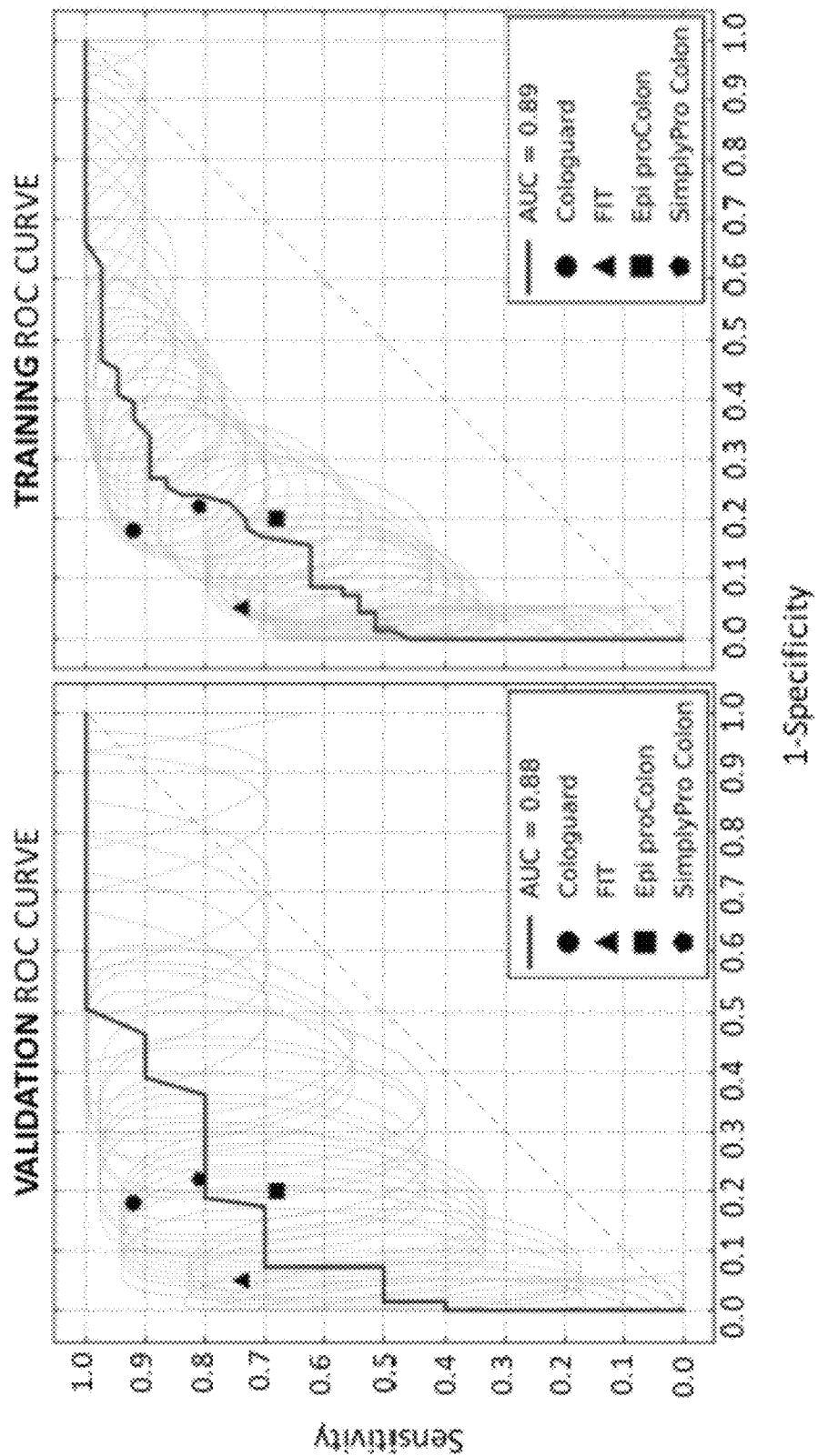
FIG. 22 illustrates five-marker panel ROC curves using extra trees regression analysis. The left-most curve illustrates validation data for the five markers: CD44, DPP4, EGFR, ITIH3, and LRG1. The training curve for the same data is the right-most ROC curve. Gray spheres represent the confidence interval. Included in the ROC curve are set sensitivity and specificity points for commercially available screening tests for CRC.

Sensitivity and specificity can be increased by using a multi-marker panel. Using several different machine-learning methods, all of the biomarkers were tested as potential candidates for a biomarker panel to maximize sensitivity and specificity for detecting colorectal cancer compared to low-risk patients. A five-marker protein panel comprising CD44, DPP4, EGFR, ITIH3, and LRG1 was identified using two different machine-learning algorithms as the most optimal panel for detecting cancer compared to low-risk and normal cases (FIGS. 21 and 22). First a training set of 37 cancers and 71 low-risk adenoma and normal cases was used to train the algorithms. Second, 10 cancers and 69 low-risk adenoma and normal cases were used to validate the algorithm after training. Confidence regions are represented by gray spheres and were calculated according to Tilbury J B, Van Eetvelt P W, Garibaldi J M, Curnow J S, Ifeachor E C. Receiver operating characteristic analysis for intelligent medical systems—a new approach for finding confidence intervals. IEEE Trans Biomed Eng. 2000; 47(7):952-63. doi: 10.1109/10.846690. PubMed PMID: 10916267. AUCs for both the logistic regression and extra trees training sets were close to 0.9 while the validation set for extra trees was 0.88, substantially higher than any individual marker performed by logistic regression analysis. Importantly, the multi-marker panels increased the overall specificity to levels competitive with existing screening tools for colorectal cancer.

Figure 23A:
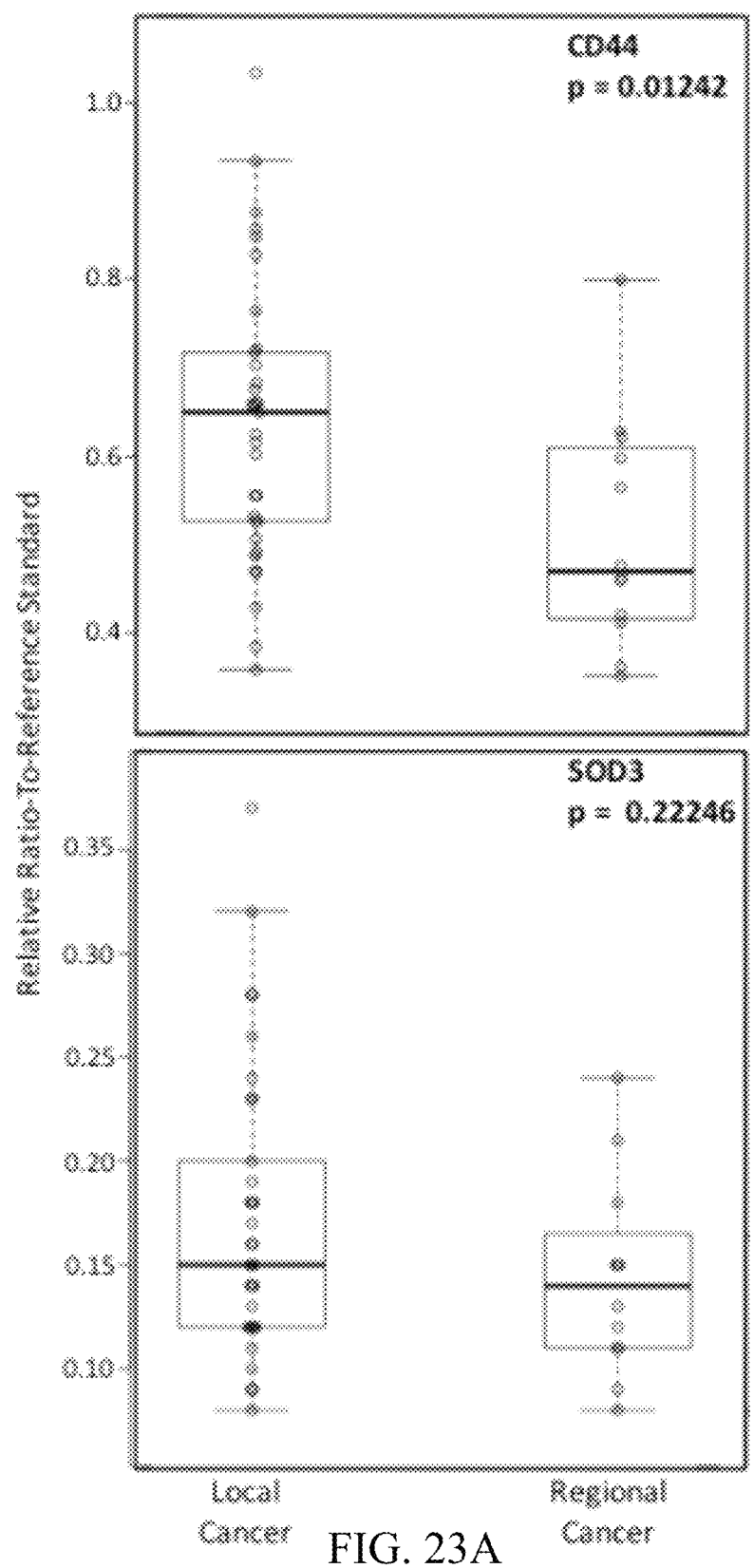
FIG. 23 shows relative ratio-to-reference standard data for the indicated biomarkers in non-metastatic cancer with ("Regional Cancer") and without ("Local Cancer") regional lymph node invasion. Stage 3 is characterized as having one or more infected regional lymph nodes. Each circle on the dot plots represents a single patient case.
Figure 23B:
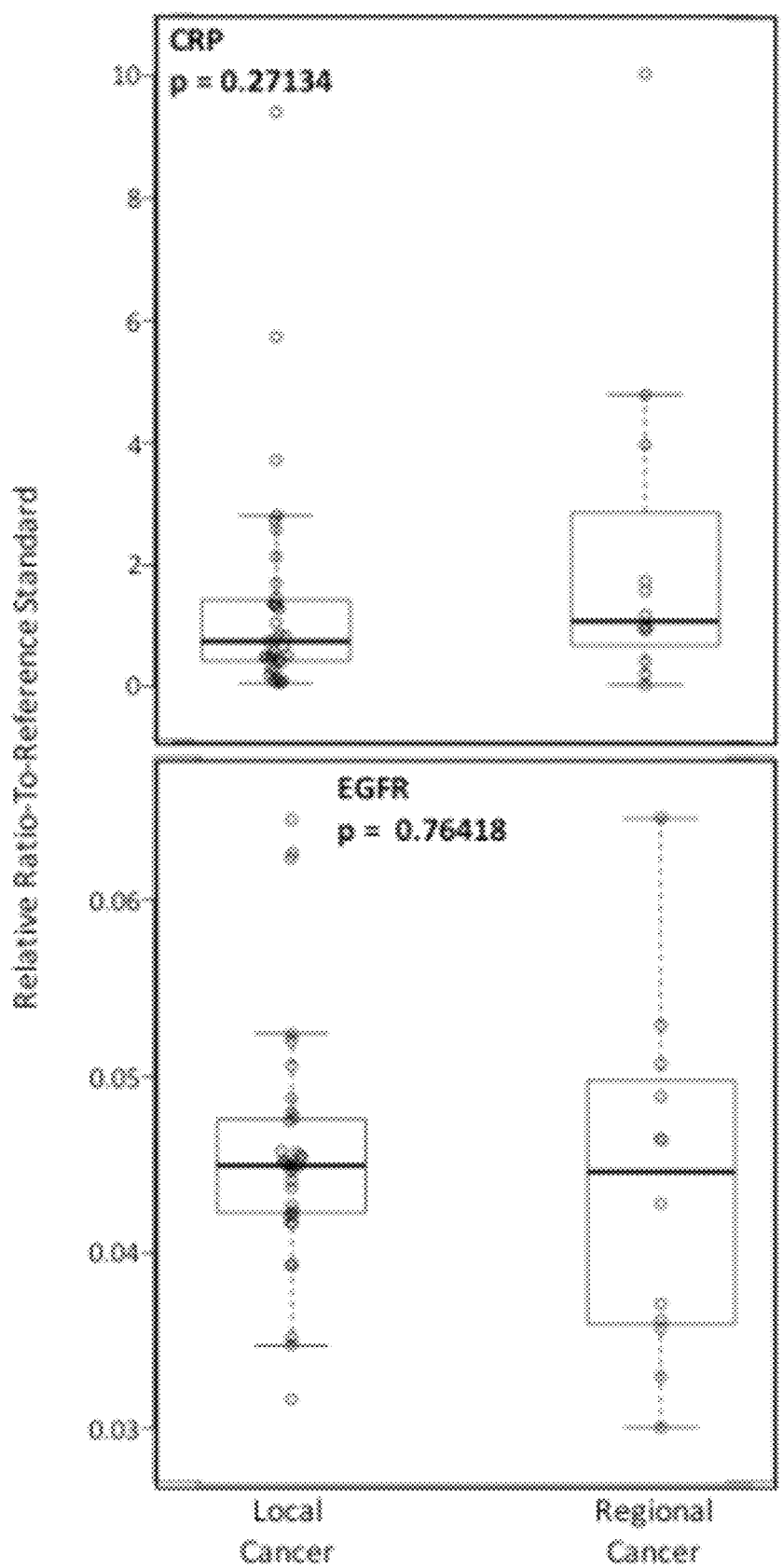
Figure 24:
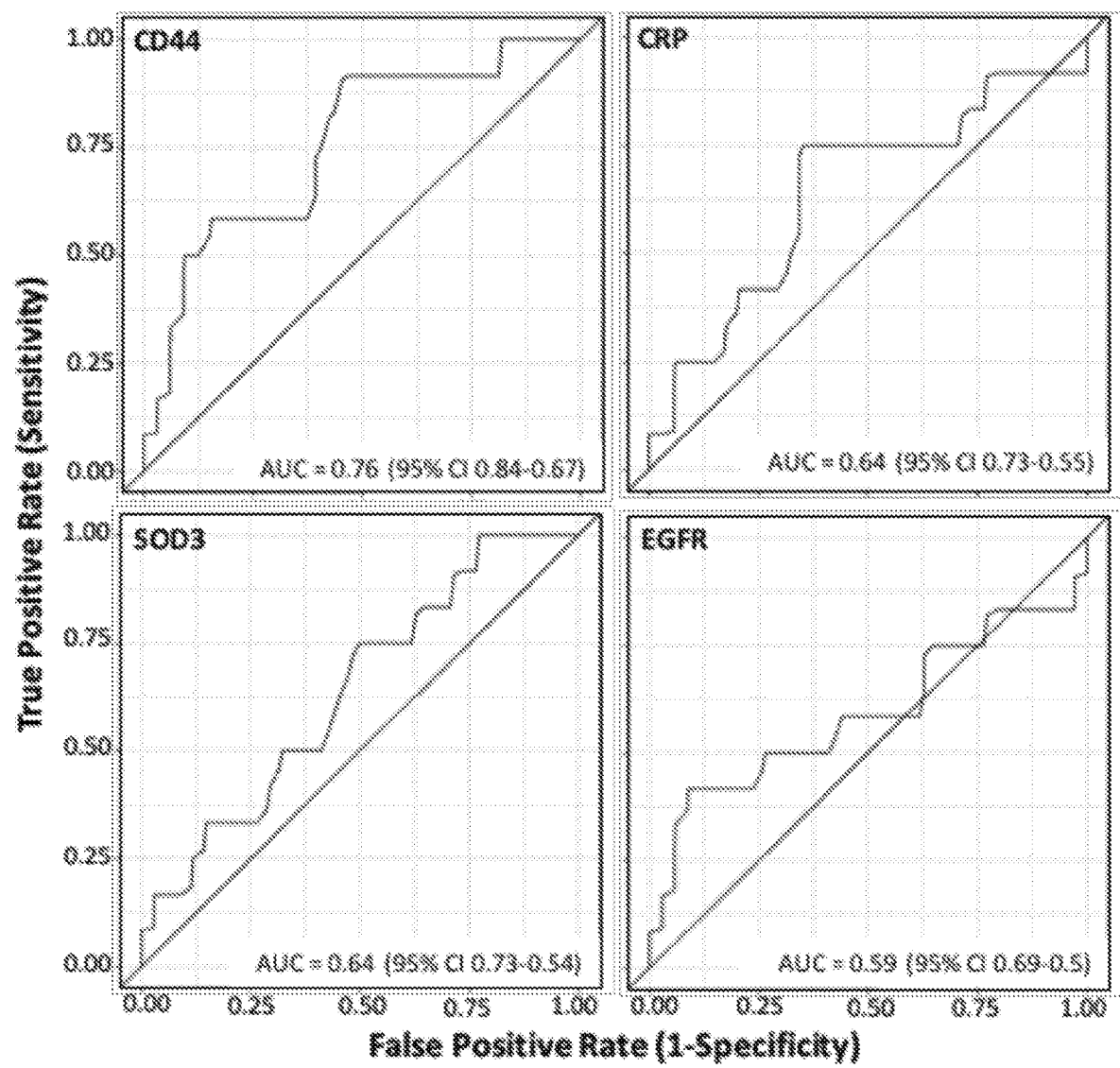
FIG. 24 shows sensitivity versus specificity ROC curves for the indicated biomarkers in patient cases with affected regional lymph nodes compared to non-metastatic cancer patients.

Biomarkers Allow for Identification of Regional Lymph Node Invasion in Cancer Stages Biomarkers were tested for their ability to differentiate early-stage cancers (stages 1 and 2) and regional lymph node invasion (stage 3) (FIG. 23, Table 6). AUCs for the individual markers (FIG. 24) show predictability for identifying regional lymph node presence with CD44 showing the greatest sensitivity and specificity for stage 3 CRC.

Figure 25:
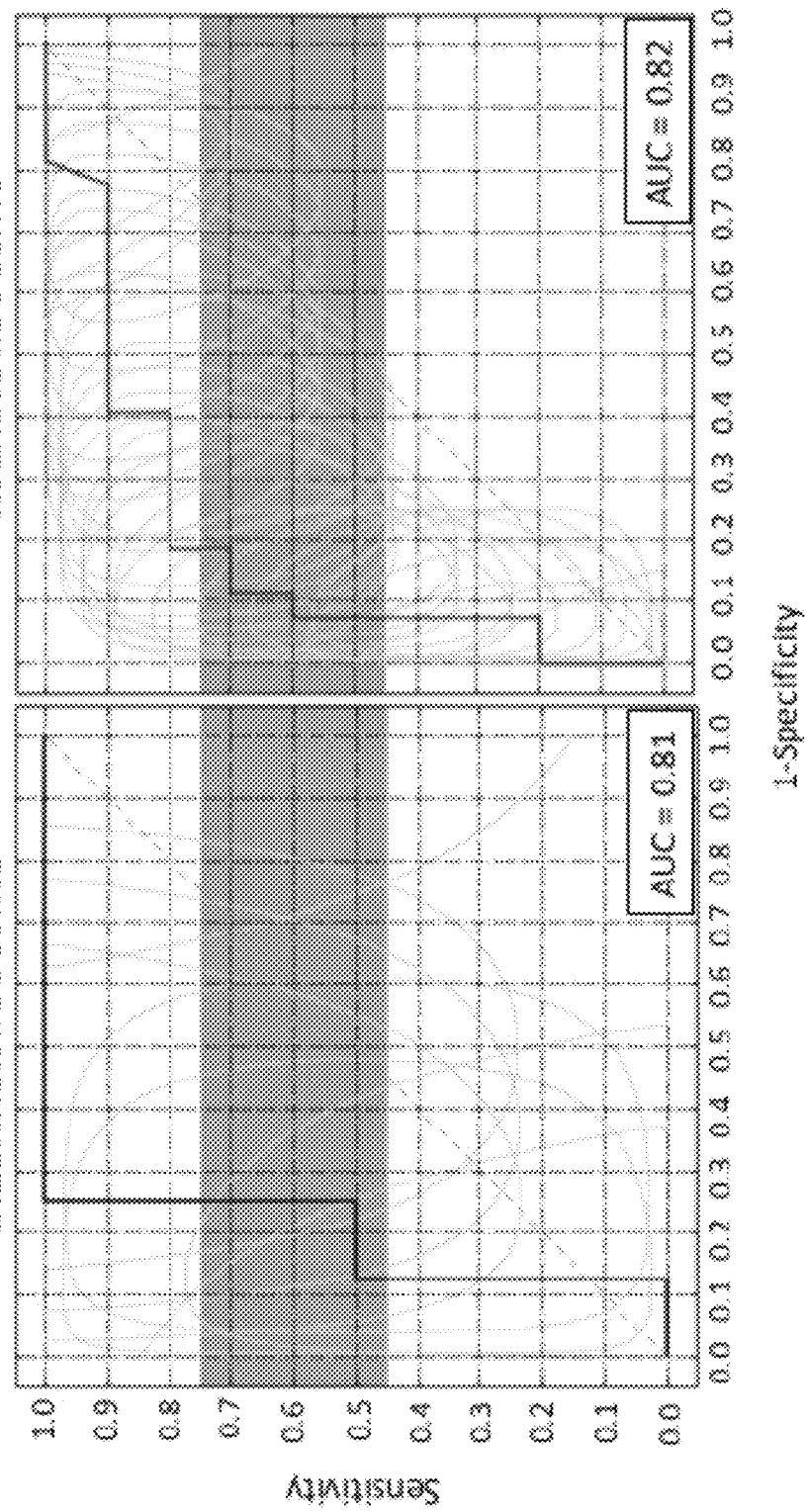
FIG. 25 illustrates the ROC curves of a biomarker panel comprising the indicated biomarkers capable of predicting the presence of regional lymph node involvement compared to localized non-metastatic cancer patients.

Using a Random Forest regression model, a five-biomarker panel of CD44, CRP, DPP4, ITIH3, and VITD (GC) was identified with sensitivity and specificity among the 47 patients analyzed (FIG. 25). Gray spheres represent overall confidence throughout the ROC curve while the purple box represents a target confidence range for identifying regional lymph nodes. The training data consisted of 10 stage 3 cancers and 27 stage for 2 cancers while the validation data consisted of 2 stage 3 cancers and 8 stage 1 or 2 cancers.

Biomarker Expression in Pre-Polypectomy Compared to Post-Polypectomy

For each patient that provided a pre- and post-polypectomy sample, a ratio of pre-/post-polypectomy biomarker expression was determined. The protein biomarkers tested comprise leucine-rich alpha-2-glycoprotein, peptidase inhibitor 16, CD44, cadherin 2, C-reactive protein, dipeptidyl peptidase 4, inter-alpha trypsin inhibitor, heavy chain H4, inter-alpha trypsin inhibitor, heavy chain H3, coagulation factor V, epidermal growth factor receptor, Fetuin-B, hemopexin, serum amyloid P component, vitamin D binding protein, complement factor I, superoxide dismutase 3, and quiescin sulfhydryl oxidase 1, thrombospondin-4, and vitronectin. A protein was defined as reverting toward normal levels post-polypectomy if the following were true (FIG. 6):

1. If the pre-polypectomy sample is upregulated from normal levels, then the post-polypectomy ratio-to-reference standard should be lower than the pre-polypectomy ratio-to-reference standard. Therefore, the ratio of pre-/post-polypectomy is greater than 1.
2. If the pre-polypectomy sample is downregulated from normal levels, then the post-polypectomy ratio-to-reference standard should be higher than the pre-polypectomy ratio-to-reference standard. Therefore the ratio of pre-/post-polypectomy is less than 1.

Figure 26:
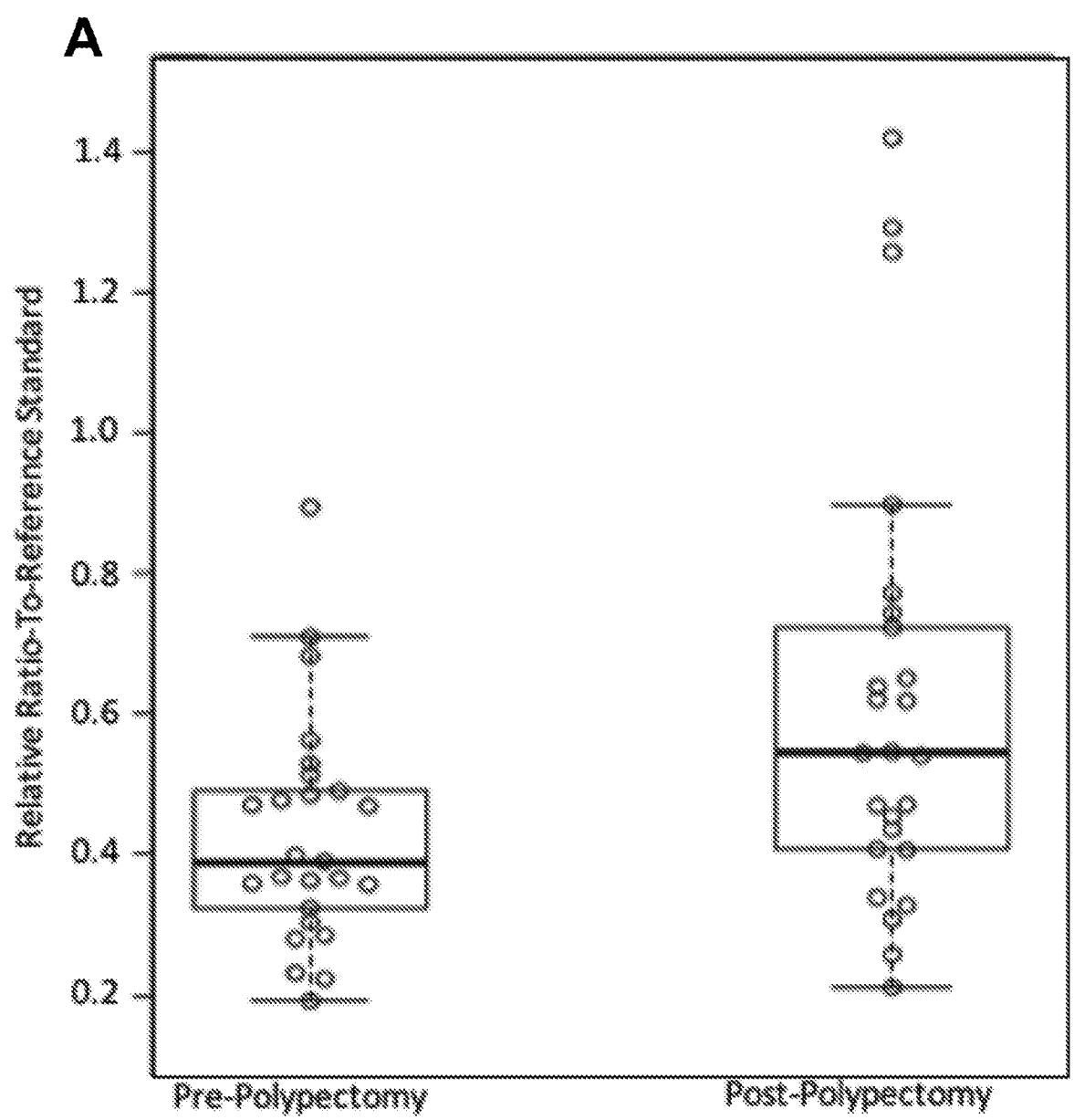
FIG. 26 shows PI16 biomarker expression before and after polypectomy for adenomas in general (FIG. 25A) and for adenomas divided by risk of developing into cancer (FIG. 25B). In the dot plot shown in FIG. 25A, each circle in the indicated category on the x-axis represents one patient.
Figure 26:
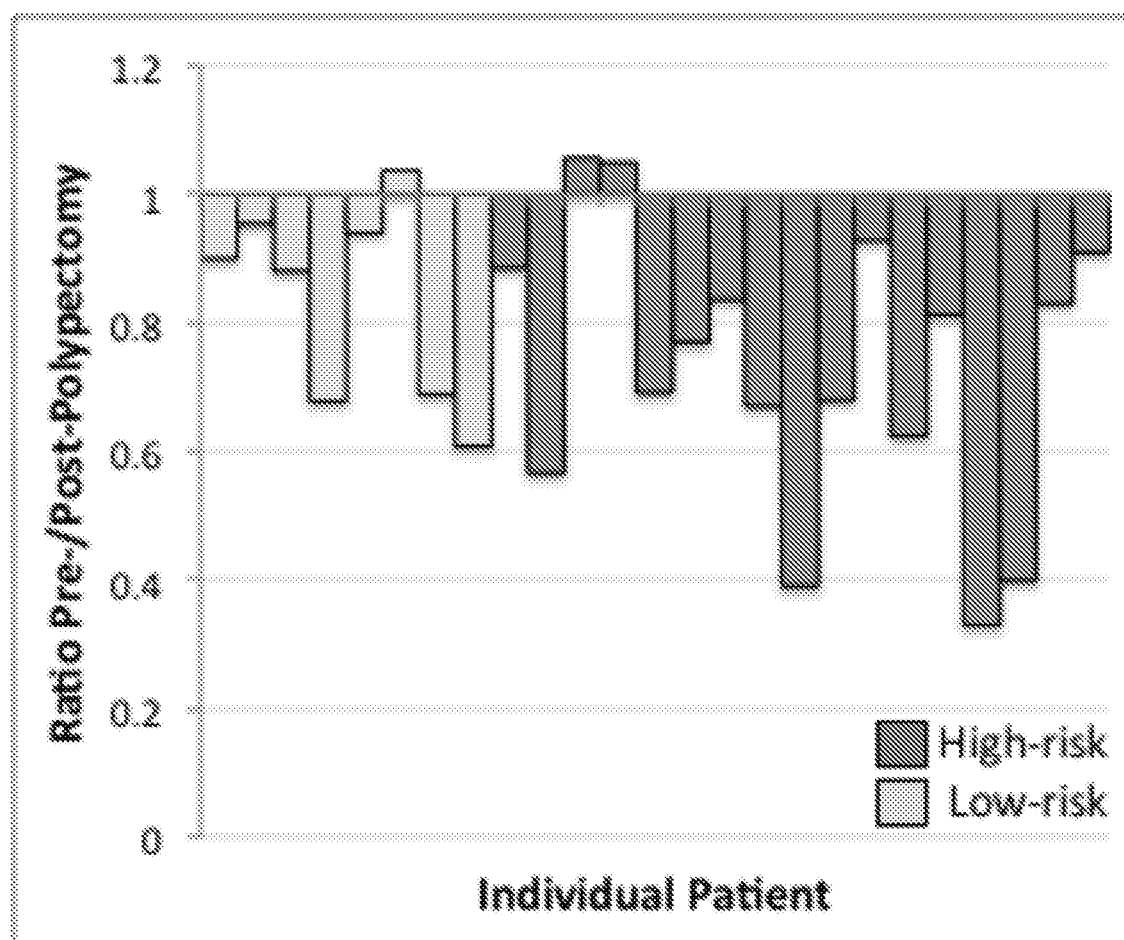

The average of all patients' pre-/post-polypectomy ratios identified protein biomarkers with statistically significant changes between the two groups. PI16 showed average expression changes toward normal levels after polyp removal (FIG. 26A, Table 7). PI16 typically shows downregulation in patients with adenomas, and in this case had a median pre-polypectomy ratio-to-reference standard (0.391) and an increased median post-polypectomy ratio-to-reference standard (0.544). The observed pre-polypectomy versus post-polypectomy expression change was not statistically significant when cases were binned between high-risk (advanced adenoma) cases and low-risk cases for PI16 (FIG. 26B, Table 7), meaning that there is an overall change in PI16 as a general response to polyp removal.

Figure 27:
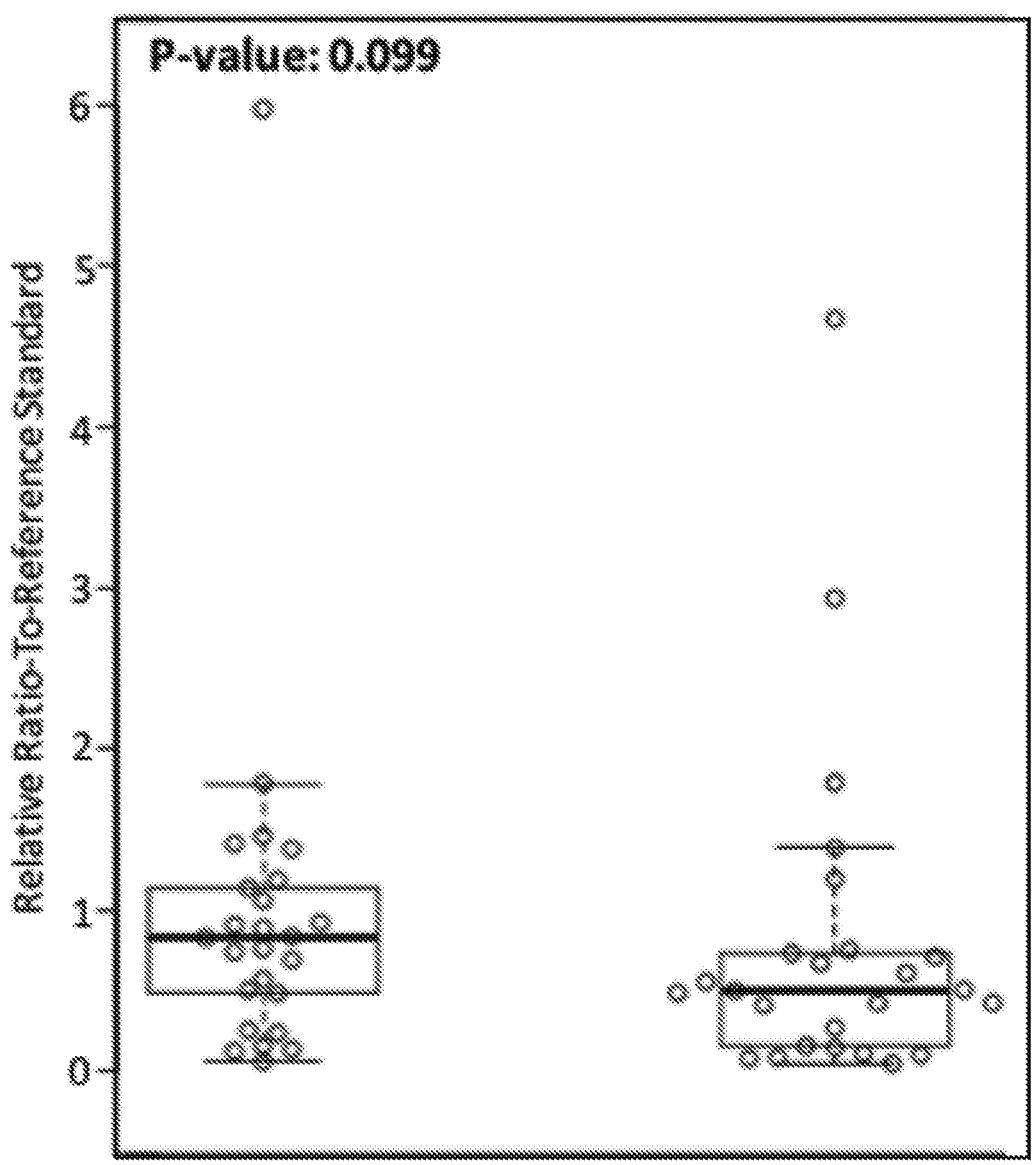
FIG. 27 shows CRP biomarker expression before and after polypectomy for adenomas in general (FIG. 26A) and for adenomas divided by risk of developing into cancer (FIG. 26B). In the dot plot shown in FIG. 26A, each circle in the indicated category on the x-axis represents one patient.
Figure 27:
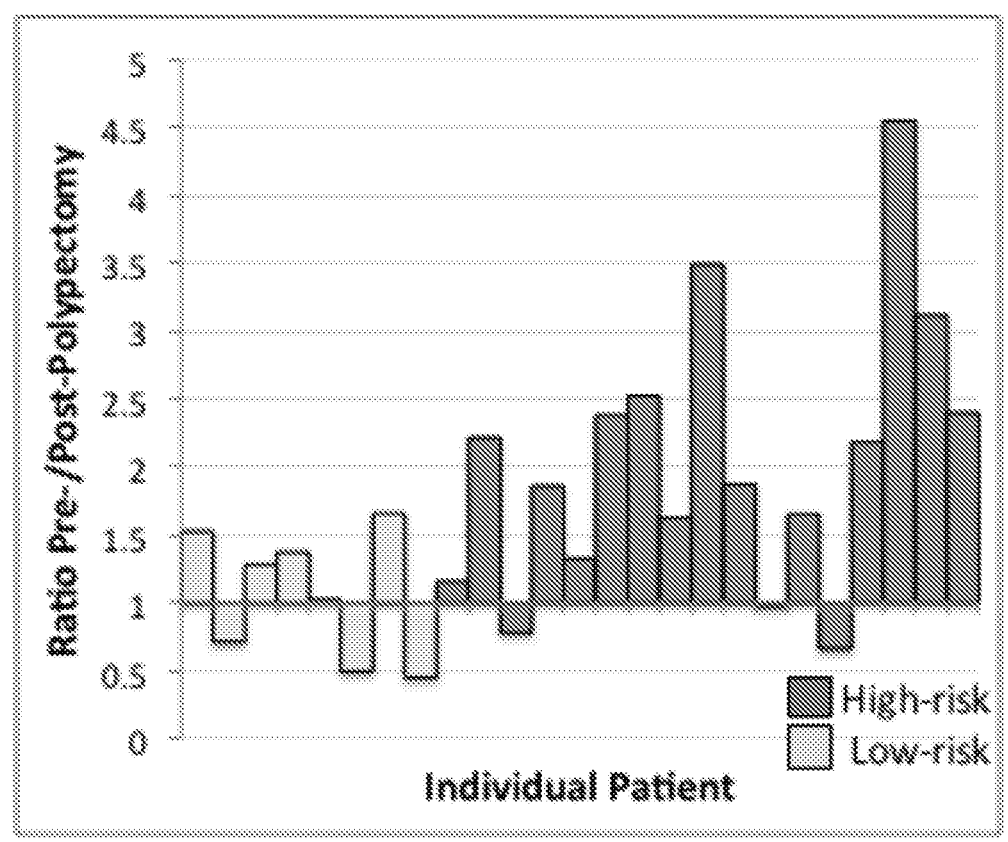

C-reactive protein (CRP) showed differences in pre-polypectomy versus post-polypectomy ratios in high-risk cases (FIG. 27, Table 7).

TABLE 7

Mann-Whitney p-values for pre-polypectomy versus post-polypectomy adenoma cases. Bolded values had a statistically significant p-value of less than 0.05.

| Mann-Whitney P-values for Pre- vs. Post-polypectomy data | PI16 | F5 | ITIH4 | CRP | LRG1 | DPP4 | EGFR | SOD3 | CDH2 | HPX |
|---|---|---|---|---|---|---|---|---|---|---|
| High-risk vs. Low-risk (Pre/Post ratio) | 0.28014 | 0.1096 | 0.4654 | 0.01314 | 0.61708 | 0.05614 | 0.74896 | 0.92828 | 0.79486 | 0.97606 |
| All Pre vs. All Post (Ratio-to-Standard) | 0.01878 | 0.61708 | 0.6672 | 0.09894 | 0.9442 | 0.74896 | 0.242 | 0.3125 | 0.62414 | 0.88866 |
| High Risk Pre vs. Post (Ratio-to-Standard) | 0.03846 | 0.35238 | 0.58232 | 0.06724 | 0.75656 | 0.63122 | 0.22246 | 0.27134 | 0.75656 | 0.88866 |
| High vs. Low Pre Only (Ratio-to-Standard) | 0.2187 | 0.88076 | 0.84148 | 0.79486 | 0.92828 | 0.44726 | 0.07508 | 0.58232 | 0.15272 | 0.4009 |

| Mann-Whitney P-values for Pre- vs. polypectomy data | ITIH3 | APCS | FETUB | VITD | CD44 | CFI | QSOX1 | THBS4 | VTN |
|---|---|---|---|---|---|---|---|---|---|
| High-risk vs. Low-risk (Pre/Post ratio) | 0.79486 | 0.09692 | 0.33706 | 0.97606 | 0.79486 | 0.17068 | 0.25428 | 0.9681 | 0.30772 |
| All Pre vs. All Post (Ratio-to-Standard) | 0.71138 | 0.4354 | 0.65272 | 0.42372 | 0.65272 | 0.8493 | 0.22246 | 0.0601 | 0.93624 |
| High Risk Pre vs. Post (Ratio-to-Standard) | 0.75656 | 0.42952 | 0.63122 | 0.36812 | 0.63122 | 0.86502 | 0.15854 | 0.04236 | 0.88866 |
| High vs. Low Pre Only (Ratio-to-Standard) | 0.65994 | 0.28014 | 0.50286 | 0.4654 | 0.74896 | 0.09692 | 0.84148 | 0.57548 | 0.65994 |

TABLE 8

Mann-Whitney p-values comparing known growing adenomas (linear growth) to adenomas of unknown growth and patients with screening normal colonoscopies. Bolded values had a statistically significant p-value of less than 0.05.

| Mann-Whitney P-values (Linear Polyp Growth) | PI16 | F5 | ITIH4 | CRP | LRG1 | DPP4 | EGFR | SOD3 | CDH2 | HPX |
|---|---|---|---|---|---|---|---|---|---|---|
| Growing vs. Screening Normal Colonoscopy | 0.01684 | 0.0002 | 0.42372 | 0.00048 | 0.03846 | 0.09296 | 0.71884 | 0.4009 | 0.19706 | 0.30302 |
| Unknown Growth vs. Screening Normal Colonoscopy | 0.77182 | 0.75656 | 0.15272 | 0.33204 | 0.77948 | 0.74896 | 0.93624 | 0.58232 | 0.99202 | 0.14986 |
| Growing vs. Unknown Growth | 0.00854 | 0.000011 | 0.02852 | 0.00714 | 0.0394 | 0.20766 | 0.85716 | 0.79486 | 0.12114 | 0.98404 |
| High Risk Growing vs. Screening Normal Colonoscopy | 0.07346 | 0.00104 | 0.31732 | 0.00138 | 0.07508 | 0.37886 | 0.48392 | 0.25848 | 0.59612 | 0.23404 |

| Mann-Whitney P-values (Linear Polyp Growth) | ITIH3 | APCS | FETUB | VITD | CD44 | CFI | QSOX1 | THBS4 | VTN |
|---|---|---|---|---|---|---|---|---|---|
| Growing vs. Screening Normal Colonoscopy | 0.4354 | 0.93624 | 0.69654 | 0.96012 | 0.31732 | 0.90448 | 0.3125 | 0.81034 | 0.0455 |
| Unknown Growth vs. Screening Normal Colonoscopy | 0.5287 | 0.61708 | 0.31732 | 0.65272 | 0.4777 | 0.35758 | 0.16452 | 0.42372 | 1 |
| Growing vs. Unknown Growth | 0.08012 | 0.69654 | 0.61708 | 0.80258 | 0.56868 | 0.238 | 0.99202 | 0.4965 | 0.06288 |
| High Risk Growing vs. Screening Normal Colonoscopy | 0.59612 | 0.85716 | 0.40654 | 0.7414 | 0.77182 | 0.36812 | 0.20054 | 0.44726 | 0.04444 |

Figure 28:
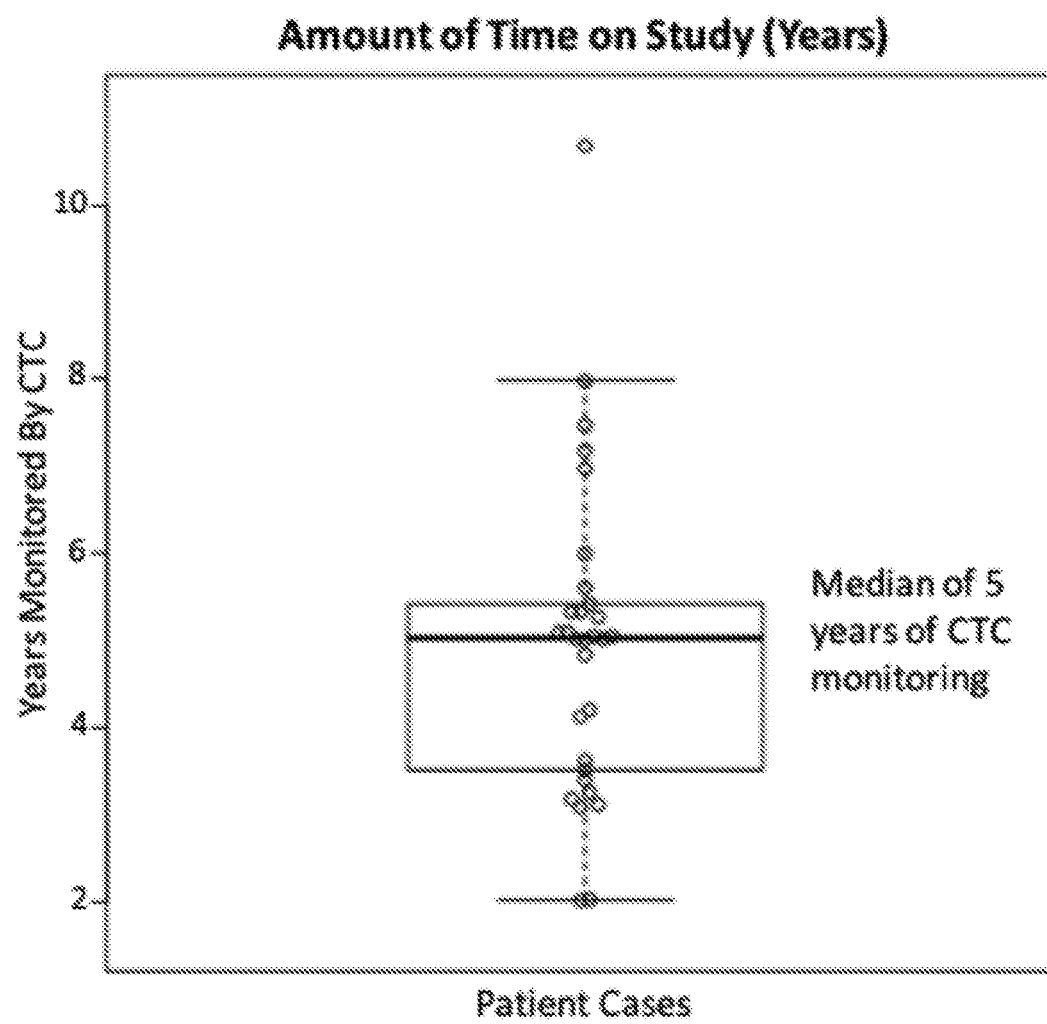
FIG. 28 plots the times individual patients were subject to longitudinal monitoring by CT Colonography (CTC) prior to polypectomy in the pre- and post-polypectomy study. Each circle represents one patient case and the median monitoring time was approximately 5 years.

Biomarker Expression in Known Growing Pre-Cancerous Polyps Compared to Those of Unknown Growth Patient cases whose blood biomarker expression was monitored pre- and post-polypectomy were also longitudinally monitored over a period of 2-10 years using CT Colonography CTC (FIG. 28). Table 9 describes the rules that were used to label patients as growing, static, regressing, or unknown growth. Briefly, any patient with a growing polyp was classified as growing regardless of all other polyps present. Polyps of unknown growth took precedence over static and regressing polyps because they had greater potential to grow. In the absence of growing polyps, or polyps with unknown growth, static polyps were considered more risky than polyps that were regressing because they are not shrinking and are more likely to change to a growing polyp status. Patient cases that were not monitored by CTC were pulled from the routine screening colonoscopy group to serve as additional comparisons to the growing polyp group in the form of screening normal controls and polyps of unknown growth.

TABLE 9

Growth Classification Assignments for Analyzing CTC Data

"G" = Growing    "U" = Unknown Growth    "S" = Static Growth    "R" = Regressing 1. If any polyp is growing, the entire patient case is classified as "Growing" regardless of the other polyps present.
2. If any case has an "unknown growth" polyp, the assumption is that it could be growing. Therefore, if the patient has any regressing or static polyps, the patient will still be classified as having unknown growth based on the possibility of a growing polyp.
3. If a patient has a static and a regressing polyp, the overall classification will be static. (This assumes a static polyp is more "dangerous" than a polyp that is showing signs of disappearing.)
4. Patients will only be classified as having regressing polyps if all polyps within the patient are regressing.

Figure 29A:
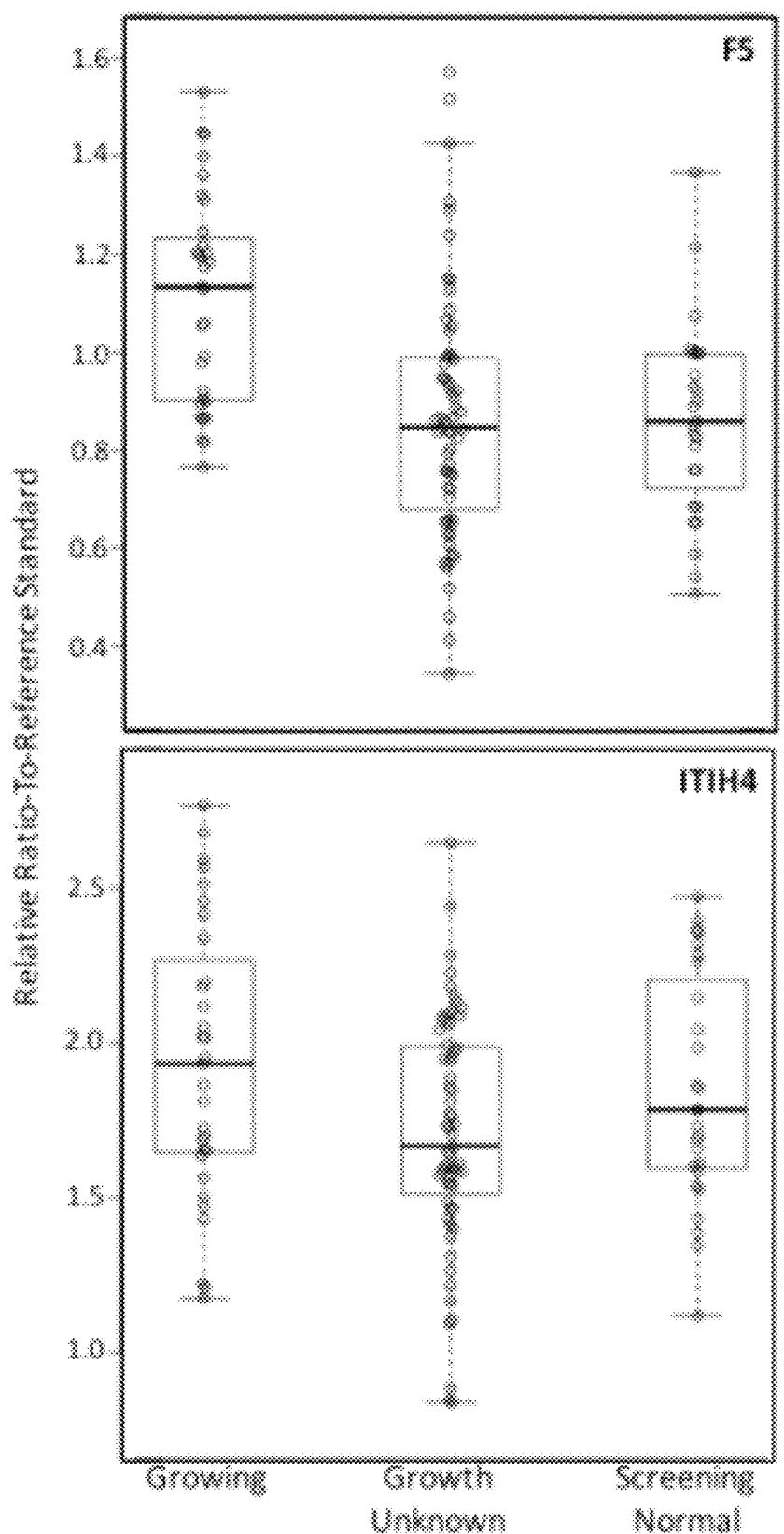
FIG. 29 shows relative ratio-to-reference standard data for the indicated biomarkers in patients with known growing adenomas and patient cases where adenomas of unknown growth were identified.
Figure 29B:
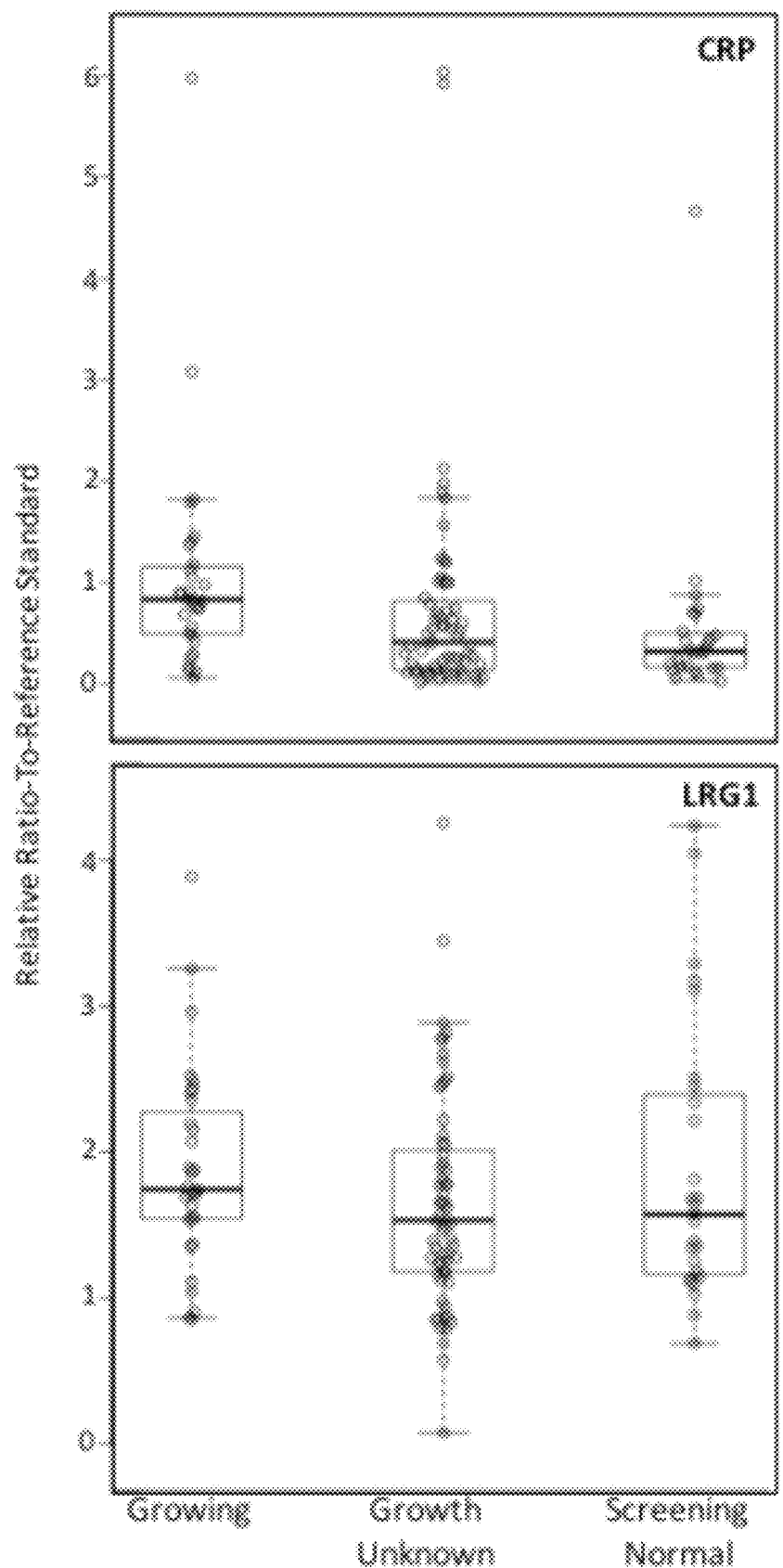
Figure 29C:
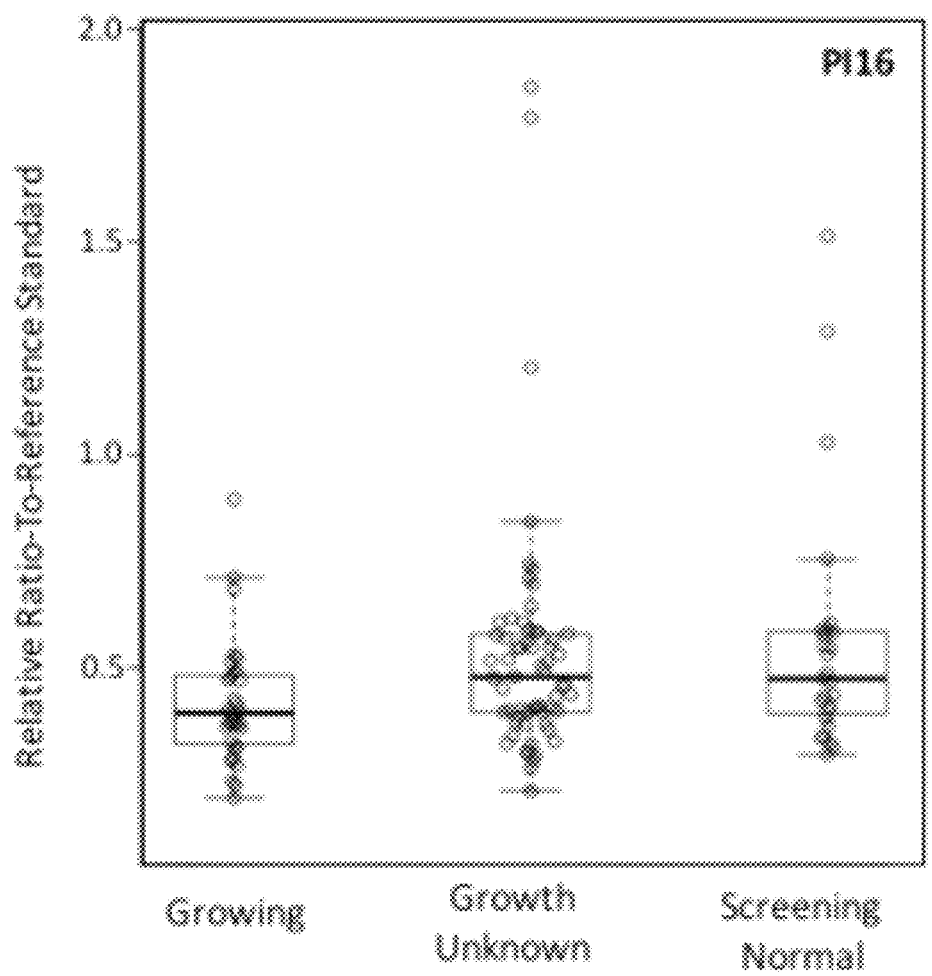

F5, CRP, PI16, ITIH4, and LRG1 all showed statistically significant changes in known growing adenoma cases compared to adenoma cases of unknown growth (FIG. 29, Table 8). All but ITIH4 also showed statistically significant protein expression changes in growing adenomas compared to screening normal colonoscopies.

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention is not necessarily limited to these particular aspects of the invention.

We claim:

1. A method for treating a colorectal cancer patient in need thereof with a neoadjuvant therapy after identifying the patient as having local or regional colorectal cancer, the method comprising:
   (a) assaying a biosample from the patient for the plurality of protein biomarkers comprising CD44, C-reactive protein, inter-alpha trypsin inhibitor, heavy chain H3vitamin D binding protein; and dipeptidyl peptidase 4, wherein the protein biomarkers are present in an individual without cancer at reference levels; and
   (b) detecting levels of the plurality of the protein biomarkers in the biosample;
   wherein the colorectal cancer patient is treated with neoadjuvant therapy when the levels of these protein biomarkers from the patient' biosample is higher than the reference protein biomarker levels from individuals without colorectal cancer.

2. The method of claim 1, wherein the biosample is assayed by a method comprising:
   (a) selecting one or more detectably labeled synthetic peptides with homology to one or a plurality of the protein biomarkers;
   (b) combining the detectably labeled synthetic peptides with the biosample; and
   (c) subjecting the combination to a physical separation method.

3. The method of claim 2, wherein the physical separation method is liquid chromatography.

4. The method of claim 2, wherein the synthetic peptides are isotopically labeled.

5. The method of claim 1, wherein detecting the level of one or a plurality of protein biomarkers comprises quantification of the concentration of protein biomarkers in the biosample.

6. The method of claim 1, wherein the assaying step comprises an immunologic assay.

7. The method of claim 6, wherein said immunologic assay comprises an enzyme-linked immunosorbent assay.

8. The method of claim 1, wherein the detecting step comprises mass spectrometry.

9. The method of claim 1, wherein the biosample is from a subject post-polypectomy, post-colectomy, or after other therapeutic intervention.

10. The method of claim 9, wherein the biosample is collected within 1 month, 2 months, 3 months, 4 months, 5 months or 6 months post-polypectomy.

11. The method of claim 9, wherein the biosample is collected within one year or two years post-polypectomy.

12. The method of claim 9, further comprising the step of (c) identifying an individual having a polyp following a polypectomy or other therapeutic intervention by comparing the level of the one or a plurality of the protein biomarkers in the biosample to a reference level of said one or a plurality of protein biomarkers.

13. The method of claim 1, wherein the method is non-invasive.

* * * * *

UNITED STATES PATENT AND TRADEMARK OFFICE
CERTIFICATE OF CORRECTION

PATENT NO. : 11,933,785 B2
APPLICATION NO. : 16/307779
DATED : March 19, 2024
INVENTOR(S) : Michael Richard Sussman et al.

It is certified that error appears in the above-identified patent and that said Letters Patent is hereby corrected as shown below:

In the Specification

Please add the following heading and paragraph in Column 1, Line 5, before the "CROSS-REFERENCE TO RELATED APPLICATIONS" heading:
STATEMENT REGARDING FEDERALLY SPONSORED RESEARCH
This invention was made with government support under TR000427 awarded by the National Institutes of Health. The government has certain rights in the invention.

Signed and Sealed this
Sixteenth Day of April, 2024

Katherine Kelly Vidal
*Director of the United States Patent and Trademark Office*